United States Patent
Kawaue et al.

(10) Patent No.: US 9,040,224 B2
(45) Date of Patent: May 26, 2015

(54) RESIST COMPOSITION, METHOD OF FORMING RESIST PATTERN AND COMPOUND

(71) Applicant: Tokyo Ohka Kogyo Co., Ltd., Kawasaki-shi (JP)

(72) Inventors: Akiya Kawaue, Kawasaki (JP); Takaaki Kaiho, Kawasaki (JP); Tsuyoshi Nakamura, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 14/133,000

(22) Filed: Dec. 18, 2013

(65) Prior Publication Data

US 2014/0178821 A1  Jun. 26, 2014

(30) Foreign Application Priority Data

Dec. 26, 2012 (JP) ................................. 2012-283450
Mar. 25, 2013 (JP) ................................. 2013-062810
Sep. 24, 2013 (JP) ................................. 2013-197580

(51) Int. Cl.
*G03F 7/004* (2006.01)
*C07C 309/00* (2006.01)
*G03F 7/30* (2006.01)

(52) U.S. Cl.
CPC ............... *G03F 7/0045* (2013.01); *G03F 7/30* (2013.01); *C07C 309/00* (2013.01); *Y10S 430/114* (2013.01); *Y10S 430/115* (2013.01)

(58) Field of Classification Search
CPC ......... G03F 7/004; G03F 7/0045; G03F 7/30; C07C 309/00
USPC ........................... 430/270.1, 913, 914; 562/30
See application file for complete search history.

(56) References Cited

U.S. PATENT DOCUMENTS

| | | | |
|---|---|---|---|
| 8,187,789 B2 * | 5/2012 | Yonemura et al. | 430/270.1 |
| 8,632,945 B2 * | 1/2014 | Maruyama | 430/270.1 |
| 2009/0197204 A1 | 8/2009 | Shiono et al. | |
| 2009/0226842 A1 * | 9/2009 | Shimizu et al. | 430/281.1 |
| 2009/0253070 A1 * | 10/2009 | Mizutani et al. | 430/270.1 |
| 2009/0317743 A1 | 12/2009 | Shiono et al. | |
| 2010/0143830 A1 * | 6/2010 | Ohashi et al. | 430/5 |
| 2010/0196820 A1 * | 8/2010 | Kawaue et al. | 430/270.1 |
| 2010/0209827 A1 * | 8/2010 | Ohashi et al. | 430/5 |
| 2010/0255419 A1 * | 10/2010 | Kodama et al. | 430/270.1 |
| 2010/0310985 A1 | 12/2010 | Mori et al. | |
| 2011/0027716 A1 * | 2/2011 | Yamaguchi et al. | 430/270.1 |
| 2011/0117499 A1 | 5/2011 | Matsumiya et al. | |
| 2011/0171577 A1 * | 7/2011 | Tsuchimura et al. | 430/270.1 |
| 2011/0244399 A1 | 10/2011 | Hirano et al. | |
| 2012/0009520 A1 | 1/2012 | Takeshita et al. | |
| 2012/0009521 A1 * | 1/2012 | Kawaue et al. | 430/281.1 |
| 2012/0149916 A1 | 6/2012 | Utsumi et al. | |
| 2012/0172606 A1 * | 7/2012 | Joo et al. | 549/78 |
| 2012/0196228 A1 * | 8/2012 | Nagasawa et al. | 430/285.1 |

FOREIGN PATENT DOCUMENTS

| | | |
|---|---|---|
| JP | A-2010-002870 | 1/2010 |
| JP | A-2010-032994 | 2/2010 |
| JP | A-2010-277043 | 12/2010 |
| JP | A-2011-013569 | 1/2011 |
| JP | A-2011-128226 | 6/2011 |
| JP | A-2011-191727 | 9/2011 |
| JP | A-2012-018304 | 1/2012 |
| JP | A-2012-121838 | 6/2012 |

* cited by examiner

*Primary Examiner* — Amanda C Walke
(74) *Attorney, Agent, or Firm* — Knobbe Martens Olson & Bear LLP

(57) ABSTRACT

A resist composition which generates acid upon exposure and exhibits changed solubility in a developing solution under action of acid, including a base component (A) which exhibits changed solubility in a developing solution under action of acid, and a photo-decomposable quencher (D0) containing a compound represented by general formula (d0) shown below. In the formula, $R^1$ represents a hydrocarbon group of 4 to 20 carbon atoms which may have a substituent; $Y^1$ represents a single bond or a divalent linking group; $R^2$ and $R^3$ each independently represents a substituent of 0 to 20 carbon atoms other than a fluorine atom; one of $R^2$ and $R^3$ may form a ring with $Y^1$; $M^{m+}$ represents an organic cation having a valency of m; and m represents an integer of 1 or more.

[Chemical Formula 1]

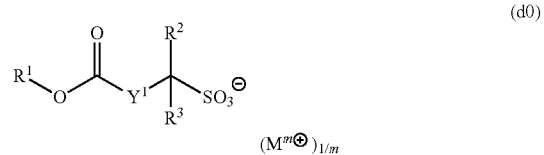

(d0)

7 Claims, No Drawings

RESIST COMPOSITION, METHOD OF FORMING RESIST PATTERN AND COMPOUND

TECHNICAL FIELD

The present invention relates to a resist composition, a method of forming a resist pattern and a compound.

Priority is claimed on Japanese Patent Application No. 2012-283450, filed Dec. 26, 2012, Japanese Patent Application No. 2013-062810, filed Mar. 25, 2013, and Japanese Patent Application No. 2013-197580, filed Sep. 24, 2013, the contents of which are incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production of the semiconductor elements. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified resist composition is used, which includes a base material component that exhibits a changed solubility in a developing solution under the action of acid and an acid generator component that generates acid upon exposure. For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If the resist film formed using the resist composition is selectively exposed during formation of a resist pattern, then within the exposed portions, acid is generated from the acid generator component, and the action of this acid causes an increase in the polarity of the base resin, making the exposed portions soluble in the alkali developing solution. Thus, by conducting alkali developing, the unexposed portions remain to form a positive resist pattern. On the other hand, in the case where such a resist composition is applied to a solvent developing process using a developing solution containing an organic solvent (organic developing solution), the polarity of the base resin at exposed portions is increased, whereas the solubility at exposed portions in an organic developing solution is relatively decreased. As a result, the unexposed portions of the resist film are dissolved and removed by the organic developing solution, and a negative resist pattern in which the exposed portions are remaining is formed. Such a solvent developing process for forming a negative-tone resist pattern is sometimes referred to as "negative-tone developing process" (for example, see Patent Document 1).

Recently, a chemically amplified resist composition including a photo-decomposable quencher has been proposed (for example, see Patent Documents 2 and 3). A photo-decomposable quencher is a salt composed of an anion moiety and a cation moiety, and functions as a quencher which traps the acid generated from an acid generator and the like, by salt exchange, and loses the function as a quencher after the decomposition upon exposure. When a resist film formed using a chemically amplified resist composition containing a photo-decomposable quencher is subjected to exposure, the photo-decomposable quencher loses the basicity thereof with respect to acid generated from an acid generator component and the like at exposed portions, whereas the photo-decomposable quencher traps acid at unexposed portions such that diffusion of acid from exposed portions to unexposed portions can be suppressed. As a result, lithography properties can be improved.

DOCUMENTS OF RELATED ART

Patent Document

[Patent Document 1] Japanese Unexamined Patent Application, First Publication No. 2011-191727
[Patent Document 2] Japanese Unexamined Patent Application, First Publication No. 2012-018304
[Patent Document 3] Japanese Unexamined Patent Application, First Publication No. 2012-121838

SUMMARY OF THE INVENTION

As further progress is made in lithography techniques and the application field for lithography techniques expands, further improvement in various lithography properties is demanded.

The present invention has an object of providing a resist composition capable of improving lithography properties, a method of forming a resist pattern using the resist composition, and a compound useful for the resist composition.

A first aspect of the present invention is a resist composition which generates acid upon exposure and exhibits changed solubility in a developing solution under action of acid, including a base component (A) which exhibits changed solubility in a developing solution under action of acid, and a photo-decomposable quencher (D0) containing a compound represented by general formula (d0) shown below.

[Chemical Formula 1]

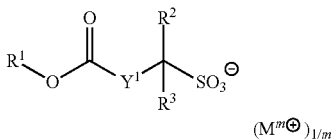

(d0)

In the formula, $R^1$ represents a hydrocarbon group of 4 to 20 carbon atoms which may have a substituent; $Y^1$ represents a single bond or a divalent linking group; $R^2$ and $R^3$ each independently represents a substituent of 0 to 20 carbon atoms other than a fluorine atom; one of $R^2$ and $R^3$ may form a ring with $Y^1$; $M^{m+}$ represents an organic cation having a valency of m; and m represents an integer of 1 or more.

A second aspect of the present invention is a method of forming a resist pattern, including: using a resist composition of the first aspect to form a resist film on a substrate; conducting exposure of the resist film; and developing the resist film to form a resist pattern.

A third aspect of the present invention is a compound represented by general formula (d0)-1 shown below.

[Chemical Formula 2]

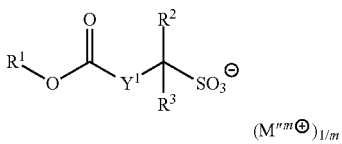

(d0)-1

In the formula, $R^1$ represents a hydrocarbon group of 4 to 20 carbon atoms which may have a substituent; $Y^1$ represents a single bond or a divalent linking group; $R^2$ and $R^3$ each independently represents a substituent of 0 to 20 carbon atoms other than a fluorine atom; one of $R^2$ and $R^3$ may form a ring with $Y^1$; $M'^{m+}$ represents a cation having a valency of m; and m represents an integer of 1 or more.

According to the present invention, there are provided a resist composition capable of improving lithography properties, a method of forming a resist pattern using the resist composition, and a compound useful for the resist composition.

MODE FOR CARRYING OUT THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified.

The term "alkylene group" includes linear, branched or cyclic, divalent saturated hydrocarbon, unless otherwise specified. The same applies for the alkyl group within an alkoxy group.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with fluorine atom(s).

The term "structural unit" refers to a monomer unit that contributes to the formation of a polymeric compound (resin, polymer, copolymer).

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid ($CH_2=CH-COOH$) has been substituted with an organic group.

The acrylate ester may have the hydrogen atom bonded to the carbon atom on the α-position substituted with a substituent. The substituent ($R^α$) that substitutes the hydrogen atom bonded to the carbon atom on the α-position is an atom other than hydrogen or a group, and examples thereof include an alkyl group of 1 to 5 carbon atoms, a halogenated alkyl group of 1 to 5 carbon atoms and a hydroxyalkyl group. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

A "structural unit derived from hydroxystyrene or a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

The term "styrene" includes styrene itself and compounds in which the hydrogen atom at the α-position of styrene has been substituted with another substituent such as an alkyl group or a halogenated alkyl group.

A "structural unit derived from styrene or a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

The expression "may have a substituent" means that a case where a hydrogen atom (—H) is substituted with a monovalent group, or a case where a methylene (—$CH_2$—) group is substituted with a divalent group.

The term "exposure" is used as a general concept that includes irradiation with any form of radiation.

An "organic group" refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

<<Resist Composition>>

The resist composition of the present invention is a resist composition which generates acid upon exposure and exhibits changed solubility in a developing solution under action of acid, and which includes a base component (A) which exhibits changed solubility in a developing solution under action of acid, and a photo-decomposable quencher (D0) containing a compound represented by general formula (d0).

The resist composition of the present invention is a resist composition which generates acid upon exposure and exhibits changed solubility in a developing solution under action of acid, and which includes a base component (A) which exhibits changed solubility in a developing solution under action of acid (hereafter, sometimes referred to as "component (A)").

When a resist film is formed using the resist composition and the formed resist film is subjected to a selective exposure, acid is generated at exposed portions, and the generated acid acts on the component (A) to change the solubility of the component (A) in a developing solution, whereas the solubility of the component (A) in a developing solution is not changed at unexposed portions, thereby generating difference in solubility in a developing solution between exposed portions and unexposed portions. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

The resist composition of the present invention may be either a positive resist composition or a negative resist composition.

Further, in the formation of a resist pattern, the resist composition of the present invention can be applied to either an alkali developing process using an alkali developing solution in the developing treatment, or a solvent developing process using a developing solution containing an organic solvent (organic developing solution) in the developing treatment.

The resist composition of the present invention has a function of generating acid upon exposure, and in the resist composition, the component (A) may generate acid upon exposure, or an additive component other than the component (A) may generate acid upon exposure.

More specifically, the resist composition of the present invention may be a resist composition (1) containing an acid generator component (B) which generates acid upon exposure (hereafter, sometimes referred to as "component (B)");

a resist composition (2) in which the component (A) is a component which generates acid upon exposure; or a resist composition (3) in which the component (A) is a component which generates acid upon exposure, and further containing an acid generator component (B).

That is, when the resist composition of the present invention is the aforementioned resist composition (2) or (3), the component (A) is a "base component which generates acid upon exposure and exhibits changed solubility in a developing solution under action of acid". In the case where the component (A) is a base component which generates acid upon exposure and exhibits changed solubility in a developing solution under action of acid, the component (A1) described later is preferably a polymeric compound which generates acid upon exposure and exhibits changed solubility in a developing solution under action of acid. As such a polymeric compound, a resin having a structural unit which generates acid upon exposure can be used. As such a structural unit which generates acid upon exposure, a conventional structural unit can be used.

The resist composition of the present invention is particularly preferably the aforementioned resist composition (1).

<Component (A)>

In the present invention, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" refers to a polymer having a molecular weight of 1,000 or more.

As the molecular weight of the polymer, the weight average molecular weight in terms of the polystyrene equivalent value determined by gel permeation chromatography (GPC) is used.

As the component (A), a resin, a low molecular weight compound, or a combination thereof may be used.

The component (A) may be a component that exhibits increased solubility in a developing solution under action of acid or a component that exhibits decreased solubility in a developing solution under action of acid.

In the present invention, the component (A) may be a component that generates acid upon exposure.

In the present invention, the base component (A) preferably contains a resin component (A1) which has a structural unit (a1) containing an acid decomposable group that exhibits increased polarity by the action of acid.

(Structural Unit (a1))

The structural unit (a1) is a structural unit containing an acid decomposable group that exhibits increased polarity by the action of acid.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of acid to form a polar group.

Examples of the polar group include a carboxy group, a hydroxy group, an amino group and a sulfo group ($-SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

Here, the "acid dissociable group" is (i) a group in which the bond between the acid dissociable group and the adjacent atom is cleaved by the action of acid; and (ii) a group in which one of the bonds is cleaved by the action of acid, or then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1) is increased. By the increase in the polarity, the solubility in a developing solution changes and, the solubility in an organic developing solution is relatively decreased.

The acid dissociable group is not particularly limited, and any of the groups that have been conventionally proposed as acid dissociable groups for the base resins of chemically amplified resists can be used.

Examples of the acid dissociable group for protecting the carboxy group or hydroxy group as a polar group include the acid dissociable group represented by general formula (a1-r-1) shown below (hereafter, sometimes referred to as "acetal-type acid dissociable group").

[Chemical Formula 3]

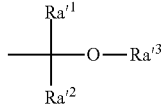

(a1-r-1)

In the formula, $Ra'^1$ and $Ra'^2$ represents a hydrogen atom or an alkyl group; and $Ra'^3$ represents a hydrocarbon group, provided that $Ra'^3$ may be bonded to $Ra'^1$ or $Ra'^2$ to form a ring.

In the formula (a1-r-1), as the alkyl group for $Ra'^1$ and $Ra'^2$, the same alkyl groups as those described above the alkyl groups as the substituent which may be bonded to the carbon atom on the α-position of the aforementioned α-substituted alkylester can be used, although a methyl group or ethyl group is preferable, and a methyl group is particularly desirable.

As the hydrocarbon group for $Ra'^3$, an alkyl group of 1 to 20 carbon atoms is preferable, an alkyl group of 1 to 10 carbon atoms is more preferable, and a linear or branched alkyl group is still more preferable. Specific examples thereof include a methyl group, an ethyl group, a propyl group, an isopropyl group, an n-butyl group, an isobutyl group, a tert-butyl group, a pentyl group, an isopentyl group, a neopentyl group, 1,1-dimethylethyl group, 1,1-diethylpropyl group, 2,2-dimethylpropyl group and 2,2-dimethylbutyl group.

When $Ra'^3$ is a cyclic hydrocarbon group, the hydrocarbon group may be either an aliphatic group or an aromatic group, and may be either a polycyclic group or a monocyclic group. As the monocyclic alicyclic hydrocarbon group, a group in which one hydrogen atom has been removed from a monocycloalkane is preferable. The monocycloalkane preferably has 3 to 8 carbon atoms, and specific examples thereof include cyclopentane, cyclohexane and cyclooctane. As the polycyclic alicyclic hydrocarbon group, a group in which one hydrogen atom has been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which one hydrogen atom has been removed from the aforementioned aromatic hydrocarbon ring (aryl group); and a group in which one hydrogen atom of the aforementioned aryl group has been substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atoms, more preferably 1 or 2, and most preferably 1.

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

Examples of the acid dissociable group for protecting the carboxy group as a polar group include the acid dissociable group represented by general formula (a1-r-2) shown below (hereafter, with respect to the acid dissociable group represented by the following formula (a1-r-2), the acid dissociable group constituted of alkyl groups is referred to as "tertiary ester-type acid dissociable group").

[Chemical Formula 4]

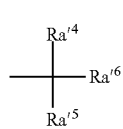

(a1-r-2)

In the formula, $Ra'^4$ to $Ra'^6$ each independently represents a hydrocarbon group, provided that $Ra'^5$ and $Ra'^6$ may be mutually bonded to form a ring.

As the hydrocarbon group for $Ra'^4$ to $Ra'^6$, the same groups as those described above for $Ra'^3$ can be mentioned. $Ra'^4$ is preferably an alkyl group of 1 to 5 carbon atoms. In the case where $Ra'^1$ and $Ra'^6$ are mutually bonded to form a ring, a group represented by general formula (a1-r2-1) shown below can be mentioned.

On the other hand, in the case where $Ra'^4$ to $Ra'^6$ are not mutually bonded and independently represent a hydrocarbon group, the group represented by general formula (a1-r2-2) shown below can be mentioned.

[Chemical Formula 5]

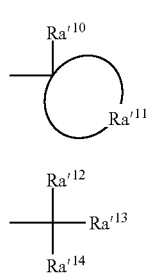

(a1-r2-1)

(a1-r2-2)

In the formulae, $Ra'^{10}$ represents an alkyl group of 1 to 10 carbon atoms; $Ra'^{11}$ is a group which forms an aliphatic cyclic group together with a carbon atom having $Ra'^{10}$ bonded thereto; and $Ra'^{12}$ to $Ra'^{14}$ each independently represents a hydrocarbon group.

In the formula (a1-r2-1), as the alkyl group of 1 to 10 carbon atoms for $Ra'^{10}$, the same groups as described above for the linear or branched alkyl group for $Ra'^3$ in the formula (a1-r-1) are preferable. In the formula (a1-r2-1), as the aliphatic cyclic group which is formed by $Ra'^{11}$, the same groups as those described above for the cyclic alkyl group for $Ra'^3$ in the formula (a1-r-1) are preferable.

In the formula (a1-r2-2), it is preferable that $Ra'^{12}$ and $Ra'^{14}$ each independently represents an alkyl group or 1 to 10 carbon atoms, and it is more preferable that the alkyl group is the same group as the described above for the linear or branched alkyl group for $Ra'^3$ in the formula (a1-r-1), it is still more preferable that the alkyl group is a linear alkyl group of 1 to 5 carbon atoms, and it is particularly preferable that the alkyl group is a methyl group or an ethyl group.

In the formula (a1-r2-2), it is preferable that $Ra'^{13}$ is the same group as described above for the linear, branched or cyclic alkyl group for $Ra'^3$ in the formula (a1-r-1).

Among these, the same cyclic alkyl group as those describe above for $Ra'^3$ is more preferable.

Specific examples of the formula (a1-r2-1) are shown below. The "*" in the formula represents a valence bond.

[Chemical Formula 6]

(r-pr-m1)

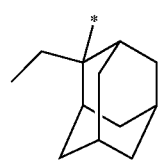

(r-pr-m2)

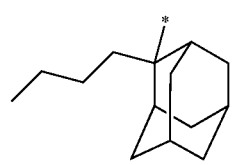

(r-pr-m3)

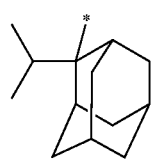

(r-pr-m4)

(r-pr-m5)

(r-pr-m6)

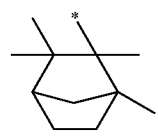

(r-pr-m7)

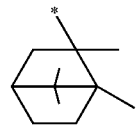

(r-pr-m8)

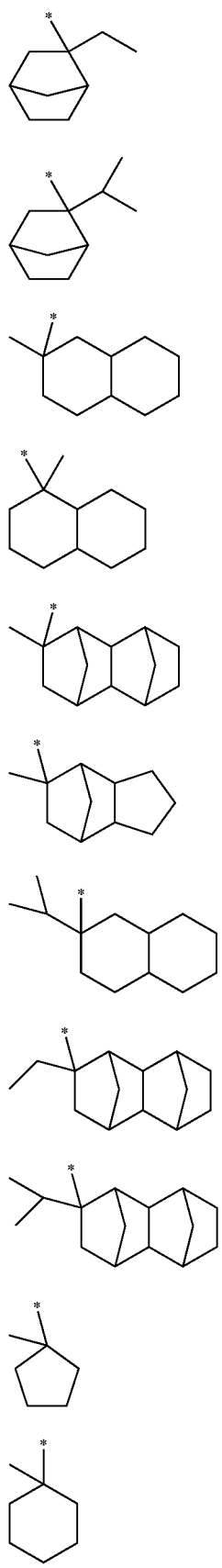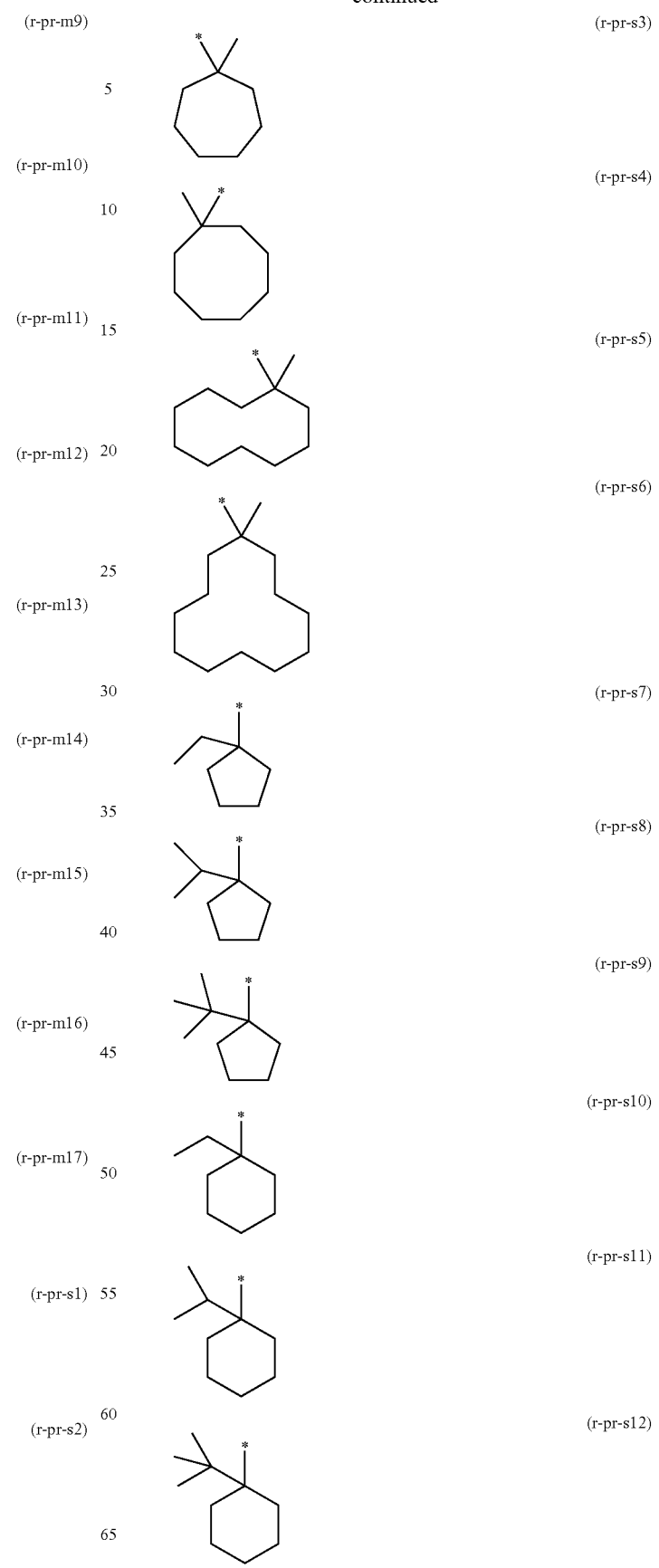

(r-pr-s13)
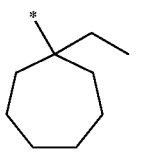
(r-pr-s14)
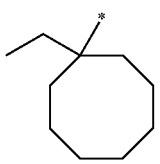
(r-pr-s15)
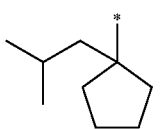
(r-pr-s16)
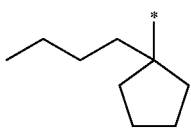
(r-pr-s17)
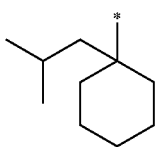
(r-pr-s18)
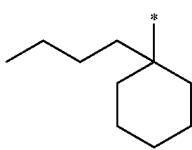
Specific examples of the formula (a1-r2-2) are shown below.
[Chemical Formula 7]
(r-pr-cm1)
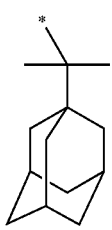
(r-pr-cm2)
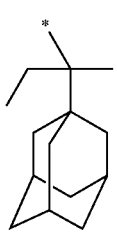
(r-pr-cm3)
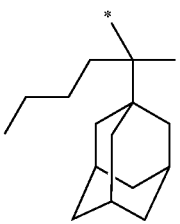
(r-pr-cm4)
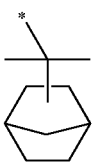
(r-pr-cm5)
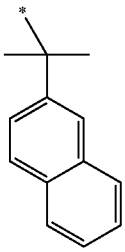
(r-pr-cm6)
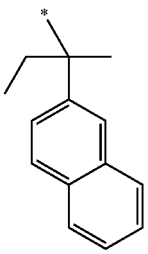
(r-pr-cm7)
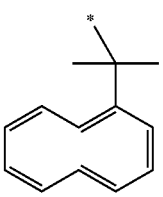
(r-pr-cm8)
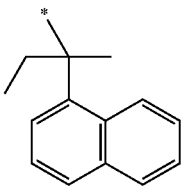
(r-pr-cs1)
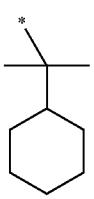

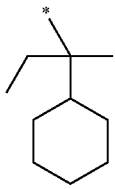
(r-pr-cs2)

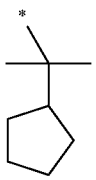
(r-pr-cs3)

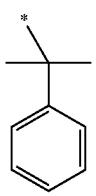
(r-pr-cs4)

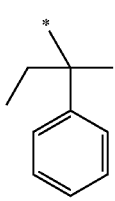
(r-pr-cs5)

(r-pr-c1)

(r-pr-c2)

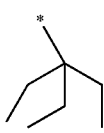
(r-pr-c3)

Examples of the acid dissociable group for protecting a hydroxy group as a polar group include the acid dissociable group represented by general formula (a1-r-3) shown below (hereafter, referred to as "tertiary alkyloxycarbonyl-type acid dissociable group").

[Chemical Formula 8]

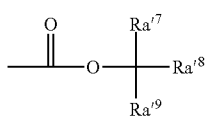
(a1-r-3)

In the formula, $Ra'^7$ to $Ra'^9$ each represents an alkyl group.

In the formula (a1-r-3), $Ra'^7$ to $Ra'^9$ is preferably an alkyl group of 1 to 5 carbon atoms, and more preferably an alkyl group of 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent and contains an acid decomposable group which exhibits increased polarity by the action of acid; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

As the structural unit (a1), structural units represented by general formulas (a1-1) to (a1-3) shown below are preferable.

[Chemical Formula 9]

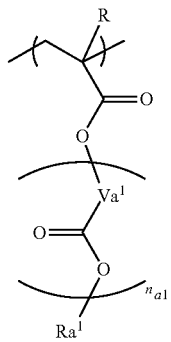
(a1-1)

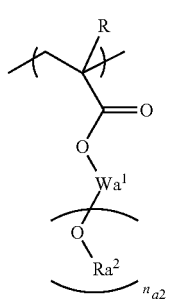
(a1-2)

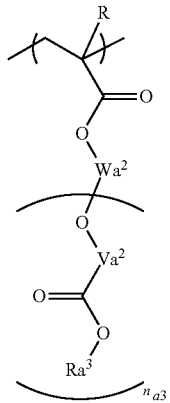

(a1-3)

In the formulae, R represents a hydrogen atom, an alkyl group of 1 to 5 carbon atoms or a halogenated alkyl group of 1 to 5 carbon atoms; $Va^1$ represents a divalent hydrocarbon group which may contain a linking group selected from the group consisting of an ether bond, an urethane bond and an amide bond; $n_{a1}$ represents an integer of 0 to 2;

$Ra^1$ represents an acid dissociable group represented by the aforementioned formulae (a1-r-1) to (a1-r-2);

$Wa^1$ represents a hydrocarbon group having a valency of $n_{a2}+1$; $n_{a2}$ represents 1 to 3;

$Ra^2$ represents an acid dissociable group represented by the aforementioned formulae (a1-r-1) or (a1-r-3);

$Wa^2$ represents a hydrocarbon group having a valency of $n_{a3}+1$; $n_{a3}$ represents 1 to 3;

$Va^2$ represents a divalent hydrocarbon group which may contain a linking group selected from the group consisting of an ether bond, an urethane bond and an amide bond; and $Ra^3$ represents an acid dissociable group represented by the aforementioned formulae (a1-r-1) or (a1-r-2).

In general formula (a1-1), as the alkyl group of 1 to 5 carbon atoms, a linear or branched alkyl group of 1 to 5 carbon atoms is preferable, and specific examples include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

The hydrocarbon group for $Va^1$ may be either an aliphatic hydrocarbon group or an aromatic hydrocarbon group. An "aliphatic hydrocarbon group" refers to a hydrocarbon group that has no aromaticity. The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

Further, as the group for $Va^1$, a group in which the aforementioned divalent hydrocarbon group has been bonded via an ether bond, urethane bond or amide bond can be mentioned.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable, and specific examples include a methylene group [—$CH_2$—], an ethylene group [—$(CH_2)_2$-], a trimethylene group [—$(CH_2)_3$-], a tetramethylene group [—$(CH_2)_4$-] and a pentamethylene group [—$(CH_2)_5$-].

As the branched aliphatic hydrocarbon group, a branched alkylene group is preferable, and specific examples include alkylalkylene groups, e.g., alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

As examples of the aliphatic hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of a linear or branched aliphatic hydrocarbon group, and a group in which the alicyclic hydrocarbon group is interposed within a linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic alicyclic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which two hydrogen atoms have been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

The aromatic hydrocarbon group is a hydrocarbon group having an aromatic ring.

The aromatic hydrocarbon group as the divalent hydrocarbon group for $Va^1$ preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (for example, a group in which one hydrogen atom has been removed from an aryl group within an arylalkyl group such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atoms, more preferably 1 or 2, and most preferably 1.

In the aforementioned formula (a1-2), the hydrocarbon group for $Wa^1$ having a valency of $n_{a2}+1$ may be either an aliphatic hydrocarbon group or an aromatic hydrocarbon group. The aliphatic hydrocarbon group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a2}+1$ is preferably divalent, trivalent or tetravalent, and divalent or trivalent is more preferable.

In the aforementioned formula (a1-3), the hydrocarbon group for $Wa^1$ having a valency of $n_{a3}+1$ may be either an aliphatic hydrocarbon group or an aromatic hydrocarbon group. The aliphatic hydrocarbon group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a3}+1$ is preferably divalent, trivalent or tetravalent, and divalent or trivalent is more preferable.

In the formula (a1-3), $Va^2$ is the same group as defined above for $Va^1$ in the formula (a1-1).

As the structural unit represented by the aforementioned formula (a1-2), a structural unit represented by general formula (a1-2-01) shown below is desirable.

[Chemical Formula 10]

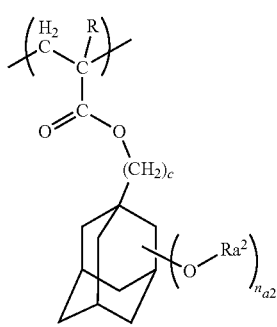

(a1-2-01)

In the formula (a1-2-01), $Ra^2$ represents an acid dissociable group represented by the aforementioned formulae (a1-r-1) or (a1-r-3); $n_{a2}$ is an integer of 1 to 3, preferably 1 or 2, and more preferably 1; c is an integer of 0 to 3, preferably 0 or 1, and more preferably 1; and R is the same as defined above.

Specific examples of the structural units (a1-1) and (a1-2) are shown below. In the formulas shown below, $R^\alpha$ represents a hydrogen atom, a methyl group or a trifluoromethyl group.

[Chemical Formula 11]

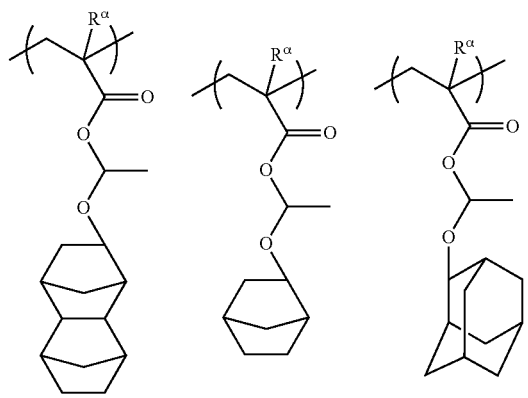

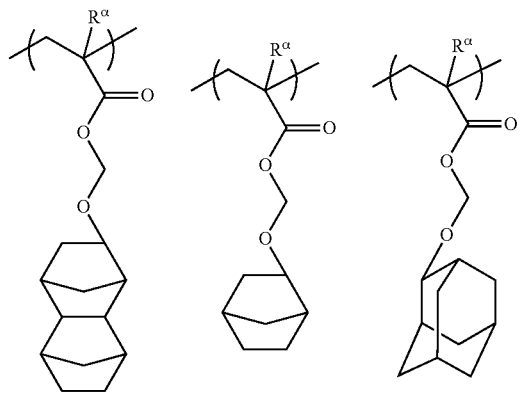

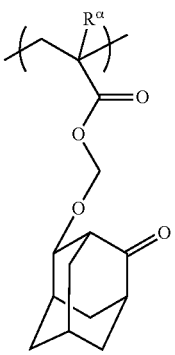

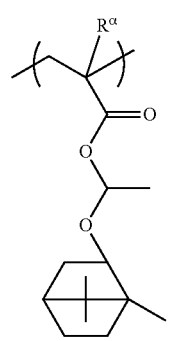

-continued
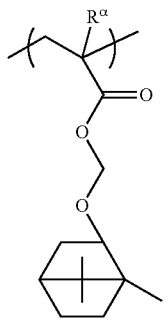
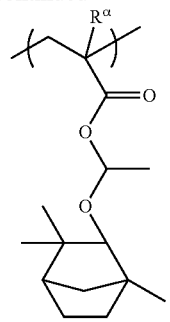
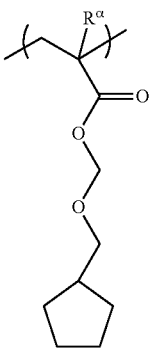
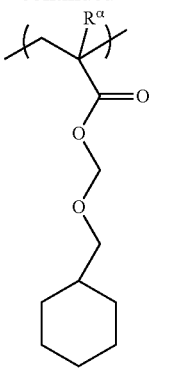
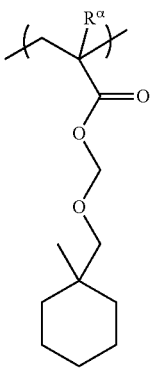
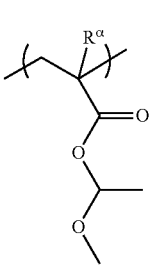
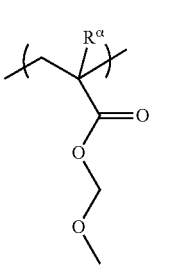
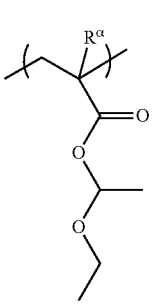
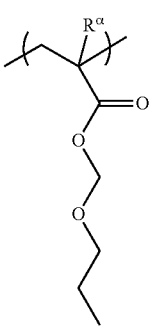
[Chemical Formula 13]
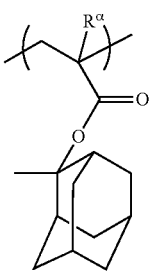
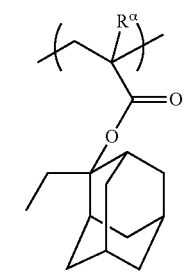
[Chemical Formula 12]
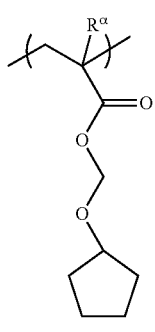
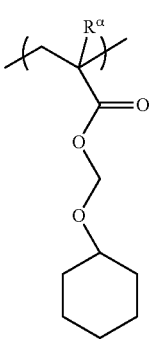
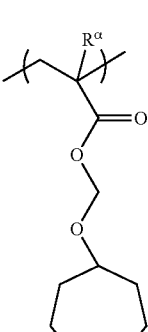
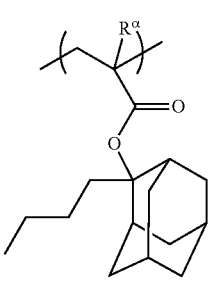
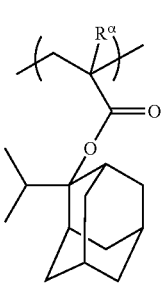

[Chemical Formula 14]
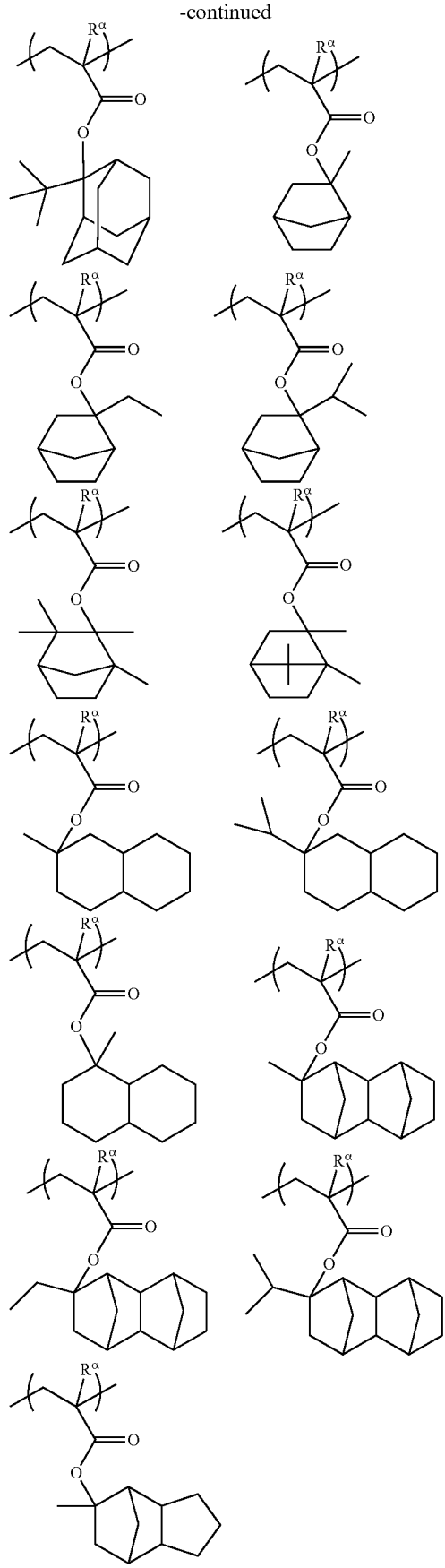
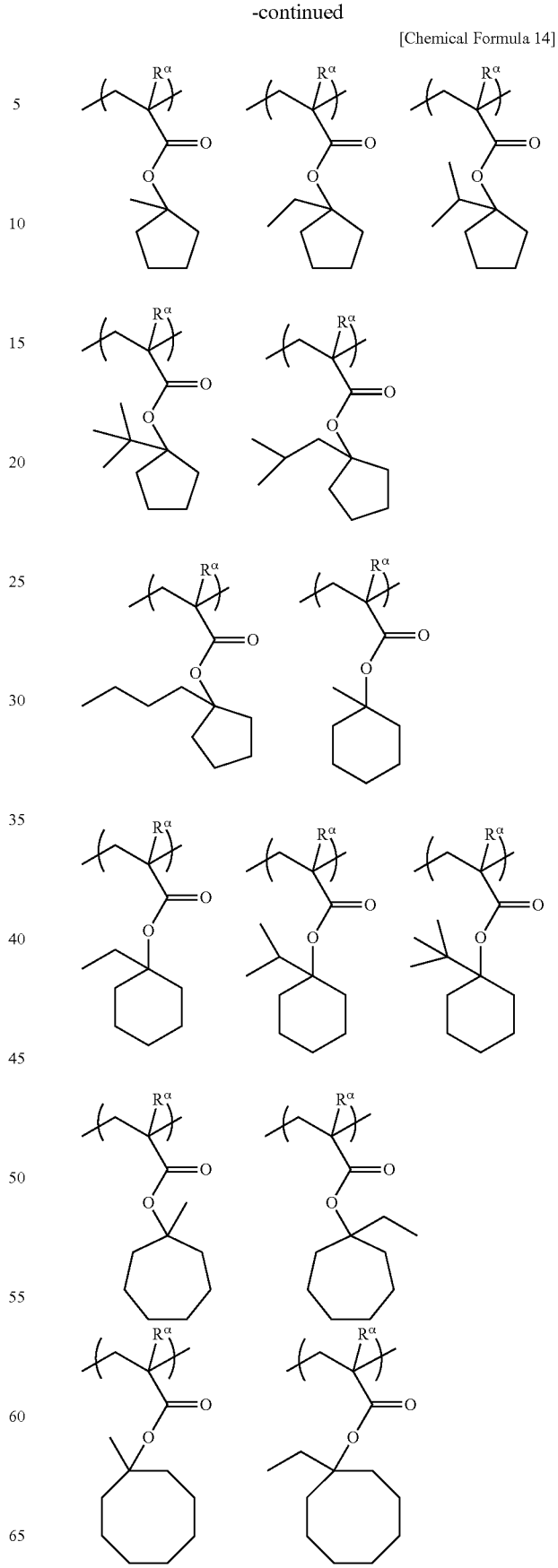

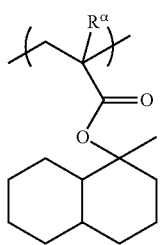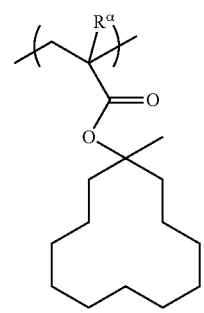
[Chemical Formula 15]
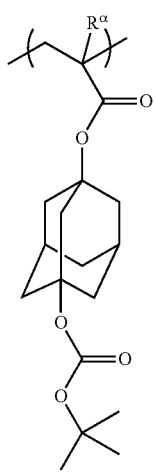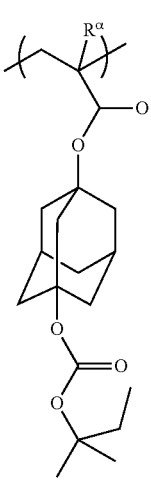
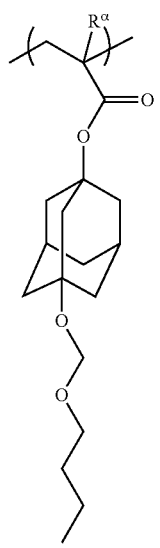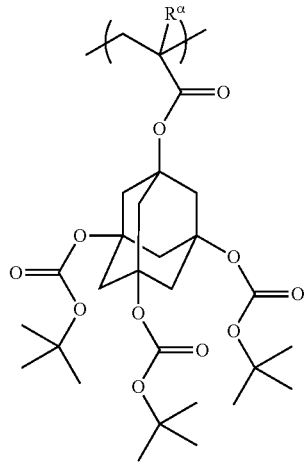
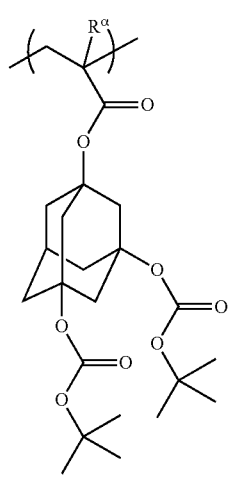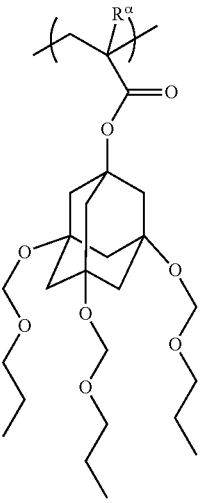
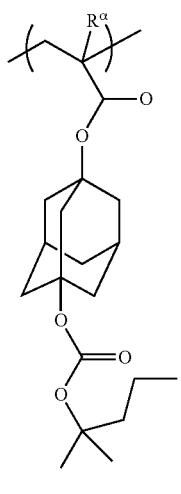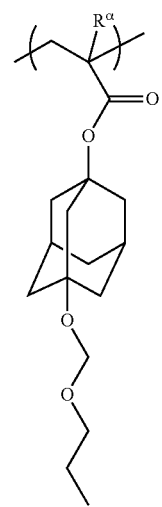
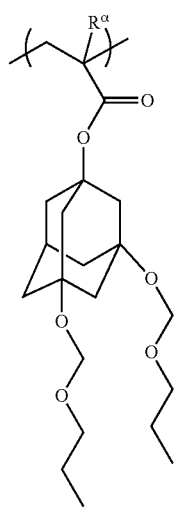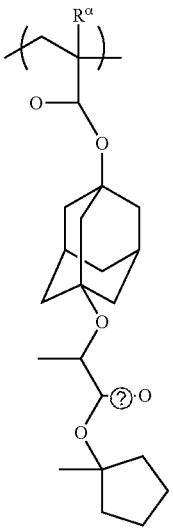

-continued

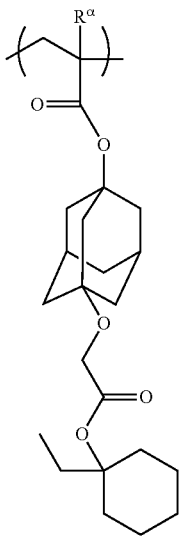
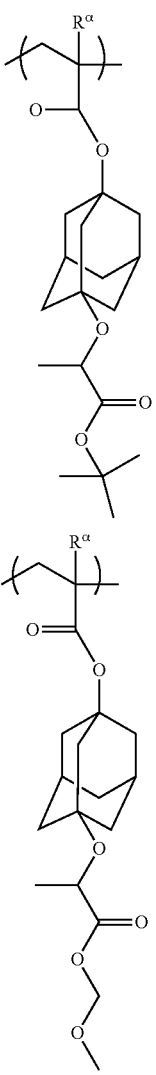
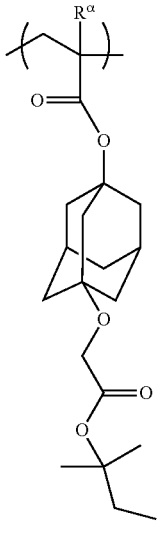
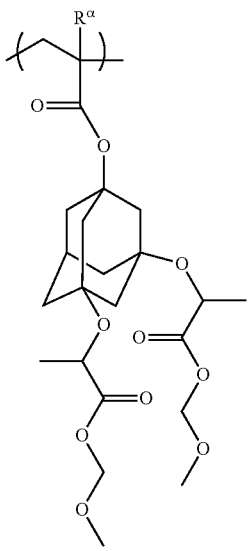

In the component (A), the amount of the structural unit (a1) based on the combined total of all structural units constituting the component (A) is preferably 20 to 80 mol %, more preferably 20 to 75 mol %, and still more preferably 25 to 70 mol %. By ensuring the lower limit, various lithography properties such as sensitivity, resolution and LWR are improved. On the other hand, when the amount of the structural unit (a1) is no more than the upper limit of the above-mentioned range, a good balance can be achieved with the other structural units.

(Other Structural Units)

In the present invention, the resin compound (A1) may also include the structural units (a2) to (a4) and (a9) described later.

(Structural Unit (a2))

The structural unit (a2) is a structural unit which contains a lactone-containing cyclic group, an —$SO_2$— containing cyclic group or a carbonate-containing cyclic group, and which does not fall under the definition of the structural unit (O).

When the component (A1) is used for forming a resist film, the lactone-containing cyclic group or the carbonate-containing cyclic group within the structural unit (a2) is effective in improving the adhesion between the resist film and the substrate.

The aforementioned structural unit (a1) which contains a lactone-containing cyclic group or a carbonate-containing cyclic group falls under the definition of the structural unit (a2); however, such a structural unit is regarded as a structural unit (a1), and does not fall under the definition of the structural unit (a2).

When the component (A1) is used for forming a resist film, the —$SO_2$— containing cyclic group within the structural unit (a2) is effective in improving the adhesion between the resist film and the substrate.

The aforementioned structural unit (a1) which contains a —$SO_2$— containing cyclic group falls under the definition of the structural unit (a2); however, such a structural unit is regarded as a structural unit (a1), and does not fall under the definition of the structural unit (a2).

The structural unit (a2) is preferably a structural unit represented by general formula (a2-1) shown below.

[Chemical Formula 16]

(a2-1)

In the formula, R represents a hydrogen atom, an alkyl group of 1 to 5 carbon atoms or a halogenated alkyl group of 1 to 5 carbon atoms; $Ya^{21}$ represents a single bond or a divalent linking group; $La^{21}$ represents —O—, —COO—, —CON(R')—, —OCO—, —CONHCO— or —CONHCS; and R' represents a hydrogen atom or a methyl group, provided that when $La^{21}$ represents —O—, $Ya^{21}$ does not represents —CO—; and $Ra^{21}$ represents a lactone-containing cyclic group, a carbonate-containing cyclic group or an —$SO_2$— containing cyclic group.

The divalent linking group for $Ya^{21}$ is not particularly limited, and preferable examples thereof include a divalent hydrocarbon group which may have a substituent and a divalent linking group containing a hetero atom.

(Divalent Hydrocarbon Group which May have a Substituent)

The hydrocarbon group as a divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given. Specific examples thereof include the same group as exemplified above for $Va^1$ in the aforementioned formula (a1-1).

The linear or branched aliphatic hydrocarbon group may or may not have a substituent. Examples of the substituent include a fluorine atom, a fluorinated alkyl group of 1 to 5 carbon atoms, and a carbonyl group.

As examples of the aliphatic hydrocarbon group containing a ring in the structure thereof, a cyclic aliphatic hydrocarbon group which may have a substituent containing a hetero atom in the ring structure thereof (a group in which two hydrogen atoms have been removed from an aliphatic hydrocarbon ring), a group in which the cyclic aliphatic hydrocarbon group is bonded to the terminal of a linear or branched aliphatic hydrocarbon group, and a group in which the cyclic aliphatic hydrocarbon group is interposed within a linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

Specific examples of the cyclic aliphatic hydrocarbon group include the same group as exemplified above for $Va^1$ in the aforementioned formula (a1-1).

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

In the cyclic aliphatic hydrocarbon group, part of the carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—.

Specific examples of the aromatic hydrocarbon group as a divalent hydrocarbon group include the same group as exemplified above for $Va^1$ in the aforementioned formula (a1-1).

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is most desirable.

As the alkoxy group, the halogen atom and the halogenated alkyl group for the substituent, the same groups as the aforementioned substituent groups for substituting a hydrogen atom within the cyclic aliphatic hydrocarbon group can be used.

(Divalent Linking Group Containing a Hetero Atom)

With respect to a divalent linking group containing a hetero atom, a hetero atom is an atom other than carbon and hydrogen, and examples thereof include an oxygen atom, a nitrogen atom, a sulfur atom and a halogen atom.

In the case where $Ya^{21}$ represents a divalent linking group containing a hetero atom, preferable examples of the linking group include —O—, —C(=O)—O—, —C(=O)—, —O—C(=O)—O—, —C(=O)—NH—, —NH— and —NH—C(=NH)— (wherein H may be substituted with a substituent such as an alkyl group or an acyl group), —S—, —S(=O)$_2$—, —S(=O)$_2$—O—, and a group represented by general formula —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m'}$—$Y^{22}$— or —$Y^{21}$—O—C(=O)—$Y^{22}$— [in the formulas, each of $Y^{21}$ and $Y^{22}$ independently represents a divalent hydrocarbon group which may have a substituent, O represents an oxygen atom, and m' represents an integer of 0 to 3].

When the divalent linking group containing a hetero atom represents —C(=O)—NH—, —NH—, or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In formula $Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m'}$—$Y^{22}$ or —$Y^{21}$—O—C(=O)—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m'}$—$Y^{22}$—, m' represents an integer of 0 to 3, preferably an integer of 0 to 2, more preferably 0 or 1, and particularly preferably 1. Namely, it is particularly desirable that the group represented by the formula —[$Y^{21}$—C(=O)—O]$_{m'}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

In the present invention, Ya$^{21}$ preferably represents an ester bond [—C(=O)—O—], an ether bond (—O—), a linear or branched alkylene group, a combination of these, or a single bond.

In the formula (a2-1), Ra$^{21}$ represents a lactone-containing cyclic group, a carbonate-containing cyclic group or an —SO$_2$— containing cyclic group.

The term "lactone-containing cyclic group" refers to a cyclic group including a ring containing a —O—C(=O)— structure (lactone ring). The term "lactone ring" refers to a single ring containing a —O—C(=O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for Ra$^{21}$ is not particularly limited, and an arbitrary structural unit may be used. Specific examples include groups represented by general formulas (a2-r-1) to (a2-r-7) shown below. Hereafter, "*" represents a valence bond.

[Chemical Formula 17]

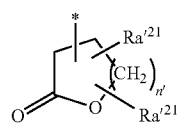
(a2-r-1)

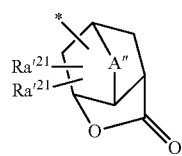
(a2-r-2)

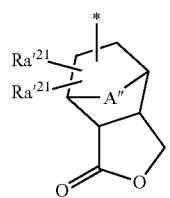
(a2-r-3)

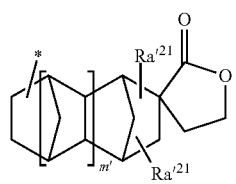
(a2-r-4)

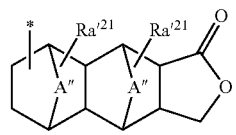
(a2-r-5)

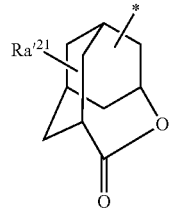
(a2-r-6)

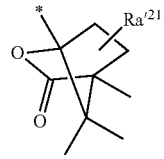
(a2-r-7)

In the formulas, each Ra$'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; n' represents an integer of 0 to 2; and m' represents 0 or 1.

In general formulas (a2-r-1) to (a2-r-7), A" represents an oxygen atom, a sulfonyl group or an alkylene group of 1 to 5 carbon atoms which may contain an oxygen atom (—O—) or a sulfur atom (—S—). As the alkylene group of 1 to 5 carbon atoms for A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—. As A", an alkylene group of 1 to 5 carbon atoms or —O— is preferable, more preferably an alkylene group of 1 to 5 carbon atoms, and most preferably a methylene group. Each Ra$'^{21}$ independently represents an alkyl group, an alkoxy group, a halogen atom, a halogenated alkyl group, —COOR", —OC(=O)R", a hydroxyalkyl group or a cyano group.

The alkyl group for Ra$'^{21}$ is preferably an alkyl group of 1 to 5 carbon atoms.

The alkoxy group for Ra$'^{21}$ is preferably an alkoxy group of 1 to 6 carbon atoms.

Further, the alkoxy group is preferably a linear or branched alkoxy group. Specific examples of the alkoxy groups include the aforementioned alkyl groups for Ra$'^{21}$ having an oxygen atom (—O—) bonded thereto.

As examples of the halogen atom for Ra$'^{21}$, a fluorine atom, chlorine atom, bromine atom and iodine atom can be given. Among these, a fluorine atom is preferable.

Examples of the halogenated alkyl group for Ra$'^{21}$ include groups in which part or all of the hydrogen atoms within the aforementioned alkyl groups for Ra$'^{21}$ has been substituted with the aforementioned halogen atoms. As the halogenated alkyl group, a fluorinated alkyl group is preferable, and a perfluoroalkyl group is particularly desirable.

Specific examples of the groups represented by the aforementioned general formulas (a2-r-1) to (a2-r-7) are shown below.

[Chemical Formula 18]

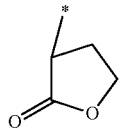
(r-lc-1-1)

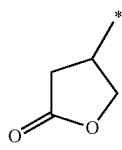
(r-lc-1-2)

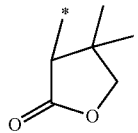
(r-lc-1-3)

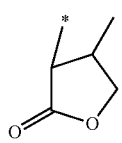
(r-lc-1-4)

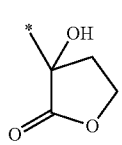
(r-lc-1-5)

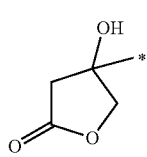
(r-lc-1-6)

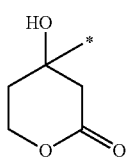
(r-lc-1-7)

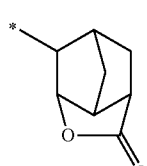
(r-lc-2-1)

(r-lc-2-2)

-continued

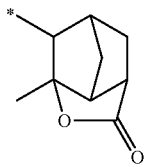
(r-lc-2-3)

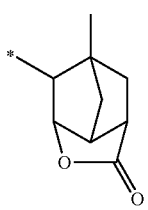
(r-lc-2-4)

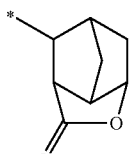
(r-lc-2-5)

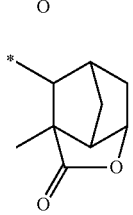
(r-lc-2-6)

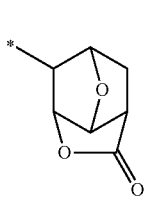
(r-lc-2-7)

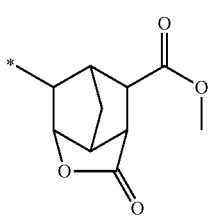
(r-lc-2-8)

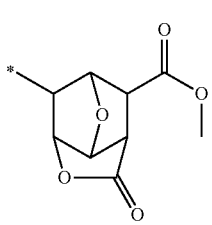
(r-lc-2-9)

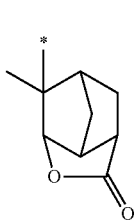
(r-lc-2-10)

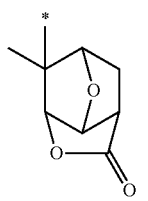
(r-lc-2-11)
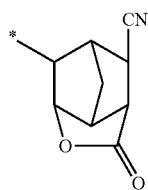
(r-lc-2-12)
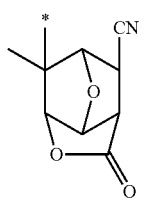
(r-lc-2-13)
[Chemical Formula 19]
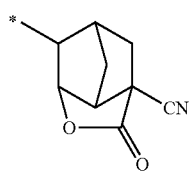
(r-lc-2-1-1)
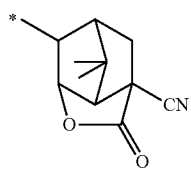
(r-lc-2-2-1)
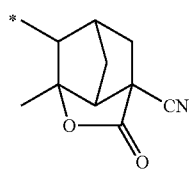
(r-lc-2-3-1)
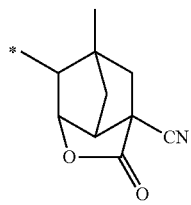
(r-lc-2-4-1)
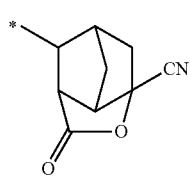
(r-lc-2-5-1)
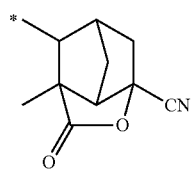
(r-lc-2-6-1)
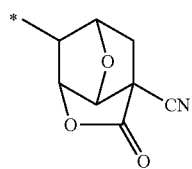
(r-lc-2-7-1)
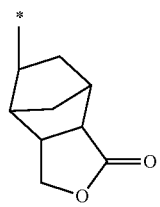
(r-lc-3-1)
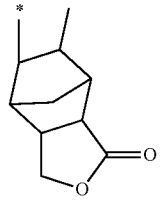
(r-lc-3-2)
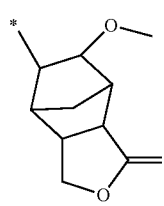
(r-lc-3-3)
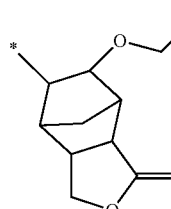
(r-lc-3-4)
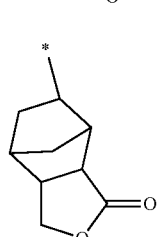
(r-lc-3-5)
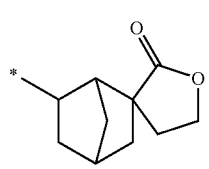
(r-lc-4-1)

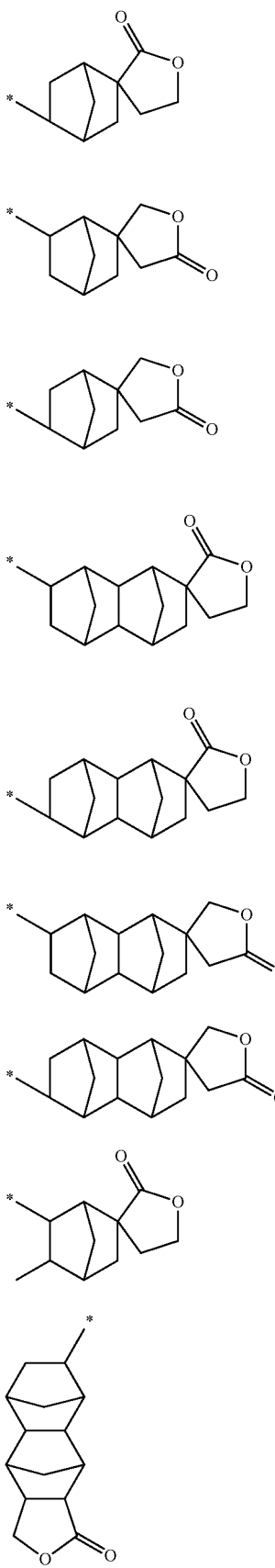
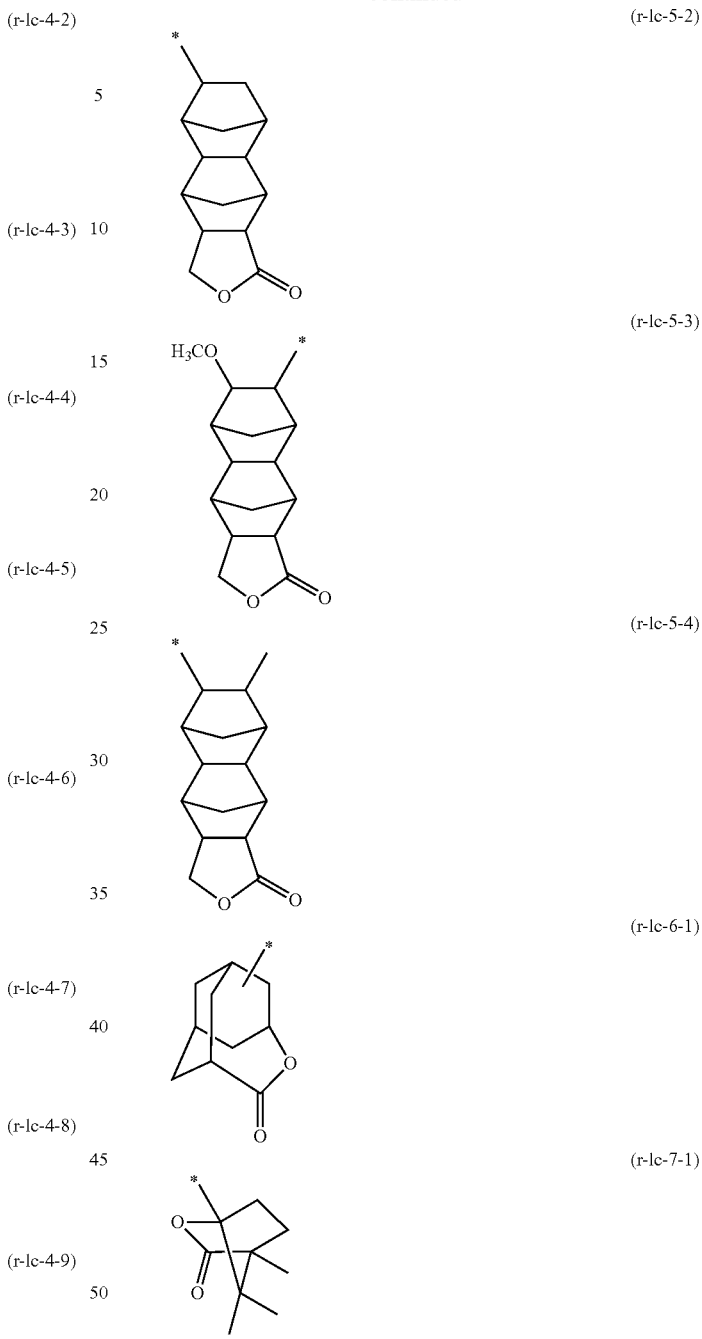

An "—SO₂— containing cyclic group" refers to a cyclic group having a ring containing —SO₂— within the ring structure thereof, i.e., a cyclic group in which the sulfur atom (S) within —SO₂— forms part of the ring skeleton of the cyclic group. The ring containing —SO₂— within the ring skeleton thereof is counted as the first ring. A cyclic group in which the only ring structure is the ring that contains —SO₂— in the ring skeleton thereof is referred to as a monocyclic group, and a group containing other ring structures is described as a polycyclic group regardless of the structure of the other rings. The —SO₂— containing cyclic group may be either a monocyclic group or a polycyclic group.

As the —SO₂— containing cyclic group as a cyclic hydrocarbon group for Ra[21], a cyclic group containing —O—SO₂— within the ring skeleton thereof, i.e., a cyclic group containing a sultone ring in which —O—S— within the —O—SO₂— group forms part of the ring skeleton thereof is particularly desirable. More specific examples of the —SO₂— containing cyclic group include groups represented by general formulas (a5-r-1) to (a5-r-4) shown below.

[Chemical Formula 20]

(a5-r-1)
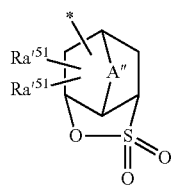

(a5-r-2)
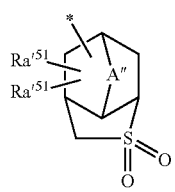

(a5-r-3)
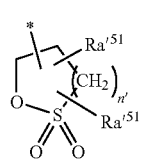

(a5-r-4)
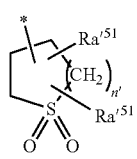

In the formulas, each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; and n' represents an integer of 0 to 2.

In general formulas (a5-r-1) to (a5-r-4), A" is the same as defined for A" in general formulas (a2-r-1) to (a2-r-7). Examples of the alkyl group, alkoxy group, halogen atom, halogenated alkyl group, —COOR", —OC(=O)R" and hydroxyalkyl group for $Ra'^{51}$ include the same groups as those described above in the explanation of $Ra'^{21}$ in the general formulas (a2-r-1) to (a2-r-7).

Specific examples of the groups represented by the aforementioned general formulas (a5-r-1) to (a5-r-4) are shown below. In the formulas shown below, "Ac" represents an acetyl group.

[Chemical Formula 21]

(r-sl-1-1)
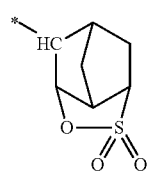

(r-sl-1-2)
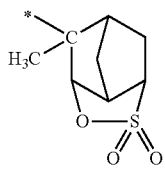

(r-sl-1-3)
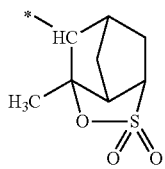

(r-sl-1-4)
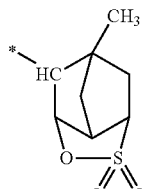

(r-sl-1-5)
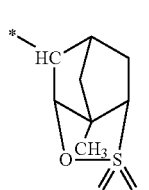

(r-sl-1-6)
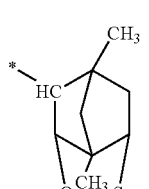

(r-sl-1-7)
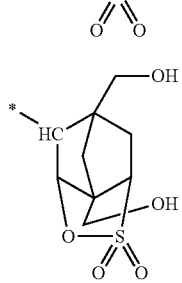

(r-sl-1-8)
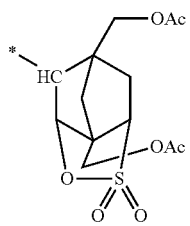

(r-sl-1-9)
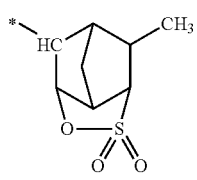

(r-sl-1-10)
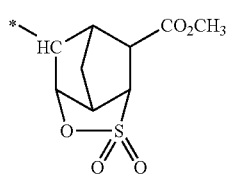
(r-sl-1-11)
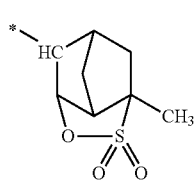
(r-sl-1-12)
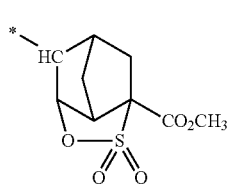
(r-sl-1-13)
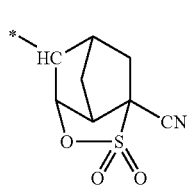
(r-sl-1-14)
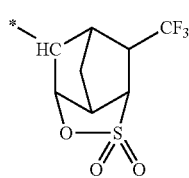
(r-sl-1-15)
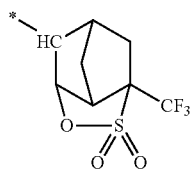
(r-sl-1-16)
(r-sl-1-17)
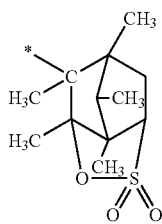
(r-sl-1-18)
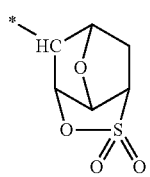
(r-sl-1-19)
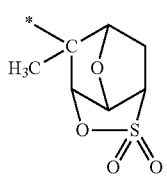
(r-sl-1-20)
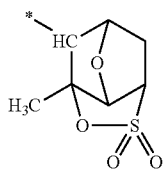
(r-sl-1-21)
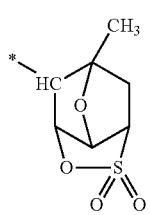
[Chemical Formula 22]
(r-sl-1-22)
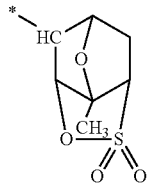
(r-sl-1-23)
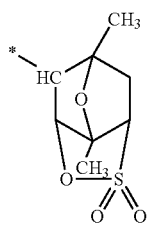
(r-sl-1-24)
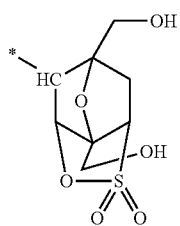

-continued (r-sl-1-25) 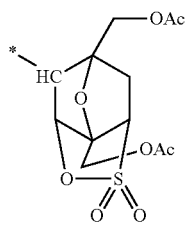

(r-sl-1-26) 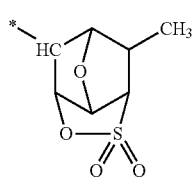

(r-sl-1-27) 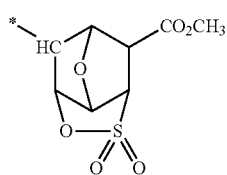

(r-sl-1-28) 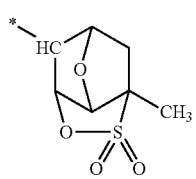

(r-sl-1-29) 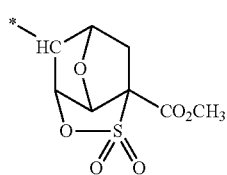

(r-sl-1-30) 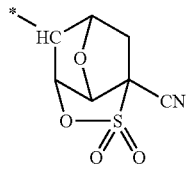

(r-sl-1-31) 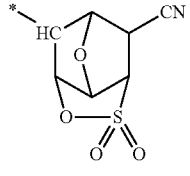

(r-sl-1-32) 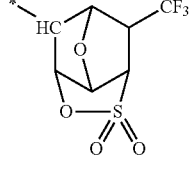

-continued (r-sl-1-33) 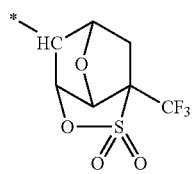

[Chemical Formula 23]

(r-sl-2-1) 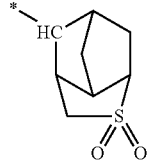

(r-sl-2-2) 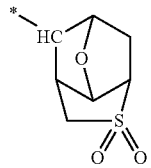

(r-sl-3-1) 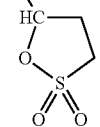

(r-sl-4-1) 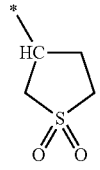

As the —$SO_2$— containing cyclic group, a group represented by the aforementioned general formula (a5-r-1) is preferable, at least one member selected from the group consisting of groups represented by the aforementioned chemical formulas (r-sl-1-1), (r-sl-1-18), (r-sl-3-1) and (r-sl-4-1) is more preferable, and a group represented by chemical formula (r-sl-1-1) is most preferable.

The term "carbonate-containing cyclic group" refers to a cyclic group including a ring containing a —O—C(=O)—O— structure (carbonate ring) in the ring skeleton thereof. The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group for $Ra^{21}$ as a cyclic hydrocarbon group is not particularly limited, and an arbitrary structural unit may be used. Specific examples include groups represented by general formulas (ax3-r-1) to (ax3-r-3) shown below.

[Chemical Formula 24]

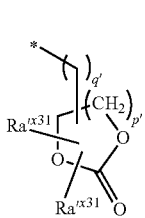 (ax3-r-1)

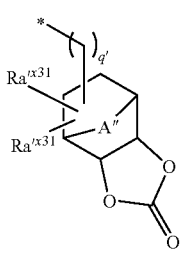 (ax3-r-2)

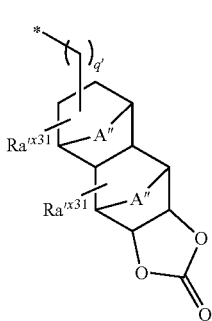 (ax3-r-3)

In the formulas, each $Ra'^{x31}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulas (ax3-r-1) to (ax3-r-3), A" is the same as defined for A" in general formula (a2-r-1).

Examples of the alkyl group, alkoxy group, halogen atom, halogenated alkyl group, —COOR", —OC(=O)R" and hydroxyalkyl group for $Ra'^{31}$ include the same groups as those described above in the explanation of $Ra'^{21}$ in the general formulae (a2-r-1) to (a2-r-7).

Specific examples of the groups represented by the aforementioned general formulas (ax3-r-1) to (ax3-r-3) are shown below.

[Chemical Formula 25]

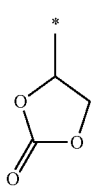 (r-cr-1-1)

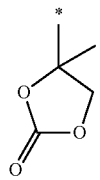 (r-cr-1-2)

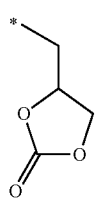 (r-cr-1-3)

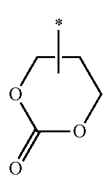 (r-cr-1-4)

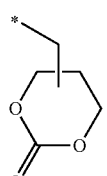 (r-cr-1-5)

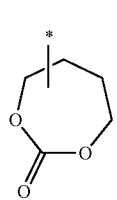 (r-cr-1-6)

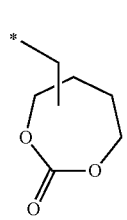 (r-cr-1-6)

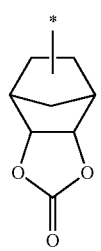 (r-cr-2-1)

(r-cr-2-2)
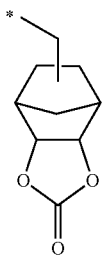

(r-cr-2-3)
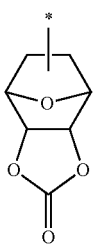

(r-cr-2-4)
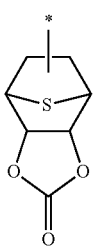

(r-cr-3-1)
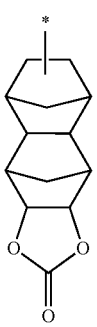

(r-cr-3-2)
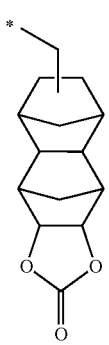

(r-cr-3-3)
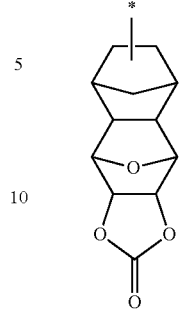

(r-cr-3-4)
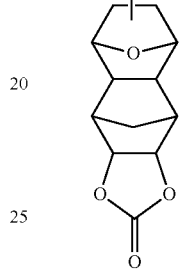

(r-cr-3-5)
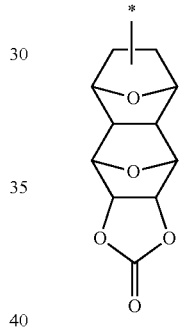

Among the examples shown above, a lactone-containing cyclic group or an —SO$_2$-containing cyclic group is preferable, a group represented by the general formula (a2-r-1), (a2-r-2) or (a5-r-1) is more preferable, and a group represented by any one of the chemical formulas (r-lc-1-1) to (r-lc-1-7), (r-lc-2-1) to (r-lc-2-13), (r-sl-1-1) and (r-sl-1-18) is still more preferable.

As the structural unit (a2) contained in the component (A1), 1 type of structural unit may be used, or 2 or more types may be used.

When the component (A1) contains the structural unit (a2), the amount of the structural unit (a2) based on the combined total of all structural units constituting the component (A1) is preferably 1 to 80 mol %, more preferably 5 to 70 mol %, still more preferably 10 to 65 mol %, and particularly preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties such as DOF and CDU and pattern shape can be improved.

(Structural Unit (a3))

The structural unit (a3) is a structural unit containing a polar group-containing aliphatic hydrocarbon group (provided that the structural units that fall under the definition of structural units (a1), (a0) and (a2) are excluded).

When the component (A1) includes the structural unit (a3), it is presumed that the hydrophilicity of the component (A1) is enhanced, thereby contributing to improvement in resolution.

Examples of the polar group include a hydroxyl group, a cyano group, a carboxyl group, or a hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups may be either monocyclic or polycyclic, and can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that includes an aliphatic polycyclic group that contains a hydroxyl group, a cyano group, a carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, a group in which two or more hydrogen atoms have been removed from adamantane, a group in which two or more hydrogen atoms have been removed from norbornane or a group in which two or more hydrogen atoms have been removed from tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulae (a3-1), (a3-2) and (a3-3) shown below are preferable.

[Chemical Formula 26]

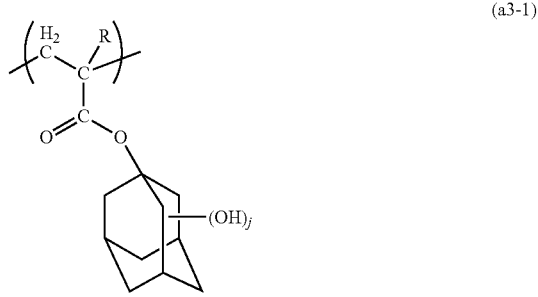
(a3-1)

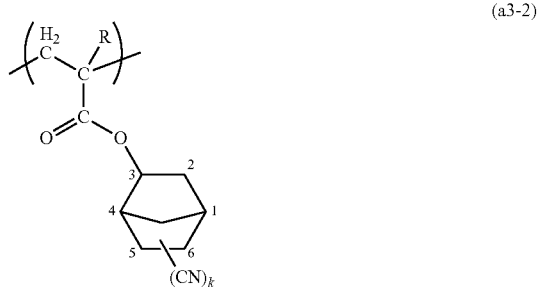
(a3-2)

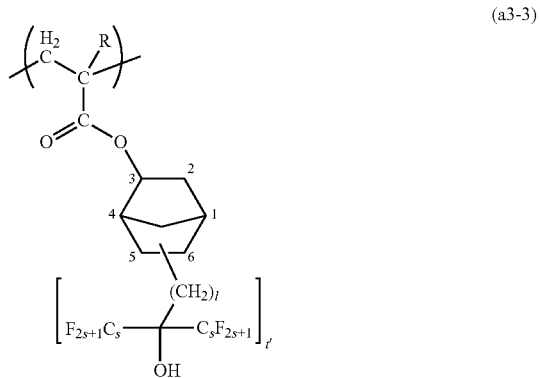
(a3-3)

In the formulae, R is as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 type of structural unit may be used, or 2 or more types may be used.

The amount of the structural unit (a3) within the component (A1) based on the combined total of all structural units constituting the component (A1) is preferably 5 to 50 mol %, more preferably 5 to 40 mol %, and still more preferably 5 to 25 mol %.

When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Structural Unit (a4))

The structural unit (a4) is a structural unit containing an acid non-dissociable cyclic group. When the component (A1) includes the structural unit (a4), dry etching resistance of the resist pattern to be formed is improved. Further, the hydrophobicity of the component (A1) is further improved. Increase in the hydrophobicity contributes to improvement in terms of resolution, shape of the resist pattern and the like, particularly in an organic solvent developing process.

In the structural unit (a4), an "acid non-dissociable, aliphatic cyclic group" refers to a cyclic group which is not dissociated by the action of the acid generated from the component (B) upon exposure, and remains in the structural unit.

As the structural unit (a4), a structural unit which contains a non-acid-dissociable aliphatic cyclic group, and is also derived from an acrylate ester is preferable. Examples of this cyclic group include the same groups as those described above in relation to the aforementioned structural unit (a1), and any of the multitude of conventional groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may have a linear or branched alkyl group of 1 to 5 carbon atoms as a substituent.

Specific examples of the structural unit (a4) include units with structures represented by general formulas (a4-1) to (a4-7) shown below.

[Chemical Formula 27]

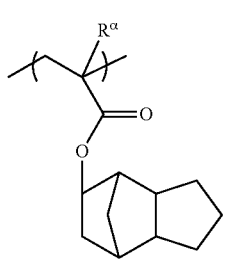

(a4-1)

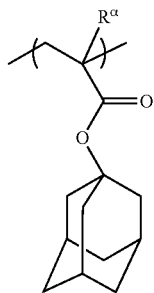

(a4-2)

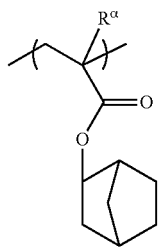

(a4-3)

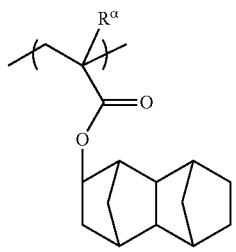

(a4-4)

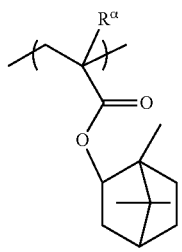

(a4-5)

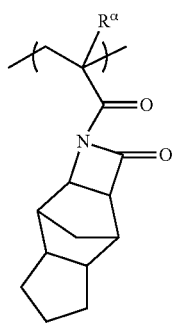

(a4-6)

-continued (a4-7)

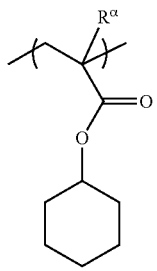

In the formulas shown above, $R^\alpha$ represents a hydrogen atom, a methyl group or a trifluoromethyl group.

As the structural unit (a4) contained in the component (A1), 1 type of structural unit may be used, or 2 or more types may be used.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

(Structural Unit (a9))

The structural unit (a9) is represented by general formula (a9-1) shown below.

[Chemical Formula 28]

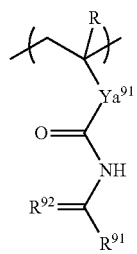

(a9-1)

In the formula, R is the same as defined above; $Ya^{91}$ represents a single bond or a divalent linking group; $R^{91}$ represents a hydrocarbon group which may have a substituent; and $R^{92}$ represents an oxygen atom or a sulfur atom.

In the formula (a9-1), the divalent linking group for $Ya^{91}$ is not particularly limited, and preferable examples thereof include a divalent hydrocarbon group which may have a substituent and a divalent linking group containing a hetero atom. As examples of the divalent linking group which may have a substituent and a divalent linking group containing a hetero atom for $Ya^{91}$, the same divalent linking groups which may have a substituent and divalent linking groups containing a hetero atom as those described above for the divalent linking group for $Ya^{21}$ can be given. $Ya^{91}$ is preferably a single bond.

In the formula (a9-1), as the hydrocarbon group for $R^{91}$, an alkyl group, a monovalent alicyclic hydrocarbon group, an aryl group and an aralkyl group can be mentioned.

The alkyl group for $R^{91}$ preferably has 1 to 8 carbon atoms, more preferably 1 to 6, and still more preferably 1 to 4, and may be either linear or branched. Specific examples include a methyl group, an ethyl group, a propyl group, a butyl group, a hexyl group and an octyl group.

The monovalent alicyclic hydrocarbon group for $R^{91}$ preferably has 3 to 20 carbon atoms and more preferably 3 to 12 carbon atoms, and may be either monocyclic or polycyclic. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic alicyclic hydrocarbon group, a group in which one or more hydrogen atoms have been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

The aryl group for $R^{91}$ preferably has 6 to 18 carbon atoms and more preferably 6 to 10 carbon atoms, and a phenyl group is particularly preferable.

Examples of the aralkyl group for $R^{91}$ include a group in which an alkylene group of 1 to 8 carbon atoms and the aforementioned "aryl group for $R^{91}$" are mutually bonded. An aralkyl group in which an alkylene group of 1 to 6 carbon atoms and the aforementioned "aryl group for $R^{91}$" are mutually bonded is preferable, and an aralkyl group in which an alkylene group of 1 to 4 carbon atoms and the aforementioned "aryl group for $R^{91}$" are mutually bonded is particularly preferable.

The hydrocarbon group for $R^{91}$ is preferably a group in which part or all of the hydrogen atoms within a hydrocarbon group has been substituted with a fluorine atom, and more preferably a group in which 30 to 100% of the hydrogen atoms within a hydrocarbon group have been substituted with fluorine atoms. Among these, a perfluoroalkyl group in which all of the hydrogen atoms within the alkyl group has been substituted with fluorine atoms is particularly preferable.

The hydrocarbon group for $R^{91}$ may have a substituent. Examples of the substituents include a halogen atom, an oxo group (=O), a hydroxy group (—OH), an amino group (—NH$_2$) and —SO$_2$—NH$_2$. In the hydrocarbon group, part of the carbon atoms constituting the hydrocarbon group may be substituted with a substituent containing a hetero atom. The substituent containing a hetero atom is preferably —O—, —NH—, —N=, —C(=O)—O—, —S—, —S(=O)$_2$—, or —S(=O)$_2$—O—.

Examples of the hydrocarbon group for $R^{91}$ having a substituent include lactone-containing cyclic groups represented by the general formulas (a2-r-1) to (a2-r-7), —SO$_2$-containing cyclic groups represented by the general formulas (a5-r-1) to (a5-r-4), a substituted aryl group and a monovalent heterocycles represented by chemical formulae shown below.

[Chemical Formual 29]

(r-ar-1)

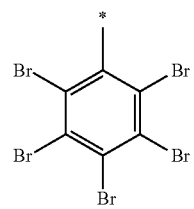

(r-ar-2) 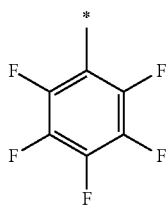
(r-ar-3) 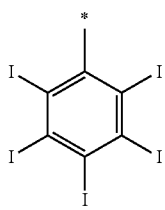
(r-ar-4) 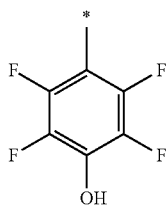
(r-ar-5) 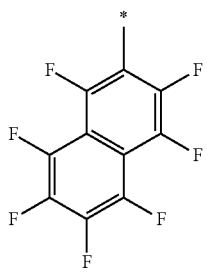
(r-ar-6) 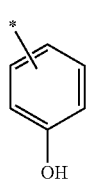
(r-ar-7) 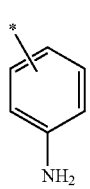
(r-ar-8) 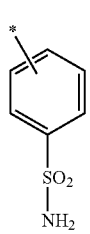
(r-hr-1) 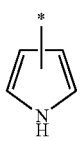
(r-hr-2) 
(r-hr-3) 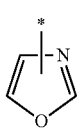
(r-hr-4) 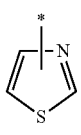
(r-hr-5) 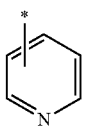
(r-hr-6) 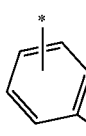
(r-hr-7) 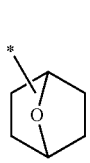
(r-hr-8) 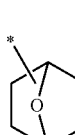
(r-hr-9) 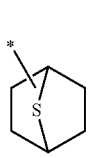
(r-hr-10) 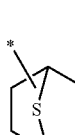
Specific examples of structural units represented by the general formula (a9-1) are shown below. In the formulas shown below, $R^\alpha$ represents a hydrogen atom, a methyl group or a trifluoromethyl group.

[Chemical Formula 30]

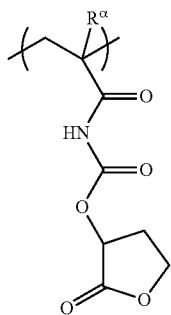 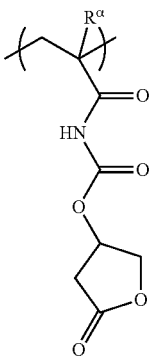 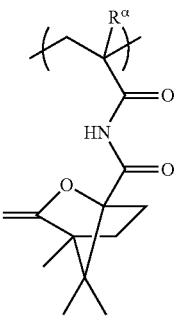 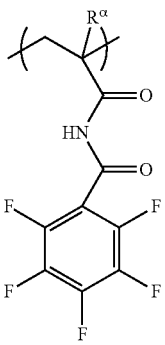

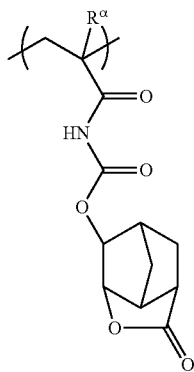 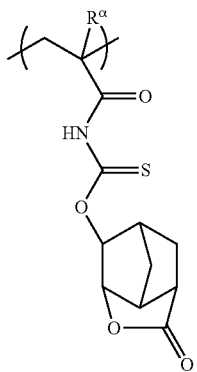

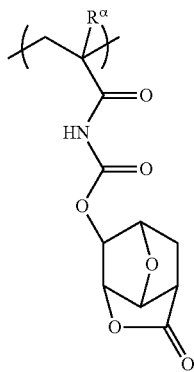 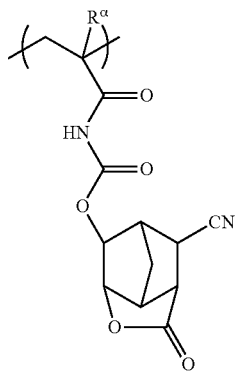

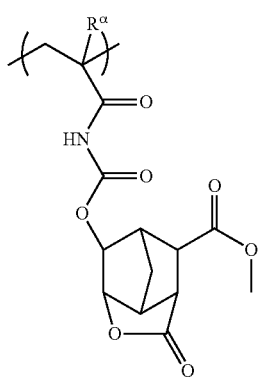 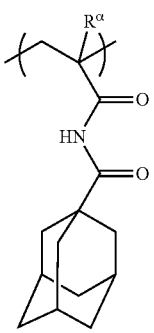

-continued

As the structural unit (a9) contained in the component (A1), 1 type of structural unit may be used, or 2 or more types may be used.

When the component (A1) includes the structural unit (a9), the amount of the structural unit (a9) based on the combined total of all structural units constituting the component (A1) is preferably 1 to 30 mol %, and more preferably 3 to 25 mol %. When the amount of the structural unit (a1) is at least as large as the lower limit of the above-mentioned range, various lithography properties such as development characteristics and EL margin are improved. On the other hand, when the amount of the structural unit (a9) is no more than the upper limit of the above-mentioned range, a good balance can be achieved with the other structural units.

The component (A1) is preferably a copolymer containing the structural unit (a1). As the copolymer having the structural unit (a1), a copolymer further having any one of the structural units (a2), (a3) and (a9) is preferable; a copolymer having the structural units (a1) and (a3), a copolymer having the structural units (a1) and (a2), a copolymer having the structural units (a1) and (a9), a copolymer having the structural units (a1), (a2) and (a3), and a copolymer having the structural units (a1), (a2) and (a9) are more preferable.

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A1) is not particularly limited, but is preferably 1.0 to 5.0, more preferably 1.0 to 3.0, and most preferably 1.2 to 2.5.

Here, Mn is the number average molecular weight.

As the component (A1), one type may be used alone, or two or more types may be used in combination.

In the base component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved, such as improvement in MEF and circularity, and reduction of roughness.

In the resist composition of the present invention, as the component (A), one type may be used, or two or more types may be used in combination.

In the resist composition of the present invention, the amount of the component (A) can be appropriately adjusted depending on the thickness of the resist film to be formed, and the like.

<Acid Generator Component; Component (B)>

The resist composition of the present invention preferably include an acid generator component (B) (hereafter, referred to as "component (B)") which generates acid upon exposure. As the component (B), there is no particular limitation, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. Among these, onium salt acid generators are preferably used.

Examples of the onium salt acid generators include a compound represented by general formula (b-1) shown below (hereafter, sometimes referred to as "component (b-1)"), a compound represented by general formula (b-2) shown below (hereafter, sometimes referred to as "component (b-2)") and a compound represented by general formula (b-3) shown below (hereafter, sometimes referred to as "component (b-3)").

[Chemical Formula 31]

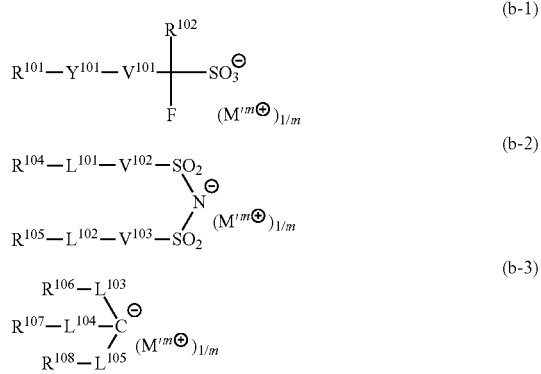

In the formulas, $R^{101}$ and $R^{104}$ to $R^{108}$ each independently represents a cyclic group which may have a substituent, a chain-like alkyl group which may have a substituent or a chain-like alkenyl group which may have a substituent, provided that, $R^{104}$ and $R^{105}$ may be mutually bonded to form a ring; provided that, two of $R^{106}$ to $R^{107}$ may be mutually bonded to form a ring; $R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; and $M^{'m+}$ represents an organic cation having a valency of m.

{Anion Moiety}—Anion Moiety of Component (b-1)

In the formula (b-1), $R^{101}$ represents a cyclic group which may have a substituent, a chain-like alkyl group which may have a substituent or a chain-like alkenyl group which may have a substituent.

(Cyclic Group which May have a Substituent)

The cyclic group is preferably a cyclic hydrocarbon group, and the cyclic hydrocarbon group may be either an aromatic hydrocarbon group or an aliphatic hydrocarbon group.

As the aromatic hydrocarbon group for $R^{101}$, groups in which one hydrogen atom has been removed from an aromatic hydrocarbon ring described above in relation to the divalent aromatic hydrocarbon group for $Va^1$ in the formula (a1-1) or an aryl group in which one hydrogen atom has been removed from an aromatic compound containing two or more aromatic ring can be mentioned, and a phenyl group or a naphthyl group is preferable.

As the cyclic aliphatic hydrocarbon group for $R^{101}$, groups in which one hydrogen atom has been removed from a monocycloalkane or a polycycloalkane exemplified above in the explanation of the divalent aliphatic hydrocarbon group for $Va^1$ in the formula (a1-1) can be mentioned, and an adamantyl group or a norbornyl group is preferable.

Further, the cyclic hydrocarbon group for $R^{101}$ may contain a hetero atom like as a heterocycle, and specific examples thereof include lactone-containing cyclic groups represented by the aforementioned general formulas (a2-r-1) to (a2-r-7), —SO$_2$— containing cyclic groups represented by the aforementioned formulas (a5-r-1) to (a5-r-4) and heterocycles shown below.

[Chemical Formula 32]

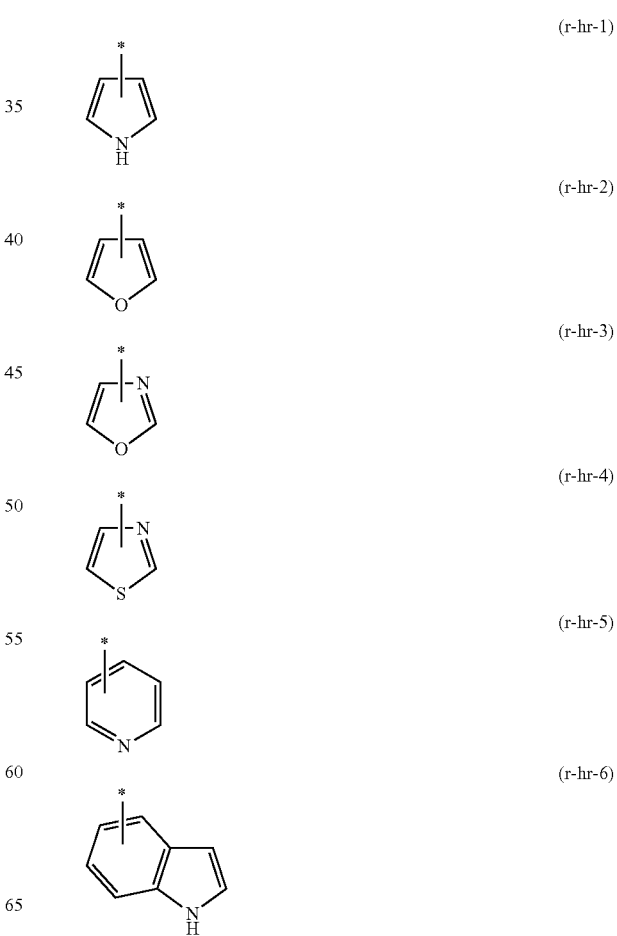

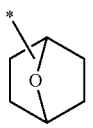
(r-hr-7)

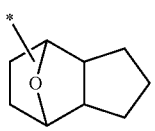
(r-hr-8)

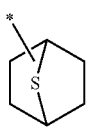
(r-hr-9)

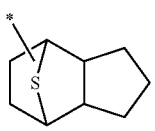
(r-hr-10)

(r-hr-11)

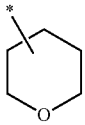
(r-hr-12)

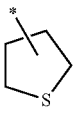
(r-hr-13)

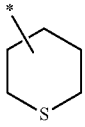
(r-hr-14)

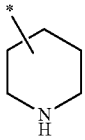
(r-hr-15)

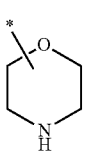
(r-hr-16)

As the substituent for substituting the cyclic hydrocarbon group for $R^{101}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent include a fluorine atom, a chlorine atom, a bromine atom and an iodine atom, and a fluorine atom is preferable.

Example of the halogenated alkyl group as a substituent includes a group in which a part or all of the hydrogen atoms within an alkyl group of 1 to 5 carbon atoms such as a methyl group, an ethyl group, a propyl group, an n-butyl group or a tert-butyl group have been substituted with the aforementioned halogen atoms.

(Chain-Like Alkyl Group which May have a Substituent)

The chain-like alkyl group for $R^{101}$ may be either linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

(Chain-Like Alkenyl Group which May have a Substituent)

The chain-like alkenyl group for $R^{101}$ may be linear or branched, and preferably has 2 to 10 carbon atoms, more preferably 2 to 5 carbon atoms, still more preferably 2 to 4 carbon atoms, and particularly preferably 3 carbon atoms. Examples of linear alkenyl groups include a vinyl group, a propenyl group (an allyl group) and a butynyl group. Examples of branched alkenyl groups include a 1-methylpropenyl group and a 2-methylpropenyl group.

Among the above-mentioned examples, as the chain-like alkenyl group, a propenyl group is particularly desirable.

As the substituent for substituting the chain-like alkyl group or alkenyl group for $R^{101}$, an alkoxy group, a halogen atom, a halogenated alkyl group, a hydroxyl group, a carbonyl group, a nitro group, an amino group, the same cyclic group as described above for $R^{101}$ or the like can be used.

Among these, as $R^{101}$, a cyclic group which may have a substituent is preferable, and a cyclic hydrocarbon group which may have a substituent is more preferable. Specific examples include a group in which one or more hydrogen atoms have been removed from a phenyl group, a naphthyl group or a polycycloalkane, lactone-containing cyclic groups represented by the formulas (a2-r-1) to (a2-r-7) and —$SO_2$— containing cyclic groups represented by the formulas (a5-r-1) to (a5-r-4) and the like.

In the formula (b-1), $R^{101}$ represents a single bond or a divalent linking group containing an oxygen atom.

In the case where $Y^{101}$ is a divalent linking group containing an oxygen atom, $Y^{101}$ r may contain an atom other than an oxygen atom. Examples of atoms other than an oxygen atom include a carbon atom, a hydrogen atom, a sulfur atom and a nitrogen atom.

Examples of divalent linkage groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amide bond (—C(=O)—NH—), a carbonyl group (—C(=O)—) and a carbonate group (—O—C(=O)—O—); and a combination of any of the aforementioned non-hydrocarbon, oxygen atom-containing linking groups with an alkylene group. Furthermore, the combinations may have a sulfonyl group (—SO$_2$—) bonded thereto. As the combination, the linking groups represented by formulae (y-al-1) to (y-al-7) shown below can be mentioned.

[Chemical Formula 33]

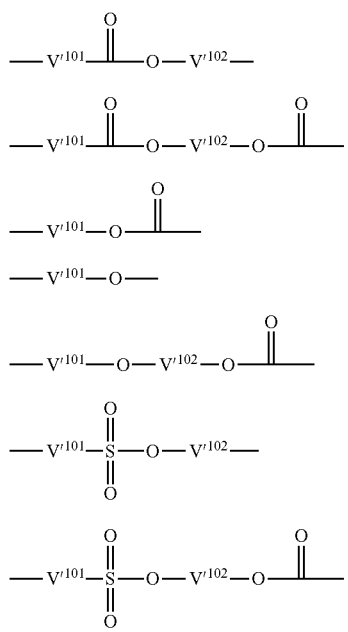

In the formulae, $V'^{101}$ represents a single bond or an alkylene group of 1 to 5 carbon atoms; and $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms.

As the alkylene group for $V'^{101}$ and $V'^{102}$, a linear alkylene group or a branched alkylene group can be used, and a linear alkylene group is preferable.

Specific examples of the alkylene group for $V'^{101}$ and $V'^{102}$ include a methylene group [—CH$_2$—]; alkylmethylene groups such as —CH(CH$_3$)—, —CH(CH$_2$CH$_3$)—, —C(CH$_3$)(CH$_2$CH$_3$)—, —C(CH$_3$)(CH$_2$CH$_2$CH$_3$)— and —C(CH$_2$CH$_3$)$_2$—; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$— and —CH$_2$CH(CH$_3$)CH$_2$—; a tetramethylene group [—CH$_2$CH$_2$CH$_2$CH$_2$—]; alkyltetramethylene groups such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

Further, part of methylene group within the alkylene group for $V'^{101}$ and $V'^{102}$ may be substituted with a divalent aliphatic cyclic group of 5 to 10 carbon atoms. The aliphatic cyclic group is preferably a divalent group in which one hydrogen atom has been removed from the cyclic aliphatic hydrocarbon group described above for $Ra'^3$ in the aforementioned formula (a1-r-1), and a cyclohexylene group, 1,5-adamantylene group or 2,6-adamantylene group is more preferable.

$Y^{101}$ is preferably a divalent linking group containing an ether bond or an ester bond, and linking groups represented by the aforementioned formulas (y-al-1) to (y-al-5) are preferable.

In the formula (b-1), $V^{101}$ represents a single bond, an alkylene group or a fluorinated alkylene group. The alkylene group or fluorinated alkylene group for $V^{101}$ preferably has 1 to 4 carbon atoms. As the fluorinated alkylene group for $V^{101}$, a group in which part or all of the hydrogen atoms within the aforementioned alkylene group for $V^{101}$ has been substituted with fluorine atoms can be used. Among these, $V^{101}$ is preferably a single bond or a fluorinated alkylene group of 1 to 4 carbon atoms.

In the formula (b-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and is more preferably a fluorine atom.

As specific examples of anion moieties of the formula (b-1),

When $Y^{101}$ is a single bond, fluorinated alkylsulfonate anions such as a trifluoromethanesulfonate anion or a perfluorobutanesulfonate anion can be mentioned; and when $Y^{101}$ is a divalent linking group containing an oxygen atom, anions represented by formulae (an-1) to (an-3) shown below can be mentioned.

[Chemical Formula 34]

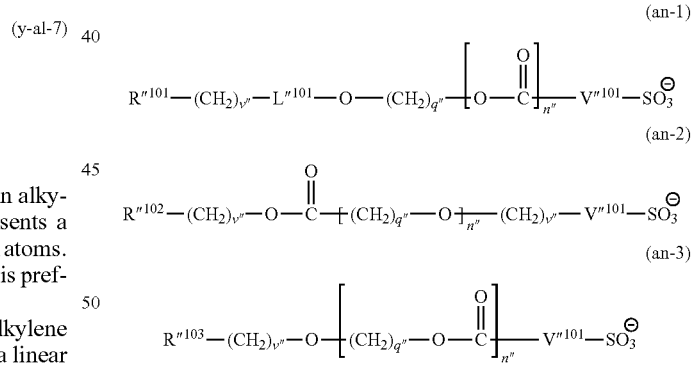

In the formulae, $R'''^{101}$ represents an aliphatic cyclic group which may have a substituent, a group represented by any one of the aforementioned formulae (r-hr-1) to (r-hr-6) or a chain-like alkyl group which may have a substituent; $R'''^{102}$ represents an aliphatic cyclic group which may have a substituent, a lactone-containing cyclic group represented by any one of the formulae (a2-r-1) to (a2-r-7) or an —SO$_2$— containing cyclic group represented by any one of the formulae (a5-r-1) to (a5-r-4); $R'''^{103}$ represents an aromatic cyclic group which may have a substituent, an aliphatic cyclic group which may have a substituent or a chain-like alkenyl group which may have a substituent; $V'''^{101}$ represents a fluorinated alkylene group; $L''^{101}$ represents —C(=O)— or —SO$_2$—; v" each independently represents an integer of 0 to 3; q" each independently represents an integer of 1 to 20; n" represents 0 or 1.

As the aliphatic cyclic group for $R''^{101}$, $R''^{102}$ and $R''^{103}$ which may have a substituent, the same groups as the cyclic aliphatic hydrocarbon group for $R^{101}$ described above are preferable. As the substituent, the same groups as those described above for substituting the cyclic aliphatic hydrocarbon group for $R^{101}$ can be mentioned.

As the aromatic cyclic group for $R''^{103}$ which may have a substituent, the same groups as the aromatic hydrocarbon group exemplified as a cyclic hydrocarbon group for $R^{101}$ described above are preferable. As the substituent, the same groups as those described above for substituting the aromatic hydrocarbon group for $R^{101}$ can be mentioned.

As the chain-like alkyl group for $R''^{101}$ which may have a substituent, the same groups exemplified as the chain-like alkyl group for $R^{101}$ are preferable. As the chain-like alkenyl group for $R''^{103}$ which may have a substituent, the same groups exemplified as the chain-like alkenyl group for $R^{101}$ are preferable. $V''^{101}$ is preferably a fluorinated alkylene group of 1 to 3 carbon atoms, and particularly preferably —$CF_2$—, —$CF_2CF_2$—, —$CHFCF_2$—, —$CF(CF_3)CF_2$— or —$CH(CF_3)CF_2$—.

Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and is the same groups as those defined above for $R^{101}$ in the aforementioned formula (b-1), provided that, $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, preferably 1 to 7, and more preferably 1 to 3. The smaller the number of carbon atoms of the chain-like alkyl group for $R^{104}$ and $R^{105}$ within the above-mentioned range of the number of carbon atoms, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved. The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same groups as those defined above for $V^{101}$ in the aforementioned formula (b-1).

In the formula (b-2), $L^{101}$ and $L^{102}$ each independently represents a single bond or an oxygen atom.

Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same groups as those defined above for $R^{101}$ in the aforementioned formula (b-1).

$L^{103}$ to $L^{105}$ each independently represents a single bond, —CO— or —$SO_2$—.

{Cation Moiety}

In the formulas (b-1), (b-2) and (b-3), $M'^{m+}$ represents an organic cation having a valency of m. Among these, a sulfonium cation or an iodonium cation is preferable, and cation moieties represented by general formulae (ca-1) to (ca-4) shown below are particularly preferable.

[Chemical Formula 35]

(ca-1)

(ca-2)

(ca-3)

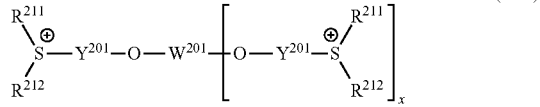

(ca-4)

In the formulas, each of $R^{201}$ to $R^{207}$, $R^{211}$ and $R^{212}$ independently represents an aryl group which may have a substituent, an alkyl group which may have a substituent or an alkenyl group which may have a substituent; $R^{201}$ to $R^{203}$, $R^{206}$ and $R^{207}$, and $R^{211}$ and $R^{212}$ may be mutually bonded to form a ring with the sulfur atom; $R^{208}$ and $R^{209}$ each represents a hydrogen atom or an alkyl group of 1 to 5 carbon atoms; $R^{210}$ represents an aryl group which may have a substituent, an alkyl group which may have a substituent, an alkenyl group which may have a substituent or an —$SO_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$, an unsubstituted aryl group of 6 to 20 carbon atoms can be mentioned, and a phenyl group or a naphthyl group is preferable.

As the alkyl group for $R^{201}$ to $R^{207}$, $R^{211}$ and $R^{212}$, a chain-like or cyclic alkyl group of 1 to 30 carbon atoms is preferable.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$, $R^{211}$ and $R^{212}$ may have include an alkyl group, a halogen atom, a halogenated alkyl group, a carbonyl group, a cyano group, an amino group, an aryl group, an arylthio group and groups represented by formulas (ca-r-1) to (ca-r-7) shown below.

As the aryl group within the arylthio group as a substituent, the same aryl groups as those described above for $R^{101}$ can be mentioned, and specific examples thereof include a pheylthio group or a biphenylthio group.

[Chemical Formula 36]

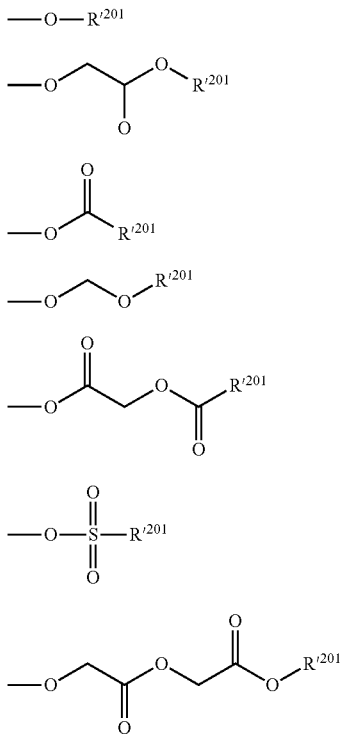

[ca-r-1]
[ca-r-2]
[ca-r-3]
[ca-r-4]
[ca-r-5]
[ca-r-6]
[ca-r-7]

In the formulae, $R'^{201}$ each independently represents a hydrogen atom, a cyclic group which may have a substituent, a chain-like alkyl group which may have a substituent or a chain-like alkenyl group which may have a substituent.

As the cyclic group which may have a substituent, the chain-like alkyl group which may have a substituent and the chain-like alkenyl group which may have a substituent for $R'^{201}$, the same groups as those described above for $R^{101}$ in the aforementioned formula (b-1) can be mentioned. As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$ and $R^{207}$, and $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group of 1 to 5 carbon atoms). As the ring to be formed, the ring containing the sulfur atom in the skeleton thereof is preferably a 3 to 10-membered ring, and particularly preferably a 5 to 7-membered ring. Examples of the formed ring include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring and a tetrahydrothiopyranium ring.

$R^{208}$ and $R^{209}$ each independently represents a hydrogen atom or an alkyl group of 1 to 5 carbon atoms, is preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent or an —SO$_2$-containing cyclic group which may have a substituent.

As the aryl group for $R^{210}$, an unsubstituted aryl group of 6 to 20 carbon atoms can be mentioned, and a phenyl group or a naphthyl group is preferable.

As the alkyl group for $R^{210}$, a chain-like or cyclic alkyl group of 1 to 30 carbon atoms is preferable.

The alkenyl group for $R^{210}$ preferably has 2 to 10 carbon atoms.

As the —SO$_2$— containing cyclic group for $R^{210}$ which may have a substituent, the same groups as the "—SO$_2$— containing cyclic group" for Ra$^{21}$ in the general formula (a2-1) can be mentioned, and the group represented by the aforementioned general formula (a5-r-1) is preferable.

$Y^{201}$ each independently represents an arylene group, an alkylene group or an alkenylene group.

As the arylene group for $Y^{201}$, a group in which one hydrogen atom has been removed from an aryl group exemplified as an aromatic hydrocarbon group for $R^{101}$ in the aforementioned formula (b-1) can be mentioned.

As the alkylene group and the alkenylene group for $Y^{201}$, the same aliphatic hydrocarbon group as those described above for the divalent hydrocarbon group for Va$^1$ in the aforementioned general formula (a1-1) can be mentioned.

In the formula (ca-4), x represents 1 or 2.

$W^{201}$ represents a linking group having a valency of (x+1), that is, a divalent or trivalent linking group.

As the divalent linking group for $W^{201}$, a divalent hydrocarbon groups which may have a substituent is preferable, and as examples thereof, the same hydrocarbon group as those described above for Ya$^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. As the arylene group, a phenylene group and a naphthylene group can be mentioned. Of these, a phenylene group is particularly desirable.

As the trivalent linking group for $W^{201}$, a group in which one hydrogen atom has been removed from the aforementioned divalent linking group for $W^{201}$, and a group in which the divalent linking group has been bonded to an another divalent linking group can be mentioned. The trivalent linking group for $W^{201}$ is preferably an arylene group having two carbonyl groups bonded thereto.

Specific examples of preferable cations represented by formula (ca-1) include cations represented by formulas (ca-1-1) to (ca-1-63) shown below.

[Chemical Formula 37]

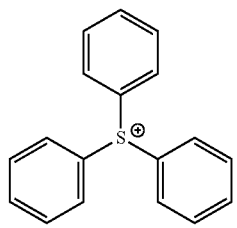

(ca-1-1)

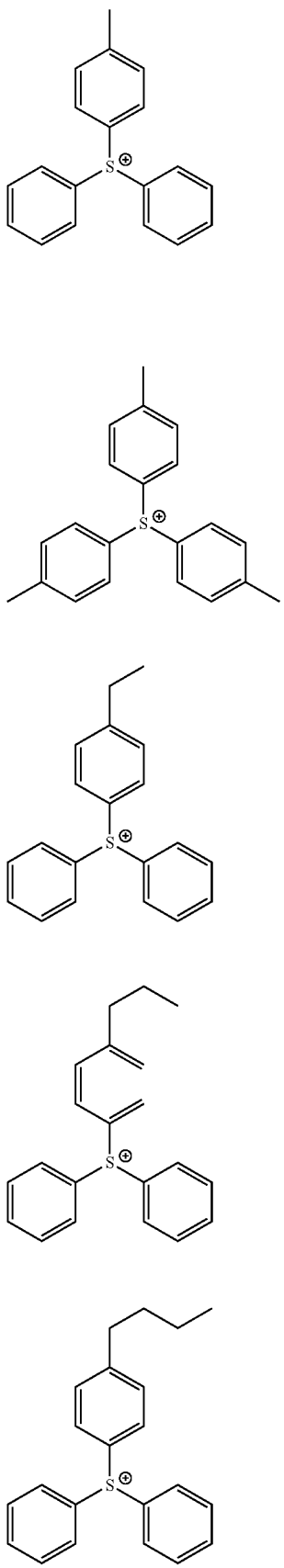
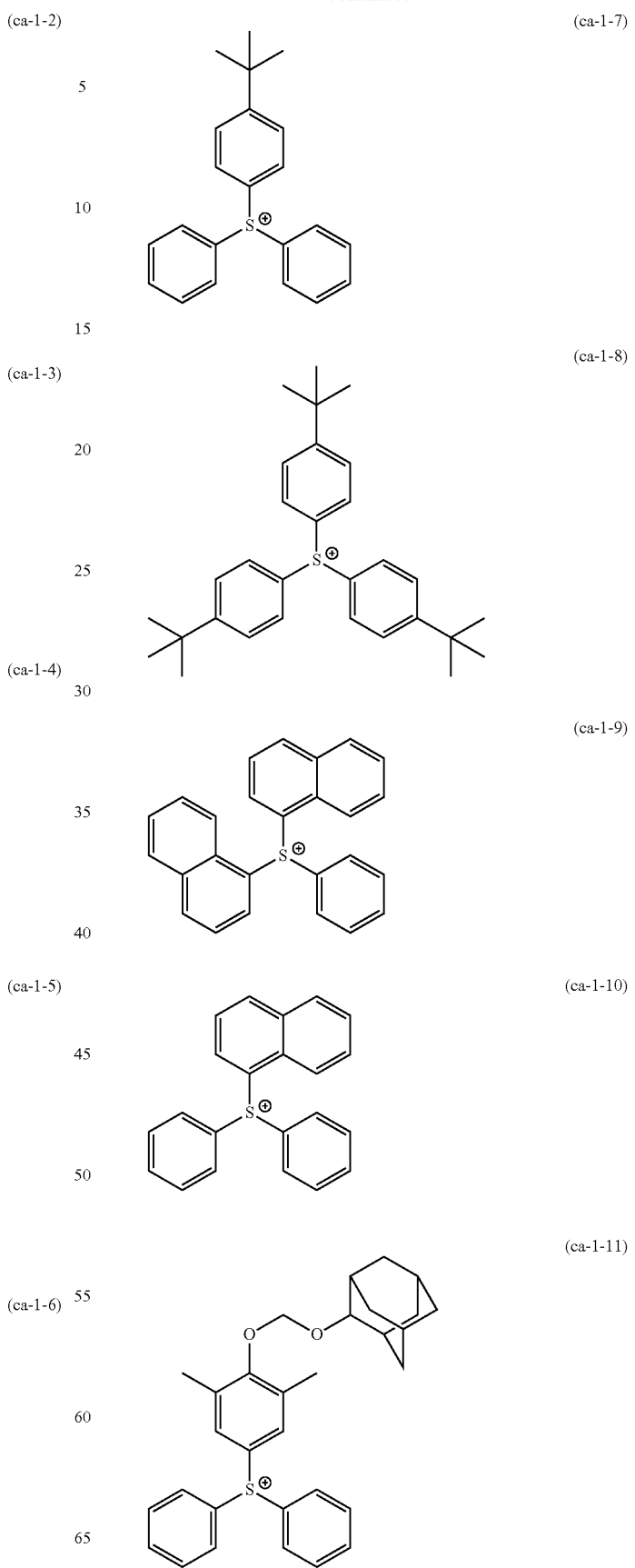

(ca-1-12) 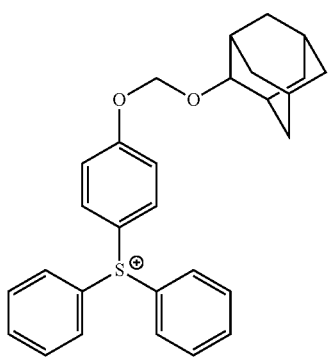
(ca-1-16) 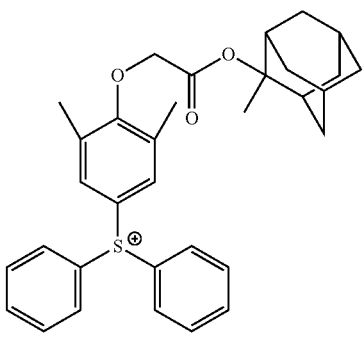
[Chemical Formula 38]
(ca-1-13) 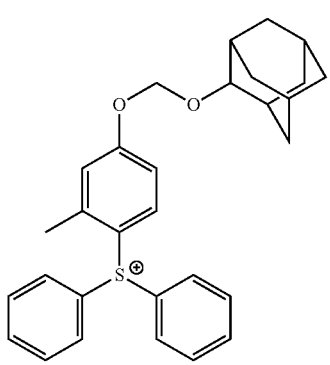
(ca-1-17) 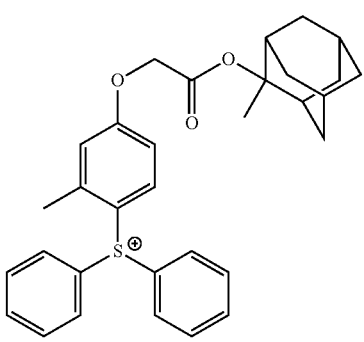
(ca-1-14) 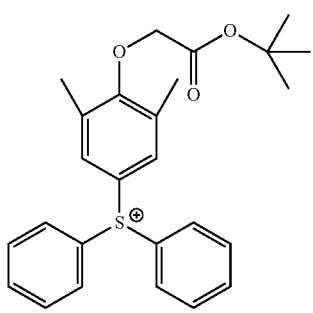
(ca-1-18) 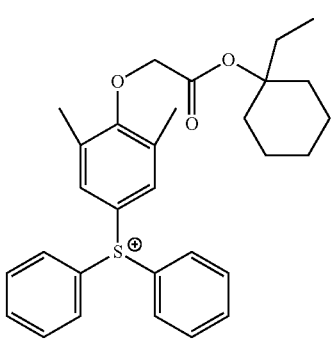
(ca-1-15) 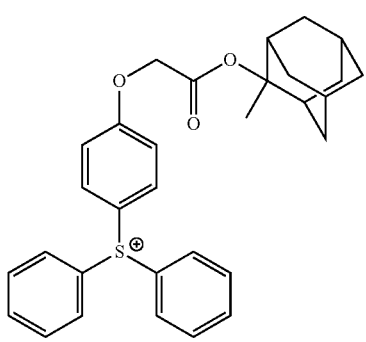
(ca-1-19) 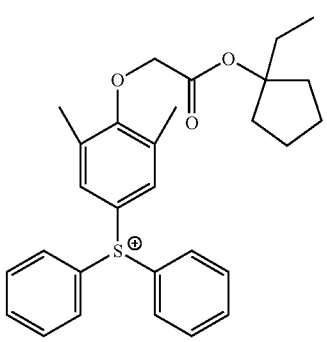

(ca-1-20) 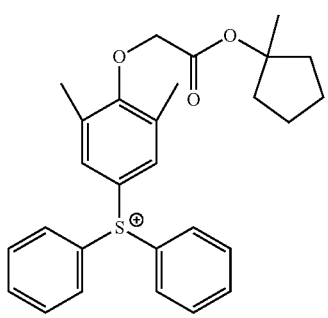
(ca-1-21) 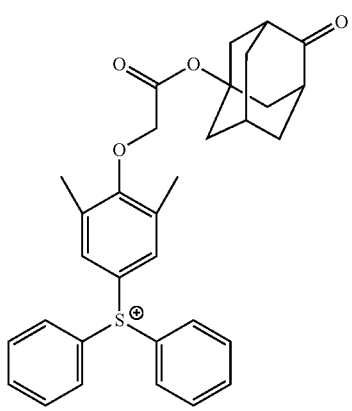
(ca-1-22) 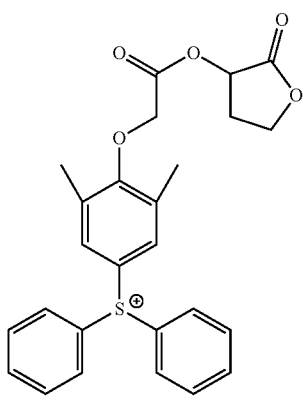
(ca-1-23) 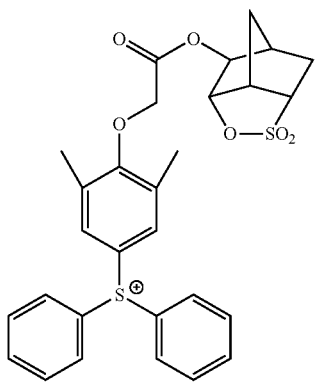
(ca-1-24) 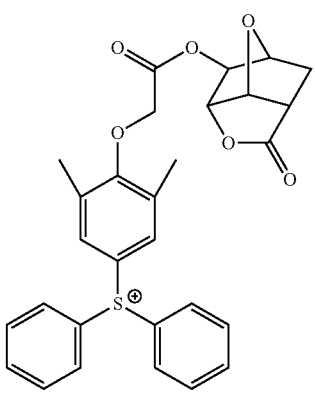
(ca-1-25) 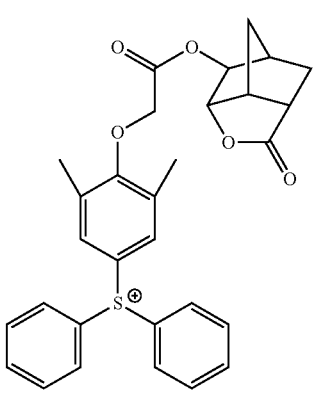
(ca-1-26) 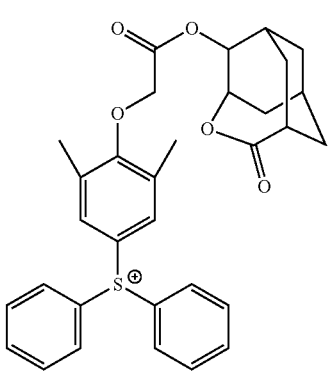
(ca-1-27) 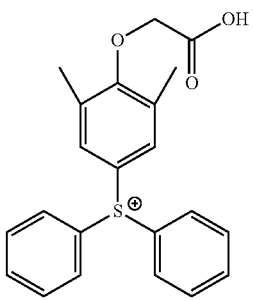

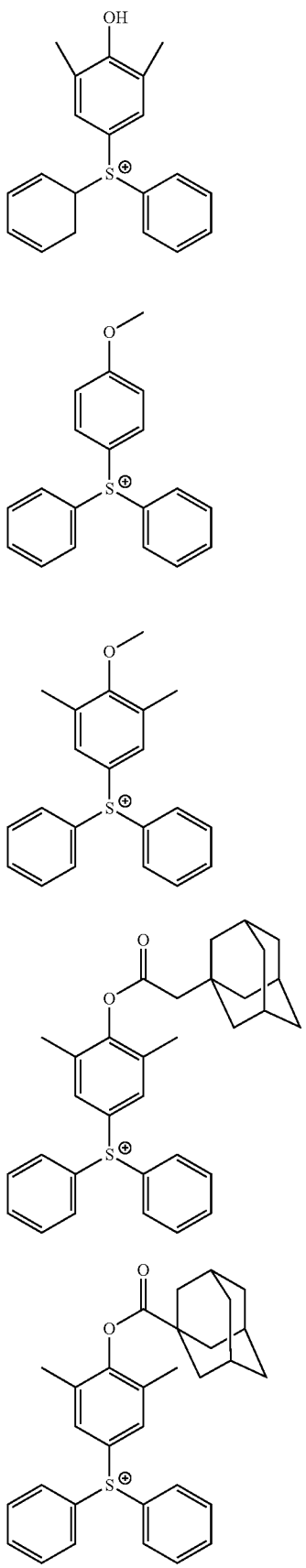
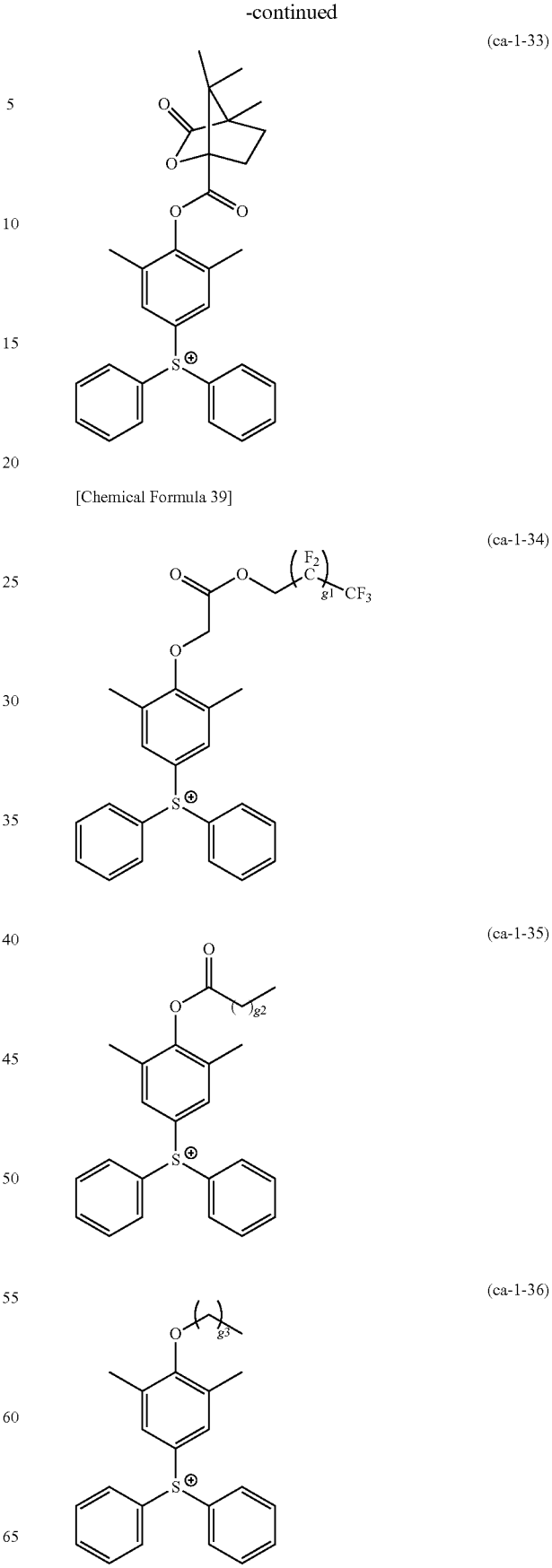

(ca-1-37)
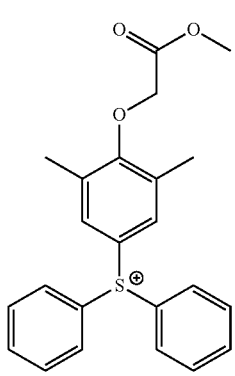
(ca-1-38)
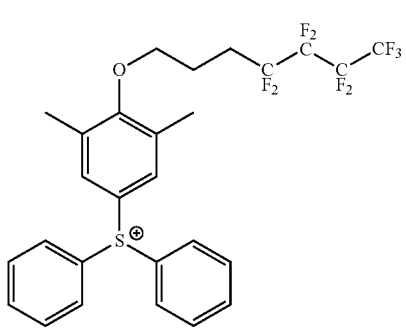
(ca-1-39)
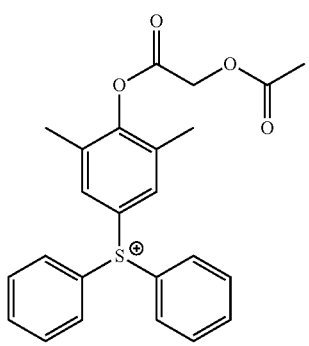
(ca-1-40)
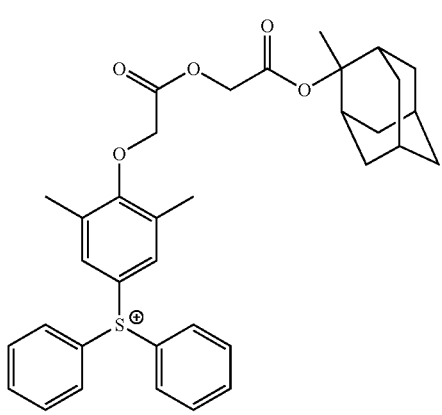
(ca-1-41)
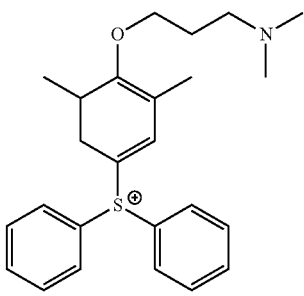
(ca-1-42)
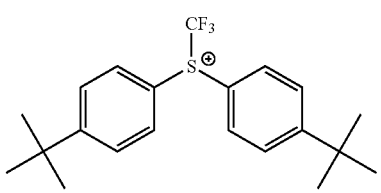
(ca-1-43)
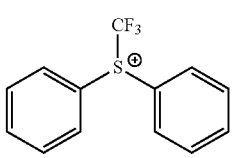
(ca-1-44)
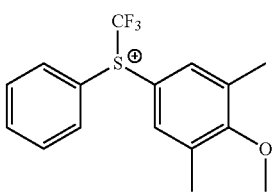
(ca-1-45)
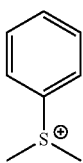
(ca-1-46)
(ca-1-47)
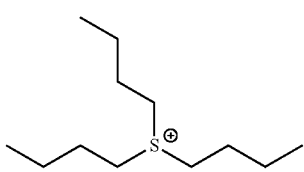

(ca-1-48)
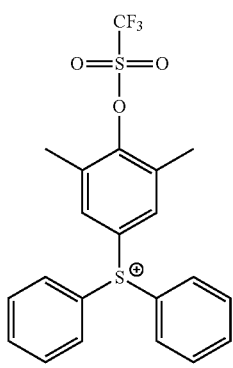
In the formulas, g1, g2 and g3 represent recurring numbers, wherein g1 is an integer of 1 to 5, g2 is an integer of 0 to 20, and g3 is an integer of 0 to 20.
[Chemical Formula 40]
(ca-1-49)
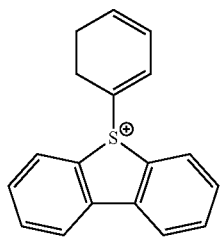
(ca-1-50)
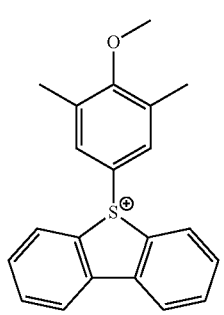
(ca-1-51)
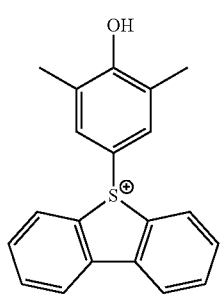
(ca-1-52)
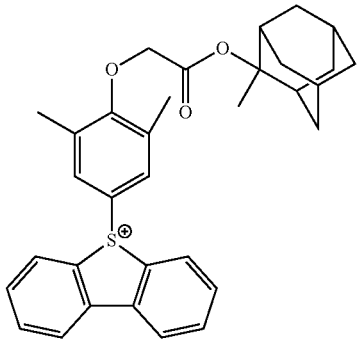
(ca-1-53)
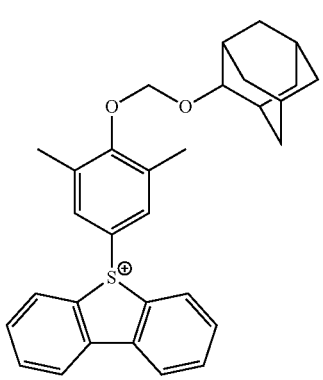
(ca-1-54)
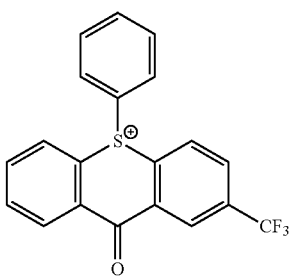
(ca-1-55)
(ca-1-56)
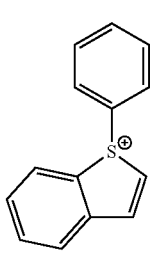

(ca-1-57) 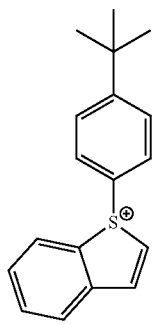

(ca-1-58) 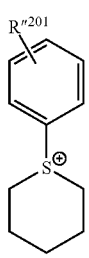

(ca-1-59) 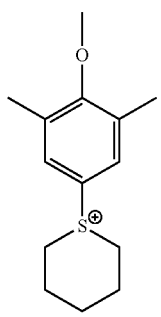

(ca-1-60) 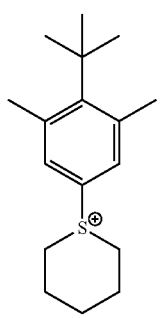

(ca-1-61) 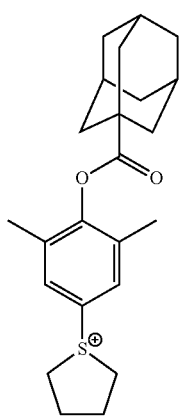

(ca-1-62) 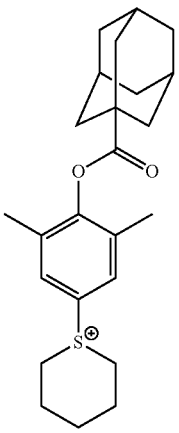

(ca-1-63) 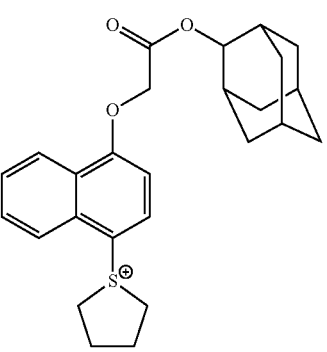

In the formulas, $R''^{201}$ represents a hydrogen atom or a substituent, and as the substituent, the same groups as those described above for substituting the $R^{201}$ to $R^{207}$ and $R^{210}$ to $R^{212}$ can be mentioned.

Specific examples of preferable cations represented by the formula (ca-3) include cations represented by formulae (ca-3-1) to (ca-3-6) shown below.

[Chemical Formula 41]

(ca-3-1) 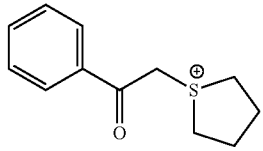

(ca-3-2) 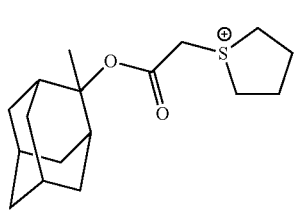

(ca-3-3) 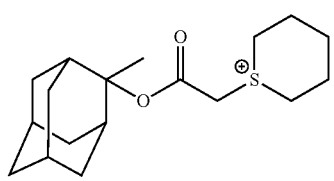

-continued (ca-3-4)
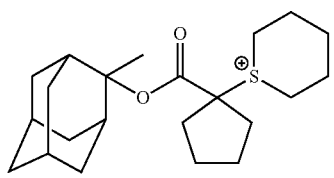

(ca-3-5)
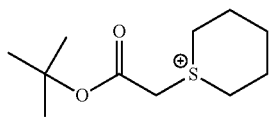

(ca-3-6)
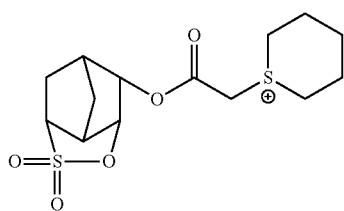

Specific examples of preferable cations represented by formula (ca-4) include cations represented by formulas (ca-4-1) to (ca-4-2) shown below.

[Chemical Formula 42]

(ca-4-1)
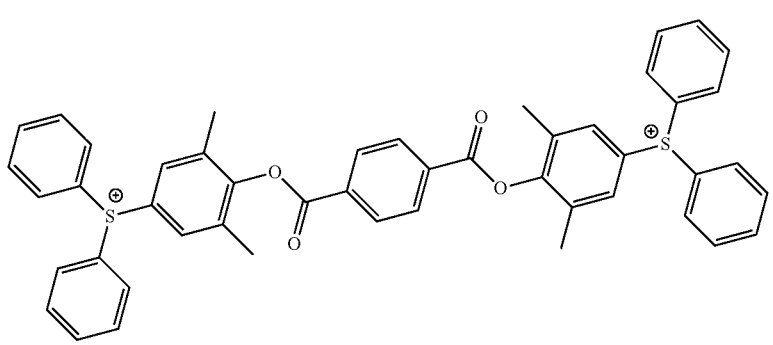

(ca-4-2)
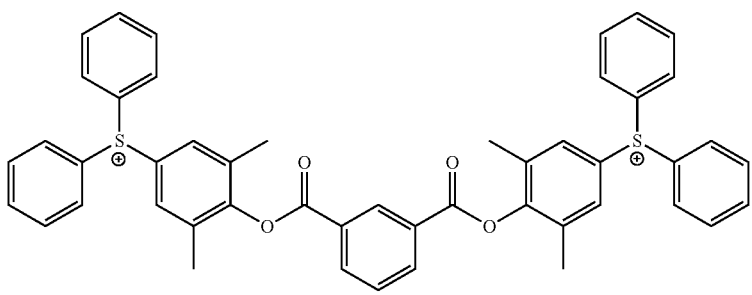

As the component (B), one type of these acid generators may be used alone, or two or more types may be used in combination.

When the resist composition of the present invention contains the component (B), the amount of the component (B) relative to 100 parts by weight of the component (A) is preferably within a range from 0.5 to 60 parts by weight, more preferably from 1 to 50 parts by weight, and still more preferably from 1 to 40 parts by weight. When the amount of the component (B) is within the above-mentioned range, formation of a resist pattern can be satisfactorily performed. Further, by virtue of the above-mentioned range, when each of the components are dissolved in an organic solvent, a uniform solution can be obtained and the storage stability becomes satisfactory.

<Photo-Decomposable Quencher (D0)>

The resist composition of the present invention includes a photo-decomposable quencher (D0) containing a compound represented by general formula (d0) shown below.

[Chemical Formula 43]

(d0)
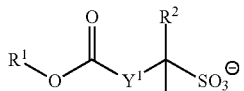

In the formula, $R^1$ represents a hydrocarbon group of 4 to 20 carbon atoms which may have a substituent; $Y^1$ represents a single bond or a divalent linking group; $R^2$ and $R^3$ each independently represents a substituent of 0 to 20 carbon atoms other than a fluorine atom; one of $R^2$ and $R^3$ may form a ring with $Y^1$; $M^{m+}$ represents an organic cation having a valency of m; and m represents an integer of 1 or more.

In formula (d0), $R^1$ represents a hydrocarbon group of 4 to 20 carbon atoms which may have a substituent.

As the hydrocarbon group for $R^1$, an alkyl group of 4 to 20 carbon atoms is preferable, and a linear or branched alkyl group is more preferable. Specific examples thereof include an n-butyl group, an isobutyl group, a tert-butyl group, a pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, 1,1-dimethylethyl group, 1,1-diethylpropyl group, 2,2-dimethylpropyl group and 2,2-dimethylbutyl group.

When $R^1$ is a cyclic hydrocarbon group, the hydrocarbon group may be either an aliphatic group or an aromatic group, and may be either a polycyclic group or a monocyclic group. As the monocyclic alicyclic hydrocarbon group, a group in which one hydrogen atom has been removed from a monocycloalkane is preferable. The monocycloalkane preferably has 4 to 8 carbon atoms, and specific examples thereof include cyclopentane, cyclohexane and cyclooctane. As the polycyclic alicyclic hydrocarbon group, a group in which one hydrogen atom has been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

In the present invention, an alicyclic hydrocarbon group may have a hetero atom in the ring structure thereof. As the substituent containing a hetero atom, —O—, —C(=O)—O—, —S—, —S(=O)$_2$—, or —S(=O)$_2$—O— can be mentioned. Specific examples of the alicyclic group include groups represented by the general formulae (a2-r-1) to (a2-r-7), (a5-r-1) to (a5-r-4), and (ax3-r-1) to (ax3-r-3), and groups represented by formulae (r-lc-1-1) to (r-lc-1-2), (r-lc-2-1), (r-lc-2-7), (r-lc-6-1), (r-lc-7-1), (r-sl-1-1) and (r-sl-1-18) are preferable.

In these aliphatic cyclic groups, part of the hydrogen atoms bonded to the carbon atoms constituting the ring structure may be substituted with a substituent. Examples of the substituent include an alkyl group, an alkoxy group, a halogen atom, a halogenated alkyl group, a hydroxy group, an oxygen atom (=O), an amino group, —OC(=O)R"$^1$ (wherein R"$^1$ represents an alkyl group of 1 to 5 carbon atoms).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which one hydrogen atom has been removed from the aforementioned aromatic hydrocarbon ring (aryl group); and a group in which one hydrogen atom of the aforementioned aryl group has been substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atoms, more preferably 1 or 2, and most preferably 1.

In the present invention, examples of the substituents which $R^1$ may have include an amino group, a group represented by —C(=O)—R"$^1$, a group represented by —O—C(=O)—R"$^1$ (R"$^1$ represents an alkyl group of 1 to 5 carbon atoms), an alkyl group, an alkoxy group, a halogen atom, a halogenated alkyl group, a hydroxyl group and an oxo group, and in terms of improving lithography properties, a polar group such as an amino group, a group represented by —O—C(=O)—R"$^1$, a hydroxy group and an oxo group are preferable.

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

In the present invention, as $R^1$, an aliphatic hydrocarbon group which may have a substituent is preferable, since lithography properties such as sensitivity, EL margin and LWR can be improved. In terms of sensitivity and properties, groups represented by the formulae (r-lc-1-1) to (r-lc-1-2), (r-lc-2-1), (r-lc-2-7), (r-lc-6-1), (r-lc-7-1), (r-sl-1-1) and (r-sl-1-18), an aliphatic hydrocarbon group having the preferable substituent, and a cyclic aliphatic hydrocarbon group which may have a substituent are more preferable.

In general formula (d0), $Y^1$ represents a single bond or a divalent linking group. As examples of the divalent linking group for $Y^1$, the same groups as those described above for $Ya^{21}$ in formula (a2-1) can be given. In the present invention, it is preferable that $Y^1$ in the formula (d0) is a single bond or an alkylene group of 1 to 5 carbon atoms which may have a substituent, except in the case where $Y^1$ forms a ring with $R^2$ or $R^3$, and it is more preferably that $Y^1$ is a single bond. As the substituent, the same substituents as those described above for $R^1$ can be mentioned.

In the formula (d0), $R^2$ and $R^3$ each independently represents a substituent of 0 to 20 other than a fluorine atom; and any one of $R^2$ and $R^3$ may form a ring with $Y^1$.

As the substituent of 0 to 20 carbon atom for $R^2$ and $R^3$, a hydrogen atom, an alkyl group (preferably having 1 to 20 carbon atoms, more preferably 1 to 12 carbon atoms, particularly preferably 1 to 8 carbon atoms, and examples thereof include a methyl group, an ethyl group, an i-propyl group, a t-butyl group, an n-octyl group, an n-decyl group, an n-hexadecyl group, a cyclopropyl group, a cyclopentyl group, a cyclohexyl group, a hexyl group, a heptyl group, an octyl group, a nonyl group, a decyl group, an undecyl group a dodecyl group, a tridecyl group, a tetradecyl group, a pentadecyl group, a hexadecyl group, a heptadecyl group, an octadecyl group, and a nonadecyl group), an alkenyl group (preferably having 2 to 20 carbon atoms, more preferably 2 to 12 carbon atoms, particularly preferably 2 to 8 carbon atoms, and examples thereof include a vinyl group, an allyl group, a 2-butenyl group, and 3-pentenyl group), an alkynyl group (preferably having 2 to 20 carbon atoms, more preferably 2 to 12 carbon atoms, particularly preferably 2 to 8 carbon atoms, and examples thereof include a propargyl group and 3-pentynyl group), an aryl group (preferably having 6 to 30 carbon atoms, more preferably 6 to 20 carbon atoms, particularly preferably 6 to 12 carbon atoms, and examples thereof include a phenyl group, a p-methylphenyl group, and a naphthyl group), a substituted or unsubstituted amino group (preferably having 0 to 20 carbon atoms, more preferably 0 to 10 carbon atoms, particularly preferably 0 to 6 carbon atoms, an examples thereof include an amino group, a methylamino group, a dimethylamino group, a diethylamino group, and a dibenzylamino group), an alkoxy group (preferably having 1 to 20 carbon atoms, more preferably 1 to 12 carbon atoms, particularly preferably 1 to 8 carbon atoms, and examples thereof include a methoxy group, an ethoxy group and a butoxy group), an aryloxy group (preferably having 6 to 20 carbon atoms, more preferably 6 to 16 carbon atoms, particularly preferably 6 to 12 carbon atoms, and examples thereof include a phenyloxy group and a 2-naphthyloxy group), an acyl group (preferably having 1 to 20 carbon atoms, more preferably 1 to 16 carbon atoms, particularly preferably 1 to 12 carbon atoms, and examples thereof include an acetyl group, a benzoly group, a formyl group, and a pivaloyl group), an alkoxycarbonyl group (preferably having 2 to 20 carbon atoms, more preferably 2 to 16 carbon atoms, particularly preferably 2 to 12 carbon atoms, and examples thereof include a methoxycarbonyl group, and an ethoxycarbonyl group), an aryloxycarbonyl group (preferably having 7 to 20 carbon atoms, more preferably 7 to 16 carbon atoms, particularly preferably 7 to 10 carbon atoms, examples thereof include a phenyloxycarbonyl group), an acyloxy group (preferably having 2 to 20 carbon atoms, more preferably 2 to 16 carbon atoms, particularly preferably 2 to 10 carbon atoms, and examples thereof include an acetoxy group and a benzoyloxy group), an acylamino group (preferably having 2 to 20 carbon atoms, more preferably 2 to 16 carbon atoms, particularly preferably 2 to 10 carbon atoms, and examples thereof include an acetylamino group and a benzolyamino group), an alkoxycarbonylamino group (preferably having 2 to 20 carbon atoms, more preferably 2 to 16 carbon atoms, particularly preferably 2 to 12 carbon atoms, and examples thereof include a methoxycarbonylamino group), and aryloxycarbonylamino group (preferably having 7 to 20 carbon atoms, more preferably 7 to 16 carbon atoms, particularly preferably 7 to 12 carbon atoms, and examples thereof include a phenyloxycarbonyl amino group), a sulfonylamino group (preferably having 1 to 20 carbon atoms, more preferably 1 to 16 carbon atoms, particularly preferably 1 to 12 carbon atoms, and examples thereof include a methanesulfonylamino group, and a benzenesulfonylamino group), a hydroxy group, a mercapto group, a chlorine atom, a bromine atom, an iodine atom, a cyano group, a sulfo group, a carboxyl group, a nitro group, a hydroxamic acid group, a sulfino group, a hydrazino group, an imino group, a heterocyclic group (preferably having 1 to 30 carbon atoms, more preferably 1 to 12 carbon atoms, and as the hetero atom, a nitrogen atom, an oxygen atom, and a sulfur atom can be mentioned, and examples of the heterocyclic groups include a imidazoyl group, a pyridyl group, a quinolyl group, a furyl group, a piperidyl group, a morpholino group, a benzoxazolyl group, and a benzthiazolyl group), and a silyl group (preferably having 3 to 40 carbon atoms, more preferably 3 to 30 carbon atoms, particularly preferably 3 to 24, and examples thereof include a trimethylsilyl group and a triphenylsilyl group) can be mentioned.

When any one of the $R^2$ and $R^3$ is an alkyl group, one of the hydrogen atoms within the alkyl group may be substituted with —C(=O)—O—$R^1$ ($R^1$ is the same as defined above). The alkyl group is preferably a methyl group.

When $R^2$ or $R^3$ is a cyclic hydrocarbon group, the hydrocarbon group may be either an aliphatic group or an aromatic group, and may be either a polycyclic group or a monocyclic group. As the monocyclic alicyclic hydrocarbon group, a group in which one hydrogen atom has been removed from a monocycloalkane is preferable. The monocycloalkane preferably has 4 to 8 carbon atoms, and specific examples thereof include cyclopentane, cyclohexane and cyclooctane. As the polycyclic alicyclic hydrocarbon group, a group in which one hydrogen atom has been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

In the present invention, an alicyclic hydrocarbon group may have a hetero atom in the ring structure thereof. As the substituent containing a hetero atom, —O—, —C(=O)—O—, —S—, —S(=O)$_2$—, or —S(=O)$_2$—O— can be mentioned. Specific examples of the alicyclic group include groups represented by the general formulae (a2-r-1) to (a2-r-7), (a5-r-1) to (a5-r-4), and (ax3-r-1) to (ax3-r-3), and groups represented by formulae (r-lc-1-1) to (r-lc-1-2), (r-lc-2-1), (r-lc-2-7), (r-lc-6-1), (r-lc-7-1), (r-sl-1-1) and (r-sl-1-18) are preferable.

In the formula (d0), $R^2$ and $R^3$ each independently represents a substituent of 0 to 20 carbon atoms other than a fluorine atom; one of $R^2$ and $R^3$ may form a ring with $Y^1$. When one of $R^2$ and $R^3$ form a ring with $Y^1$, the group represented by (d0-1) shown below is any one of the groups represented by formulae (d0-1-1) to (d0-1-4).

[Chemical Formula 44]

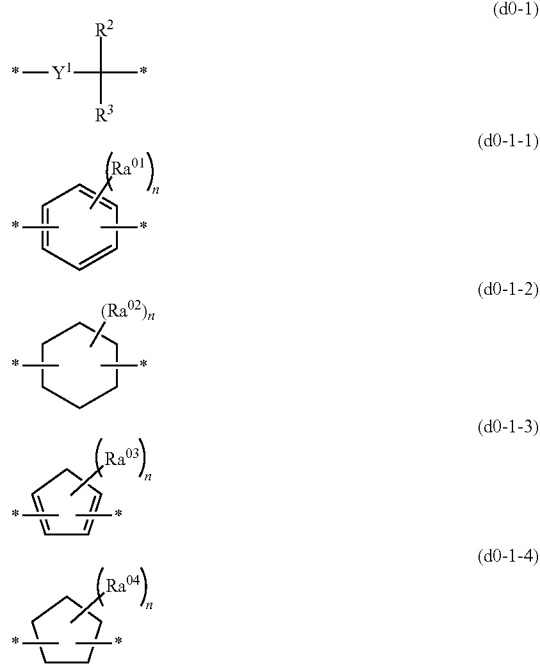

In the formulae, $Y^1$ represents a single bond or a divalent linking group; $R^2$ and $R^3$ each independently represents a substituent of 0 to 20 carbon atoms other than a fluorine atom; $R^{01}$ to $R^{04}$ each represents an alkyl group of 1 to 10 carbon atoms which may have a substituent; n represents an integer of 0 to 2; and * represents a valence bond.

In the formula (d0-1), $Y^1$, $R^2$ and $R^3$ are the same as defined for $R^1$, $R^2$ and $R^3$ in the formula (d0).

Examples of the alkyl group of 1 to 10 carbon atoms for $R^{01}$ to $R^{04}$ which may have a substituent include a methyl group, an ethyl group, an i-propyl group, a t-butyl group, an n-octyl group, an n-decyl group, an n-hexadecyl group, a cyclopropyl group, a cyclopentyl group and a cyclohexyl group. The substituent which $Ra^{01}$ to $R^{04}$ may have, may be used in the case where a hydrogen atom (—H) within an alkyl group of $Ra^{01}$ to $R^{04}$ is substituted with a monovalent group, or in the case where a methylene group (—CH$_2$—) is substituted with a divalent group. Examples of the substituents include an imino group, an amino group, a hydroxy group, a mercapto group, a halogen atom (e.g., a chlorine atom, a bromine atom, an iodine atom), a cyano group, a sulfo atom, a carboxyl group and a nitro group.

Specific examples of the anion moiety of the compound represented by formula (d0) are shown below.

[Chemical Formula 45]

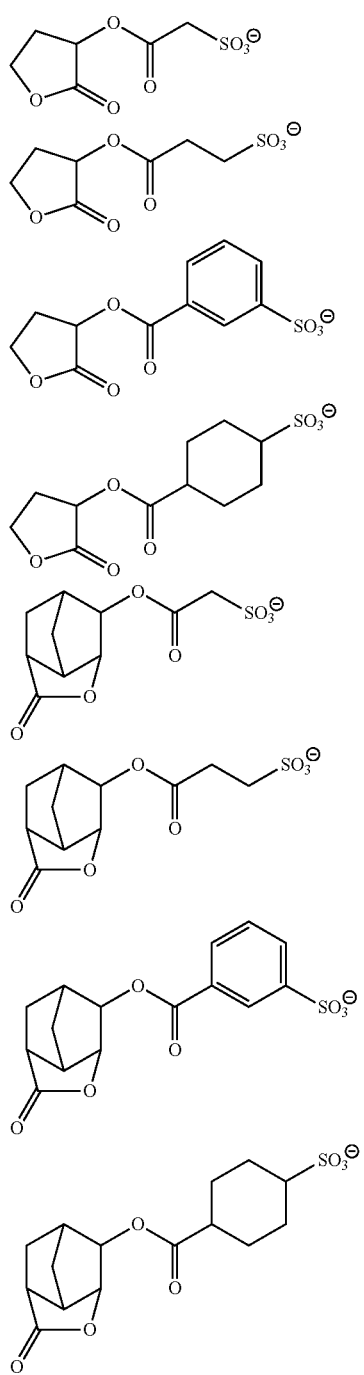

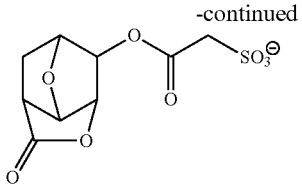

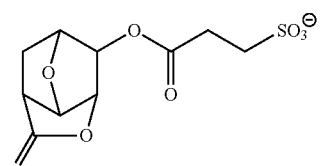

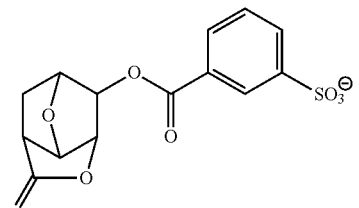

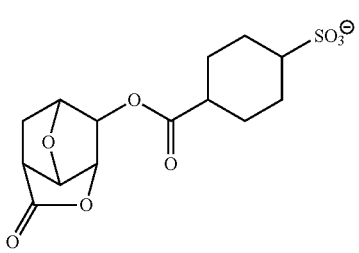

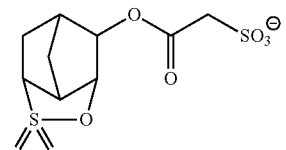

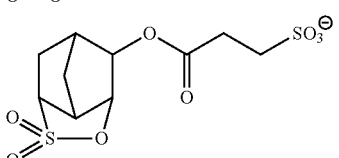

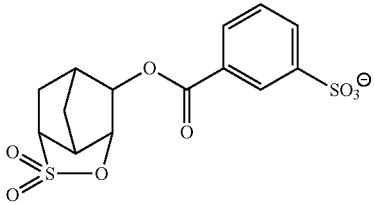

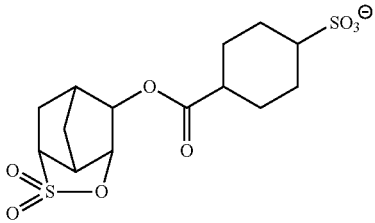

[Chemical Formula 46]
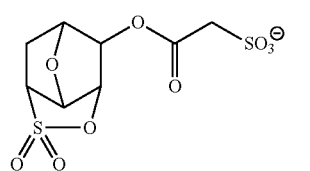
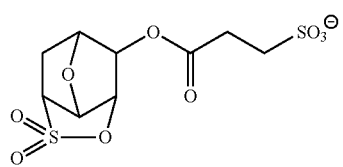
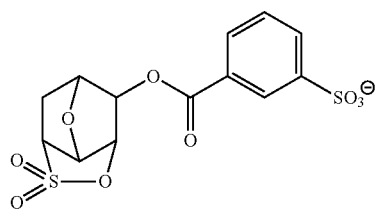
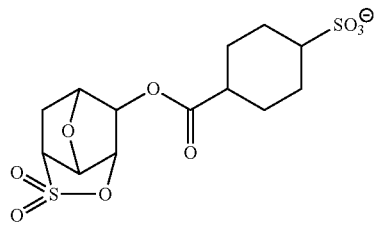
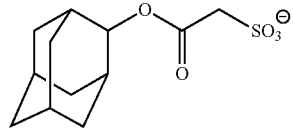
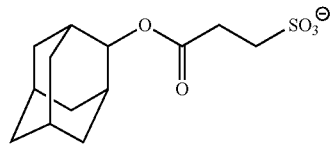
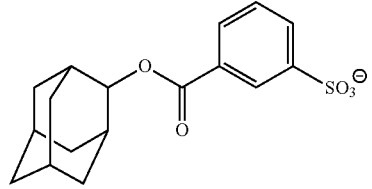
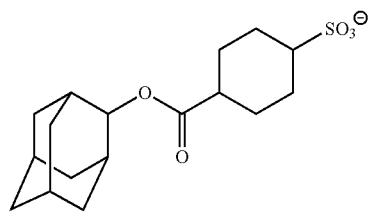
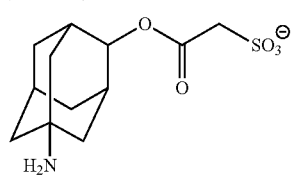
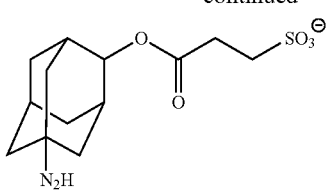
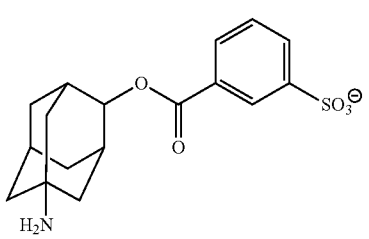
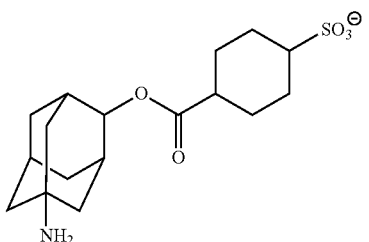
[Chemical Formula 47]
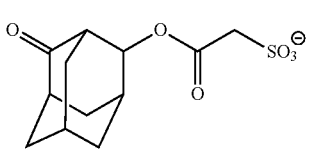
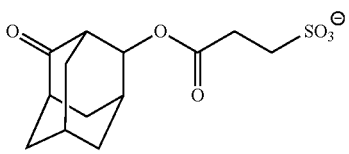
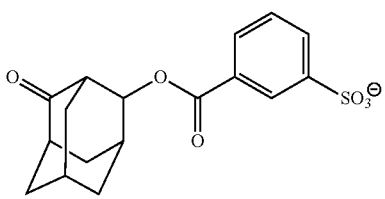
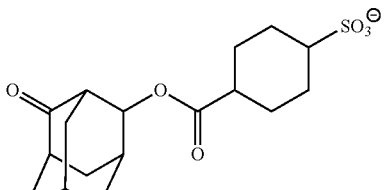
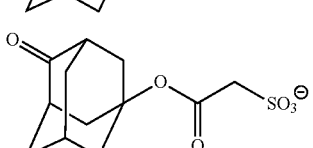
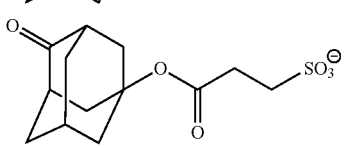

-continued
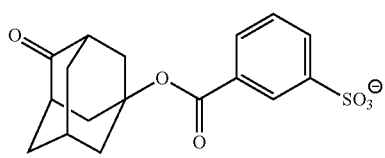
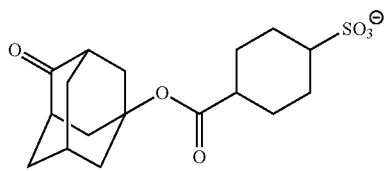
[Chemical Formula 48]
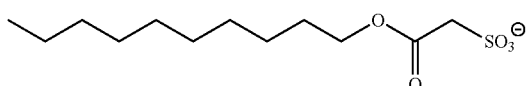
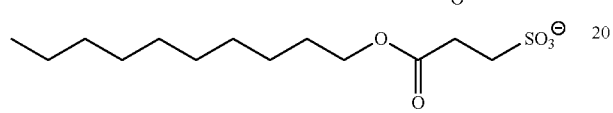
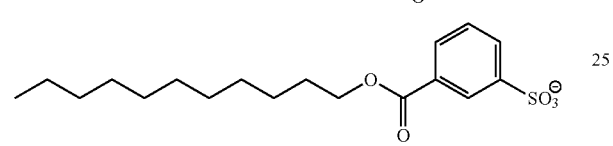
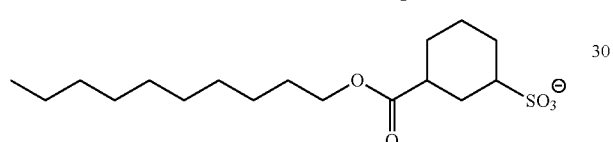
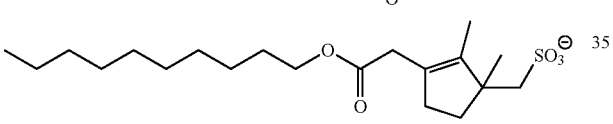
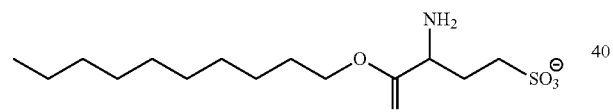
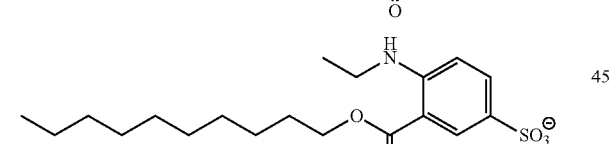
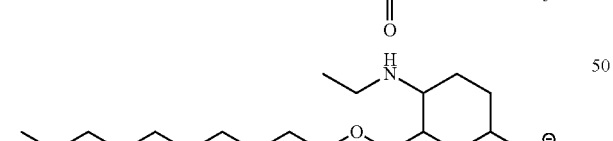
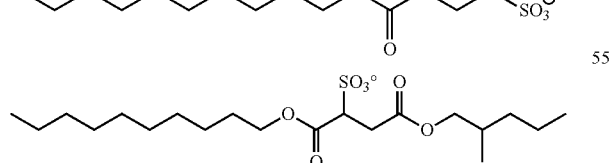
[Chemical Formula 49]
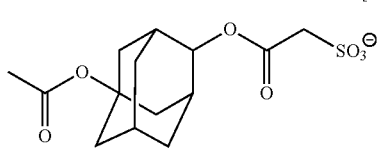
-continued
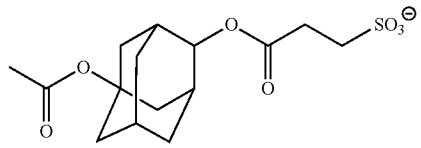
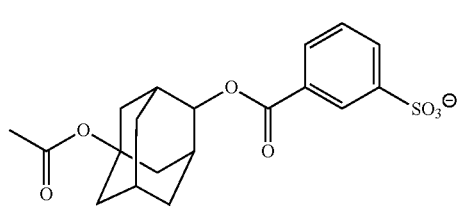
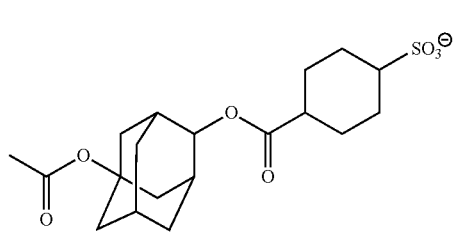
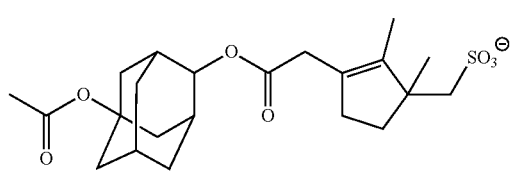
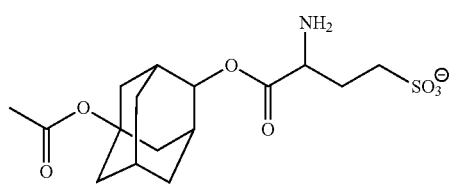
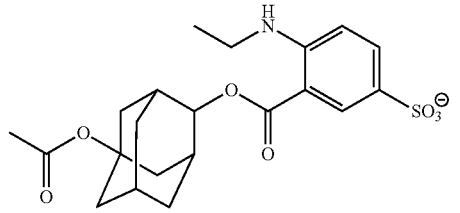
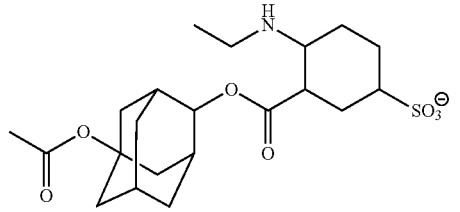
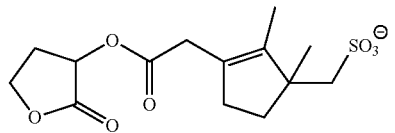
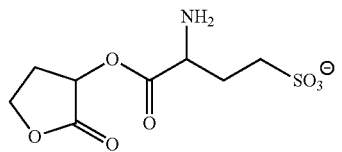

-continued
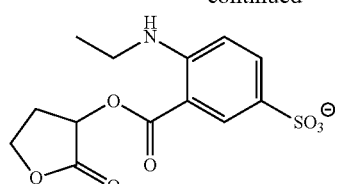
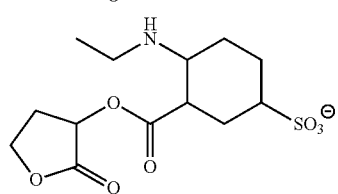
[Chemical Formula 50]
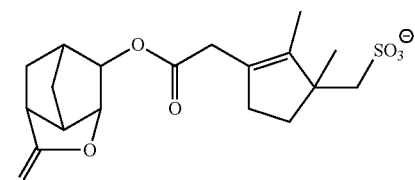
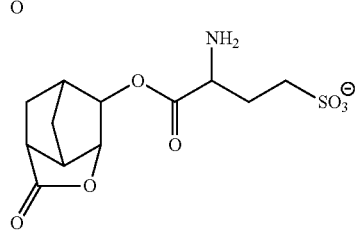
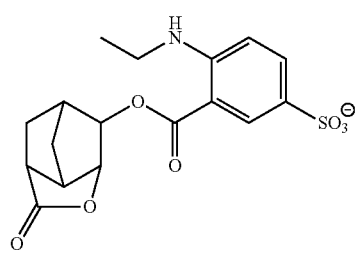
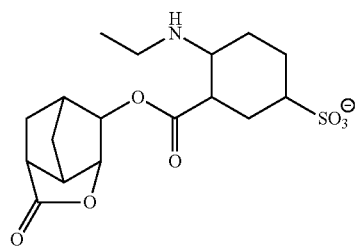
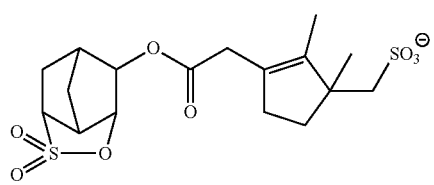
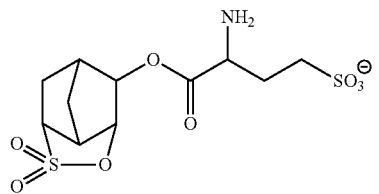
-continued
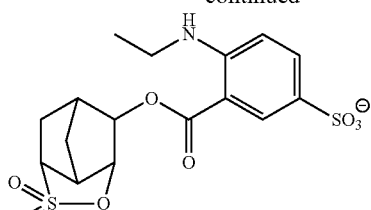
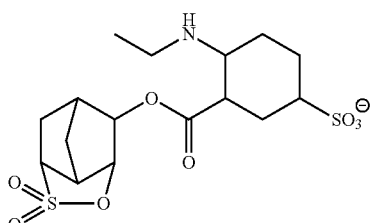
[Chemical Formula 51]
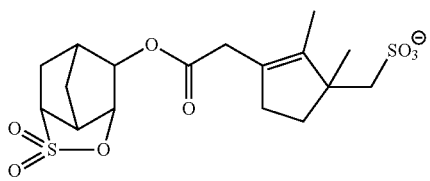
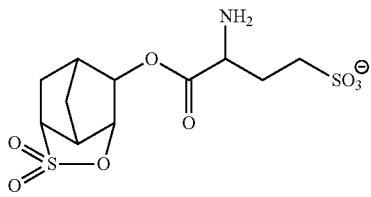
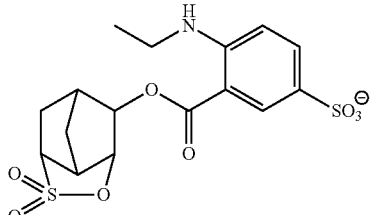
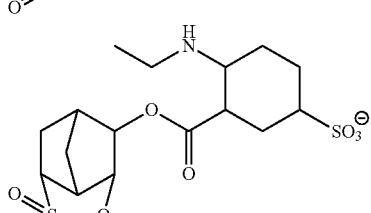
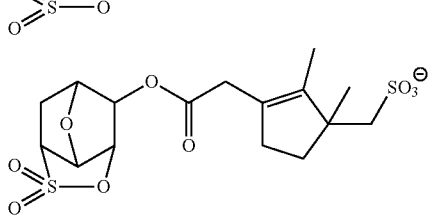
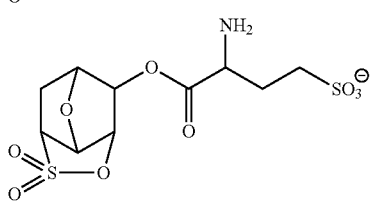

97
-continued
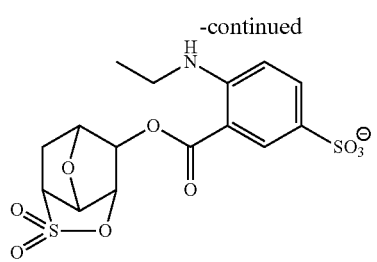
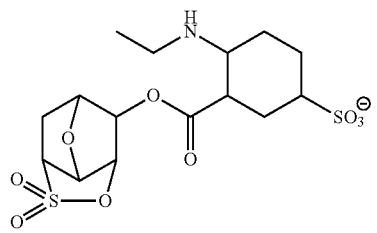
[Chemical Formula 52]
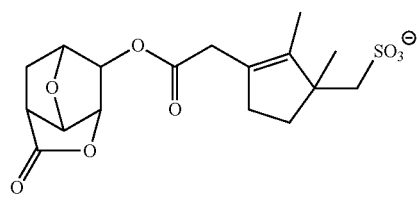
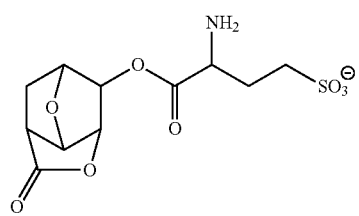
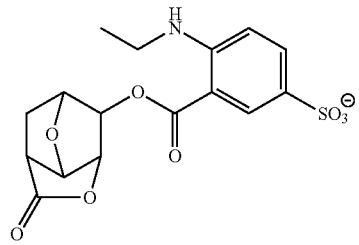
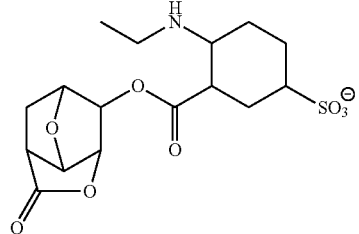
[Chemical Formula 53]
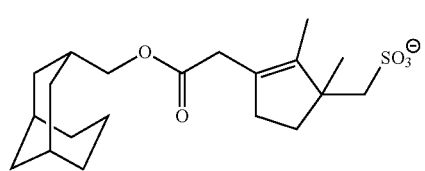
98
-continued
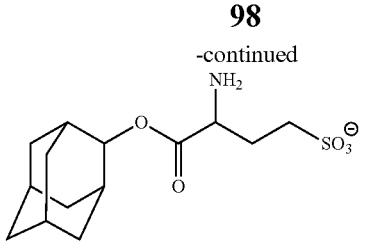
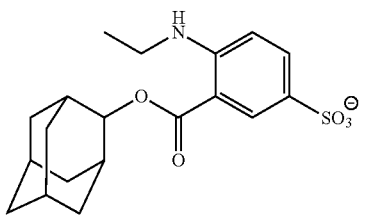
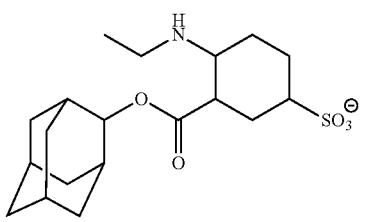
[Chemical Formula 54]
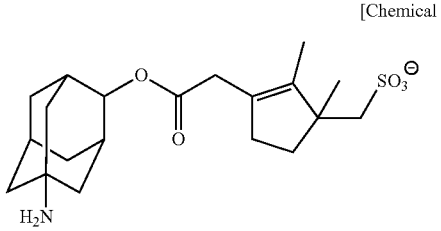
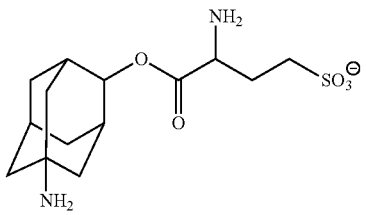
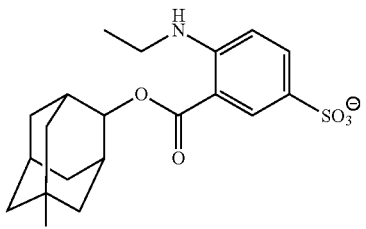
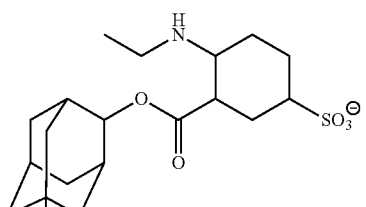
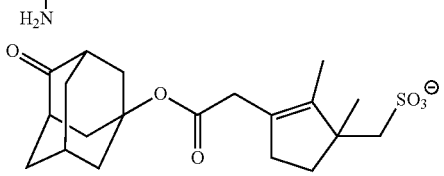

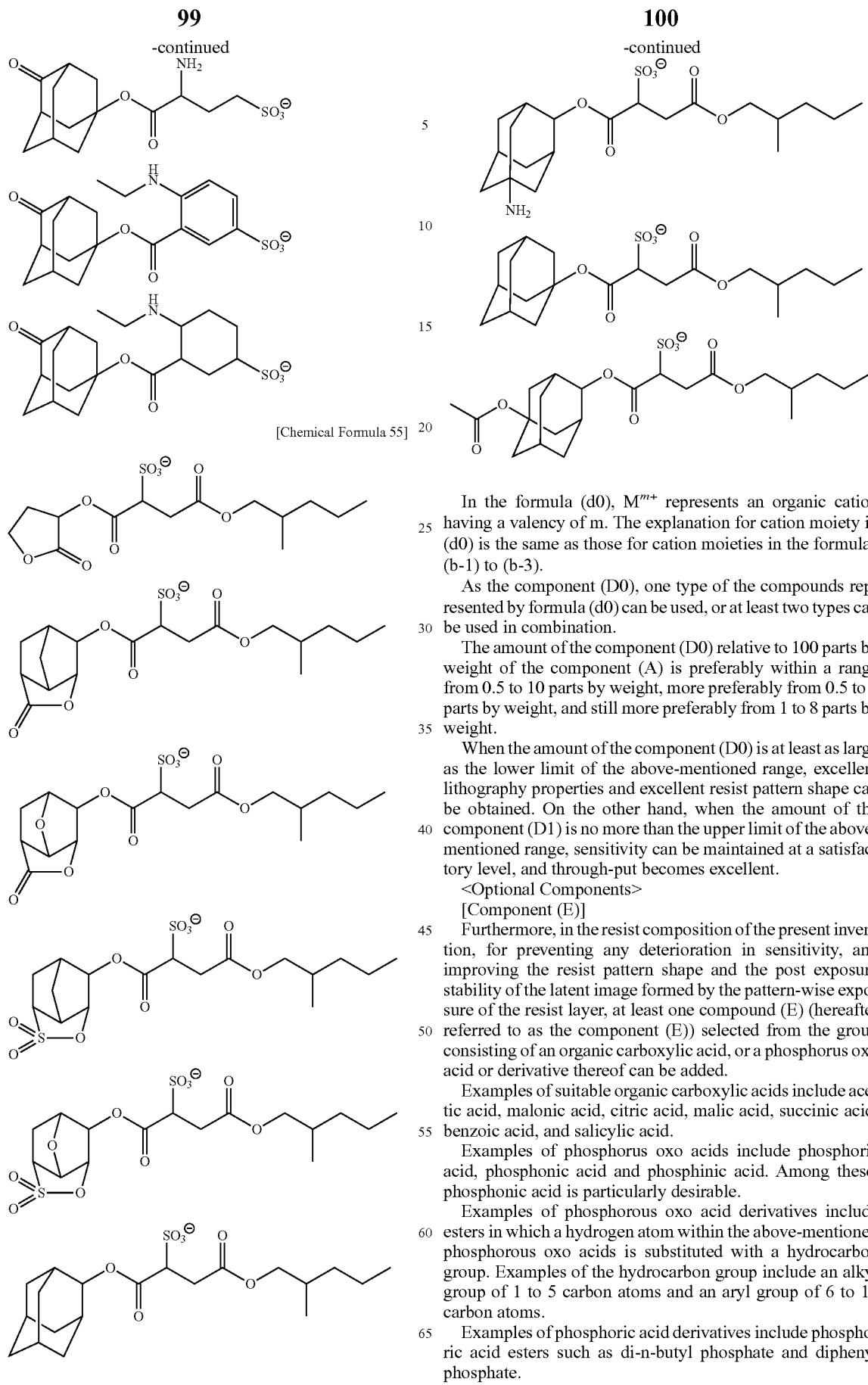

In the formula (d0), $M^{m+}$ represents an organic cation having a valency of m. The explanation for cation moiety in (d0) is the same as those for cation moieties in the formulae (b-1) to (b-3).

As the component (D0), one type of the compounds represented by formula (d0) can be used, or at least two types can be used in combination.

The amount of the component (D0) relative to 100 parts by weight of the component (A) is preferably within a range from 0.5 to 10 parts by weight, more preferably from 0.5 to 8 parts by weight, and still more preferably from 1 to 8 parts by weight.

When the amount of the component (D0) is at least as large as the lower limit of the above-mentioned range, excellent lithography properties and excellent resist pattern shape can be obtained. On the other hand, when the amount of the component (D1) is no more than the upper limit of the above-mentioned range, sensitivity can be maintained at a satisfactory level, and through-put becomes excellent.

<Optional Components>
[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of phosphorous oxo acid derivatives include esters in which a hydrogen atom within the above-mentioned phosphorous oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenyl phosphonate, diphenyl phosphonate and dibenzyl phosphonate.

Examples of phosphinic acid derivatives include phenylphosphinic acid and phosphinic acid esters.

As the component (E), one type may be used alone, or two or more types may be used in combination.

The component (E) is typically used in an amount within a range from 0.01 to 5.0 parts by weight, relative to 100 parts by weight of the component (A).

[Component (F)]

In the present invention, the resist composition may further include a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of a structural unit (f1) represented by formula (f1-1) shown below and the aforementioned structural unit (a1); and a copolymer of a structural unit (f1) represented by the formula (f1-1) shown below, a structural unit derived from acrylic acid or methacrylic acid and the aforementioned structural unit (a1) are preferable. As the structural unit (a1) to be copolymerized with a structural unit (f1) represented by formula (f1-1) shown below, a structural unit derived from 1-ethyl-1-cyclooctyl (meth)acrylate or a structural unit represented by the aforementioned formula (a1-2-01) is preferable.

[Chemical Formula 56]

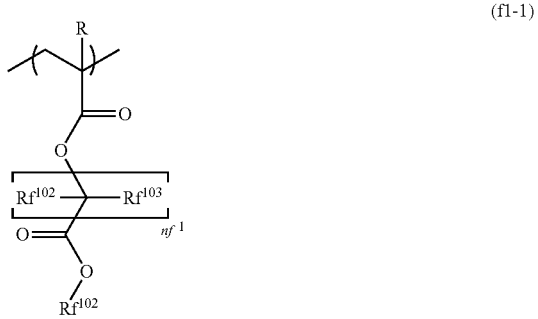

(f1-1)

In the formula, R is the same as defined above; $Rf^{102}$ and $Rf^{103}$ each independently represents a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group of 1 to 5 carbon atoms for $Rf^{102}$ and $Rf^{103}$ include the same alkyl group of 1 to 5 carbon atoms as those described above for R, and a methyl group or an ethyl group is preferable. Specific examples of the halogenated alkyl group of 1 to 5 carbon atoms represented by $Rf^{102}$ and $Rf^{103}$ include groups in which part or all of the hydrogen atoms of the aforementioned alkyl groups of 1 to 5 carbon atoms have been substituted with halogen atoms. Examples of the halogen atom include a fluorine atom, a chlorine atom, a bromine atom and an iodine atom, and a fluorine atom is particularly desirable. Among these, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group of 1 to 5 carbon atoms is preferable, and a methyl group, $-CH_2-CF_3$, $-CH_2-CF_2-CF_3$, $-CH(CF_3)_2$, $-CH_2-CH_2-CF_3$ and $-CH_2-CH_2-CF_2-CF_2-CF_2-CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

The component (F) is typically used in an amount within a range from 0.5 to 10 parts by weight, relative to 100 parts by weight of the component (A).

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

[Component (S)]

The resist composition of the present invention can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone (MEK), cyclohexanone, methyl-n-pentyl ketone (2-heptanone), and methyl isopentyl ketone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, PGMEA, PGME, γ-butyrolactone and EL are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL weight ratio or PGMEA:cyclohexanone weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a resist solution to a substrate. In general, the organic solvent is used in an amount such that the solid content of the resist composition becomes within the range from 1 to 20% by weight, and preferably from 2 to 15% by weight.

The resist compositions of the present invention exhibited excellent sensitivity and lithography properties such as EL margin and LWR. The reason for this has not been elucidated yet, but is presumed as follows.

The resist composition of the present invention includes a compound as a photo-decomposable quencher, which has a bulky group. Therefore, it is presumed that diffusion of the acid generated at exposed portions to unexposed portions can be suppressed, thereby improving lithography properties and sensitivity.

<<Method of Forming a Resist Pattern>>

The method of forming a resist pattern of the second aspect of the present invention includes: forming a resist film on a substrate using a resist composition of the present invention; conducting exposure of the resist film; and developing the resist film to form a resist pattern.

The method for forming a resist pattern according to the present invention can be performed, for example, as follows.

Firstly, a resist composition of the present invention is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment.

The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing. In this manner, a resist pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic anti-reflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film is formed (triple-layer resist method).

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which preferably have a boiling point within a range from 70 to 180° C. and more preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used, which are capable of dissolving the component (A) (prior to exposure). Specific examples of the organic solvent include polar solvents such as ketone solvents, ester solvents, alcohol solvents, amide solvents and ether solvents, and hydrocarbon solvents.

If desired, the organic developing solution may have a conventional additive blended. Examples of the additive include surfactants. The surfactant is not particularly limited, and for example, an ionic or non-ionic fluorine and/or silicon surfactant can be used.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

<<Compound>>

A third aspect of the present invention is a compound represented by general formula (d0)-1 shown below.

[Chemical Formula 57]

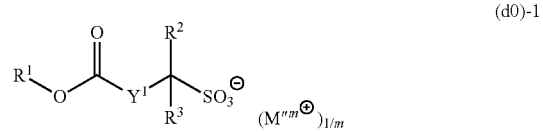

(d0)-1

In the formula, $R^1$ represents a hydrocarbon group of 4 to 20 carbon atoms which may have a substituent; $Y^1$ represents a single bond or a divalent linking group; $R^2$ and $R^3$ each independently represents a substituent of 0 to 20 carbon atoms other than a fluorine atom; one of $R^2$ and $R^3$ may form a ring with $Y^1$; $M^{m+}$ represents a cation having a valency of m; and m represents an integer of 1 or more.

In the formula (d0)-1, $Y^1$, $R^1$, $R^2$ and $R^3$ are the same as defined for $Y^1$, $R^1$, $R^2$ and $R^3$ in the formula (d0) in the resist composition.

$M^{m+}$ represents a cation having a valency of m, and examples thereof include an alkali metal cation and an organic cation. Examples of alkali metal ions include a sodium ion, a lithium ion and a potassium ion, and a sodium ion or a lithium ion is preferable. As the organic cation, a cation containing a nitrogen atom such as an ammonium ion and a pyridinium ion, and the same organic cations as those described above for $M^{m+}$ in the formula (d0) can be mentioned.

The compound of the present invention can be blended in a resist composition as a photo-decomposable quencher.

EXAMPLES

As follows is a description of examples of the present invention, although the scope of the present invention is by no way limited by these examples.

Synthesis Example 1

Synthesis of Compound (D)-1

3.0 g of sulfoacetic acid, 37.7 g of toluene, 1.69 g of pyridine, and 3.67 g of a compound (1) shown below were added to a three-necked flask equipped with a cooling pipe and a thermometer, followed by refluxing at 110° C. for 10 hours. Thereafter, the reaction mixture was filtered, and 754 g of t-butyl methyl ether was added to the residue, followed by stirring. The filtration step was performed twice to obtain 6.25 g of a compound (d-1) shown below.

The obtained compound (d-1) was analyzed by NMR, and the structure thereof was identified by the following results.

$^1$H-NMR (400 MHz, DMSO-d6): δ (ppm)=8.98 (d, 2H, Py), 8.69 (t, 1H, Py), 8.19 (d, 2H, Py), 4.80 (d, 1H, Sultone), 4.50 (s, 1H, Sultone), 3.90 (m, 1H, Sultone), 3.40-3.80 (m, 3H, Sultone+CH$_2$), 2.40 (s, 1H, Sultone), 1.70-2.20 (m, 4H, Sultone)

[Chemical Formula 58]

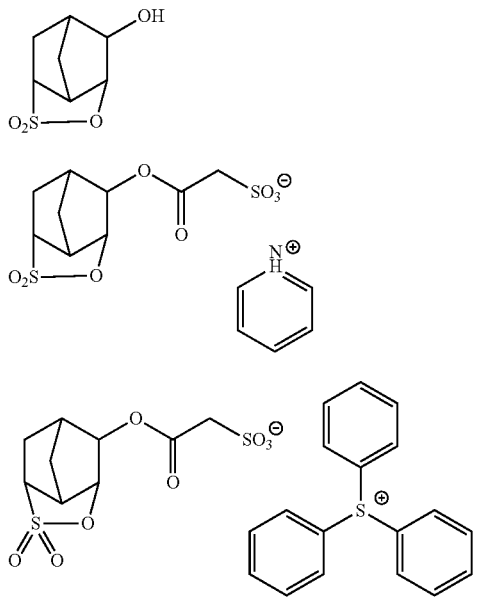

(Salt Exchange and NMR Analysis)

2.0 g of the compound (d-1), 1.61 g of triphenylsulfonium bromide, 27 g of dichloromethane, and 27 g of pure water were added to a flask, and stirred at room temperature for 12 hours. After stirring, the organic phase was separated and washed with water, and then subjected to distillation under reduced pressure to remove the solvent, thereby obtaining 1.20 g of a compound (D)-1 shown below.

The obtained compound was analyzed by NMR, and the structure thereof was identified by the following results.

$^1$H-NMR (400 MHz, DMSO-d6): δ (ppm)=7.60-8.10 (m, 15H, Phenyl), 4.80 (d, 1H, Sultone), 4.50 (s, 1H, Sultone), 3.90 (m, 1H, Sultone), 3.40-3.80 (m, 3H, Sultone+CH$_2$), 2.40 (s, 1H, Sultone), 1.70-2.20 (m, 4H, Sultone)

Synthesis Example 2

Synthesis of Compound (D)-2

3.03 g of sulfoacetic acid, 38.1 g of toluene, 1.71 g of pyridine, and 3.71 g of a compound (2) shown below were added to a three-necked flask equipped with a cooling pipe and a thermometer, followed by refluxing at 110° C. for 5 hours. Thereafter, the reaction mixture was filtered, and 762 g of t-butyl methyl ether was added to the residue, followed by stirring. A step of decantation was performed twice, and the collected product was dried, thereby obtaining 6.20 g of a compound (d-2) shown below.

The obtained compound (d-2) was analyzed by NMR, and the structure thereof was identified by the following results.

$^1$H-NMR (400 MHz, dmso-d6): δ (ppm)=8.98 (d, 2H, Py), 8.69 (t, 1H, Py), 8.19 (d, 2H, Py), 5.30 (d, 1H, Oxosultone), 4.60-4.90 (m, 3H, oxosultone), 4.30 (s, 1H, oxosultone), 3.40 (s, 2H, CH$_2$), 2.10-2.30 (m, 2H, oxosultone)

[Chemical Formula 59]

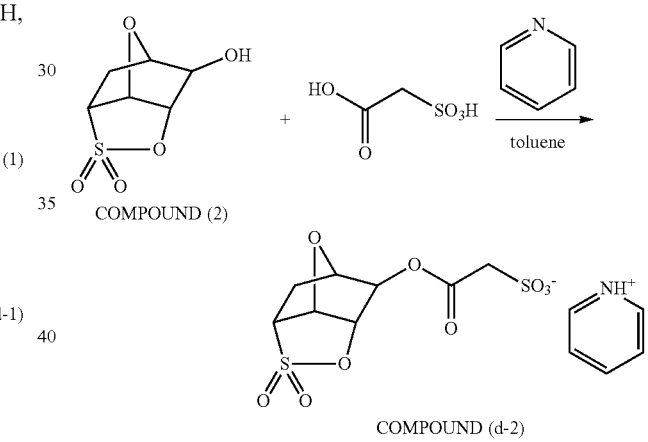

The obtained compound (d-2) was subjected to salt exchange in the same manner as in Synthesis Example 1 to obtain a compound (D)-2. The obtained compound (D)-2 was analyzed by NMR, and the structure thereof was identified. The results are shown in Table 1.

Synthesis Example 3

Synthesis of Compound (D)-3

2.43 g of sulfoacetic acid, 30 g of toluene, 1.37 g of pyridine, and 2.97 g of a compound (3) shown below were added to a three-necked flask equipped with a cooling pipe and a thermometer, followed by refluxing at 110° C. for 10 hours. Thereafter, the reaction mixture was filtered, and 611 g of t-butyl methyl ether was added to the residue, followed by stirring. The filtration step was performed twice to obtain 5.00 g of a compound (d-3) shown below.

The obtained compound (d-3) was analyzed by NMR, and the structure thereof was identified by the following results.

$^1$H-NMR (400 MHz, dmso-d6): δ (ppm)=8.98 (d, 2H, Py), 8.69 (t, 1H, Py), 8.19 (d, 2H, Py), 4.30 (m, 2H, Norbornane), 3.50 (m, 2H, CH$_2$), H, Norbornane), 2.40 (m, 2H, Norbornane), 1.90 (m, 2H, Norbornane), 1.52 (m, 2H, Norbornane)

[Chemical Formula 60]

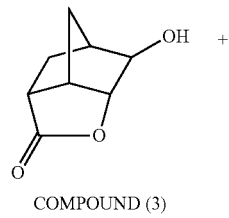

COMPOUND (3)

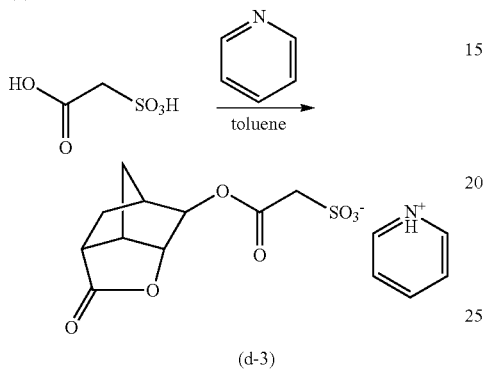

(d-3)

The obtained compound (d-3) was subjected to salt exchange in the same manner as in Synthesis Example 1 to obtain a compound (D)-3. The obtained compound (D)-3 was analyzed by NMR, and the structure thereof was identified. The results are shown in Table 1.

Synthesis Example 4

Synthesis of Compound (D)-4

2.46 g of sulfoacetic acid, 31 g of toluene, 1.39 g of pyridine, and 3.01 g of a compound (4) shown below were added to a three-necked flask equipped with a cooling pipe and a thermometer, followed by refluxing at 110° C. for 10 hours. Thereafter, the reaction mixture was filtered, and 620 g of n-hexane was added to the residue, followed by stirring. A filtration was conducted to obtain 5.02 g of a compound (d-4) shown below.

The obtained compound (d-4) was analyzed by NMR, and the structure thereof was identified by the following results.

$^1$H-NMR (400 MHz, dmso-d6): δ (ppm)=8.98 (d, 2H, Py), 8.69 (t, 1H, Py), 8.19 (d, 2H, Py), 5.49 (s, 1H, Oxonorbornane), 4.98 (s, 1H, Oxonorbornane), 4.70 (s, 1H, Oxonorbornane), 4.58 (s, 1H, Oxonorbornane), 3.50 (m, 2H, CH$_2$), 2.71 (s, 1H, Oxonorbornane), 2.11 (m, 2H, Oxonorbornane)

[Chemical Formula 61]

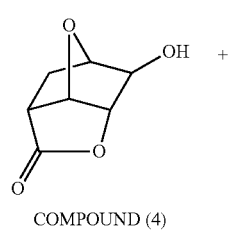

COMPOUND (4)

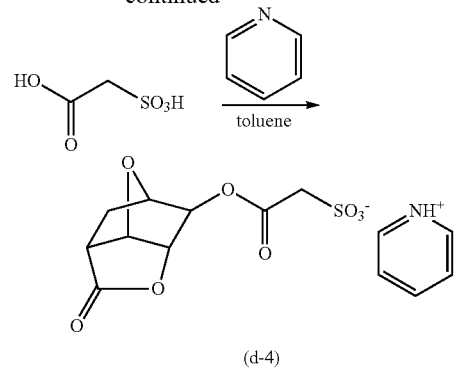

(d-4)

The obtained compound (d-4) was subjected to salt exchange in the same manner as in Synthesis Example 1 to obtain a compound (D)-4. The obtained compound (D)-4 was analyzed by NMR, and the structure thereof was identified. The results are shown in Table 1.

Synthesis Example 5

Synthesis of Compound (D)-5

1.61 g of sulfoacetic acid, 21 g of toluene, 0.91 g of pyridine, and 1.97 g of a compound (5) shown below were added to a three-necked flask equipped with a cooling pipe and a thermometer, followed by refluxing at 110° C. for 5 hours. Thereafter, the reaction mixture was filtered, and 400 g of n-hexane was added to the residue, followed by stirring. A filtration was conducted to obtain 3.00 g of a compound (d-5) shown below.

The obtained compound (d-5) was analyzed by NMR, and the structure thereof was identified by the following results.

$^1$H-NMR (400 MHz, dmso-d6): δ (ppm)=8.98 (d, 2H, Py), 8.69 (t, 1H, Py), 8.19 (d, 2H, Py), 5.70 (t, 1H, OCHC=O), 4.46-4.30 (m, 2H, OCOCH$_2$), 3.50 (m, 2H, CH$_2$), 2.71-2.64 (m, 1H, OCH$_2$CH$_2$), 2.33-2.24 (m, 1H, OCH$_2$CH$_2$)

[Chemical Formula 62]

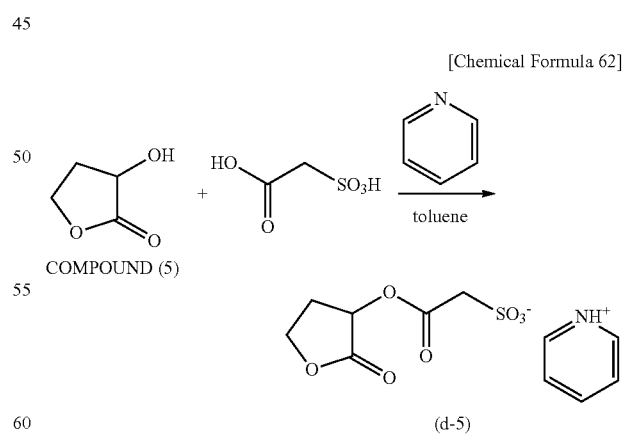

The obtained compound (d-5) was subjected to salt exchange in the same manner as in Synthesis Example 1 to obtain a compound (D)-5. The obtained compound (D)-5 was analyzed by NMR, and the structure thereof was identified. The results are shown in Table 2.

Synthesis Example 6

Synthesis of Compound (D)-6

2.40 g of sulfoacetic acid, 30.2 g of toluene, 1.35 g of pyridine, and 2.95 g of a compound (6) shown below were added to a three-necked flask equipped with a cooling pipe and a thermometer, followed by refluxing at 110° C. for 10 hours.

Thereafter, the reaction mixture was filtered, and 600 g of t-butyl methyl ether was added to the residue, followed by stirring. The filtration step was performed twice to obtain 3.03 g of a compound (d-6) shown below.

The obtained compound (d-6) was analyzed by NMR, and the structure thereof was identified by the following results.

$^1$H-NMR (400 MHz, dmso-d6): δ (ppm)=8.98 (d, 2H, Py), 8.69 (t, 1H, Py), 8.19 (d, 2H, Py), 4.80 (s, 1H, Adamantane), 3.80 (s, 2H, $CH_2$), 2.11 (d, 2H, Adamantane), 1.30-1.98 (m, 12H, Adamantane)

[Chemical Formula 63]

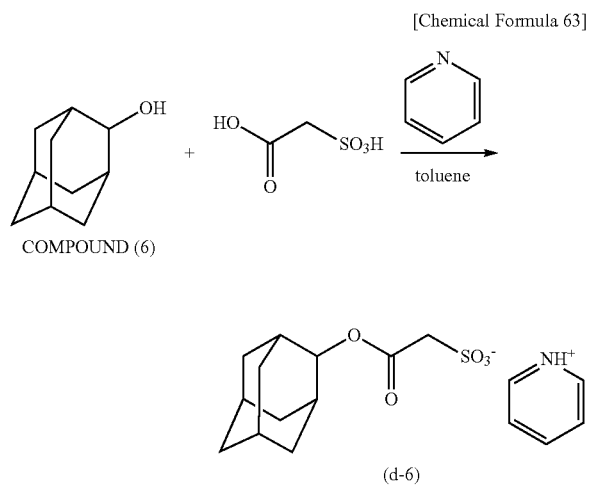

The obtained compound (d-6) was subjected to salt exchange in the same manner as in Synthesis Example 1 to obtain a compound (D)-6. The obtained compound (D)-6 was analyzed by NMR, and the structure thereof was identified. The results are shown in Table 2.

Synthesis Example 7

Synthesis of Compound (D)-7

2.50 g of sulfoacetic acid, 31.4 g of toluene, 1.41 g of pyridine, and 3.05 g of a compound (7) shown below were added to a three-necked flask equipped with a cooling pipe and a thermometer, followed by refluxing at 110° C. for 5 hours. Thereafter, the reaction mixture was filtered, and 630 g of t-butyl methyl ether was added to the residue, followed by stirring. The filtration step was performed twice to obtain 5.20 g of a compound (d-7) shown below.

The obtained compound (d-7) was analyzed by NMR, and the structure thereof was identified by the following results.

$^1$H-NMR (400 MHz, dmso-d6): δ (ppm)=8.98 (d, 2H, Py), 8.69 (t, 1H, Py), 8.19 (d, 2H, Py), 3.99 (t, 2H, $COOCH_2$), 3.40 (s, 2H, $CH_2$), 1.59 (m, 2H, $COOCCH_2$), 1.32 (m, 14H, $CH_2$), 0.83 (m, 3H, $CH_3$)

[Chemical Formula 64]

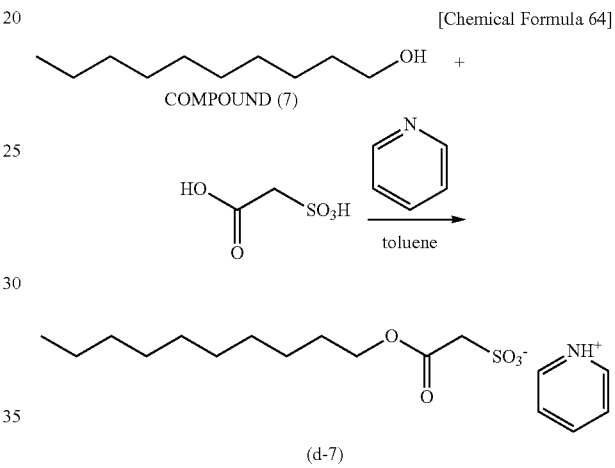

The obtained compound (d-7) was subjected to salt exchange in the same manner as in Synthesis Example 1 to obtain a compound (D)-7. The obtained compound (D)-7 was analyzed by NMR, and the structure thereof was identified. The results are shown in Table 2.

The same procedure as in Synthesis Example 1 was performed, except that the cation moiety of the compound (D)-1 was changed to a cation moiety shown in following Tables (in equimolar amount), thereby obtaining compounds (D)-8 to (D)-30. The results of the NMR analysis and structure of the compounds (D)-8 to (D)-30 are shown in Tables 3 to 10.

TABLE 1

| COMPOUND | N M R | CATION | PRODUCT |
|---|---|---|---|
| (D)-2 | $^1$H-NMR (400 MHz, dmso-d6): δ (ppm) = 7.60-8.10 (m, 15H, Phenyl), 5.30 (d, 1H, Oxosultone), 4.60-4.90 (m, 3H, oxosultone), 4.30 (s, 1H, oxosultone), 3.40 (s, 2H, $CH_2$), 2.10-2.30 (m, 2H, oxosultone) | | |

TABLE 1-continued

| COMPOUND | NMR | CATION | PRODUCT |
|---|---|---|---|
| (D)-3 | $^1$H-NMR (400 MHz, dmso-d6): δ (ppm) = 7.60-8.10 (m, 15H, Phenyl), 4.30 (m, 2H, Norbornane), 3.50 (m, 2H, CH$_2$), 3.11 (s, 1H, Norbornane), 2.40 (m, 2H, Norbornane), 1.90 (m, 2H, Norbornane), 1.52 (m, 2H, Norbornane) | triphenylsulfonium | norbornane lactone ester with –OCH$_2$SO$_3^−$ anion; triphenylsulfonium cation |
| (D)-4 | $^1$H-NMR (400 MHz, dmso-d6): δ (ppm) = 7.60-8.10 (m, 15H, Phenyl), 5.49 (s, 1H, Oxonorbornane), 4.98 (s, 1H, Oxonorbornane), 4.70 (s, 1H, Oxonorbornane), 4.58 (s, 1H, Oxonorbornane), 3.50 (m, 2H, CH$_2$), 2.71 (s, 1H, Oxonorbornane), 2.11 (m, 2H, Oxonorbornane) | triphenylsulfonium | oxonorbornane lactone ester with –OCH$_2$SO$_3^−$ anion; triphenylsulfonium cation |

TABLE 2

| COMPOUND | NMR | CATION | PRODUCT |
|---|---|---|---|
| (D)-5 | $^1$H-NMR (400 MHz, dmso-d6): δ (ppm) = 7.60-8.10 (m, 15H, Phenyl), 5.70 (t, 1H, OCHC=O), 4.46-4.30 (m, 2H, OCOCH$_2$), 3.50 (m, 2H, CH$_2$), 2.71-2.64 (m, 1H, OCH$_2$CH$_2$), 2.33-2.24 (m, 1H, OCH$_2$CH$_2$) | triphenylsulfonium | γ-butyrolactone ester with –OCH$_2$SO$_3^−$ anion; triphenylsulfonium cation |
| (D)-6 | $^1$H-NMR (400 MHz, dmso-d6): δ (ppm) = 7.60-8.10 (m, 15H, Phenyl), 4.80 (s, 1H, Adamantane), 3.80 (s, 2H, CH$_2$), 2.11 (d, 2H, Adamantane), 1.30-1.98 (m, 12H, Adamantane) | triphenylsulfonium | adamantyl ester with –OCH$_2$SO$_3^−$ anion; triphenylsulfonium cation |
| (D)-7 | $^1$H-NMR (400 MHz, dmso-d6): δ (ppm) = 7.60-8.10 (m, 15H, Phenyl), 3.99 (t, 2H, COOCH$_2$), 3.40 (s, 2H, CH$_2$), 1.59 (m, 2H, COOCCH$_2$), 1.32 (m, 14H, CH$_2$), 0.83 (m, 3H, CH$_3$) | triphenylsulfonium | decyl ester with –OCH$_2$SO$_3^−$ anion; triphenylsulfonium cation |

TABLE 3

| COMPOUND | NMR | CATION | PRODUCT |
|---|---|---|---|
| (D)-8 | ¹H-NMR (400 MHz, dmso-d6): δ (ppm) = 8.50 (d, 2H, ArH), 8.37 (d, 2H, ArH), 7.93 (t, 2H, ArH), 7.55-7.75 (m, 7H, ArH), 4.80 (d, 1H, Sultone), 4.50 (s, 1H, Sultone), 3.90 (m, 1H, Sultone), 3.40-3.80 (m, 3H, Sultone + CH$_2$), 2.40 (s, 1H, Sultone), 1.70-2.20 (m, 4H, Sultone) | 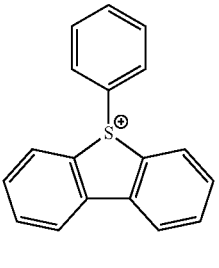 [SMILES: c1ccc(-[s+]2c3ccccc3c3ccccc32)cc1] | 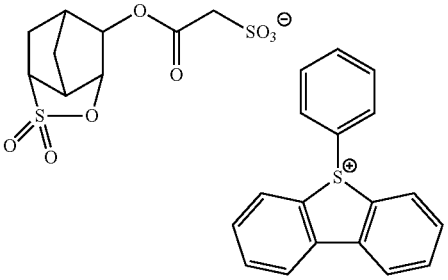 |
| (D)-9 | ¹H-NMR (400 MHz, dmso-d6): δ (ppm) = 10.05 (s, 1H, OH), 7.64.-7.87 (m, 10H, ArH), 7.56 (s, 2H, ArH), 4.80 (d, 1H, Sultone), 4.50 (s, 1H, Sultone), 3.90 (m, 1H, Sultone), 3.40-3.80 (m, 3H, Sultone + CH$_2$), 2.40 (s, 1H, Sultone), 1.70-2.20 (m, 10H, CH$_3$ + Sultone) | 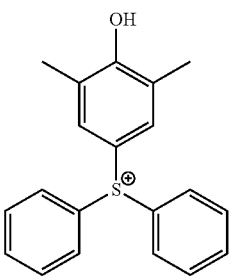 [SMILES: Cc1cc([S+](c2ccccc2)c2ccccc2)cc(C)c1O] | 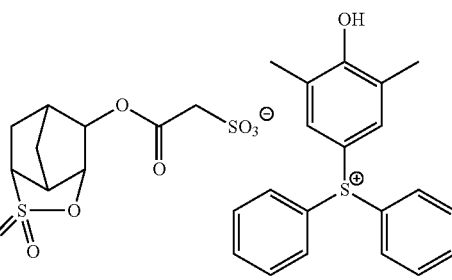 |
| (D)-10 | ¹H-NMR (400 MHz, dmso-d6): δ (ppm) = 7.71-7.89 (m, 10H, ArH), 7.59 (s, 2H, ArH), 4.80 (d, 1H, Sultone), 4.52 (m, 3H, Sultone + CH$_2$), 3.90 (m, 1H, Sultone), 3.40-3.80 (m, 3H, Sultone + CH$_2$), 2.40 (s, 1H, Sultone), 2.30 (s, 6H, ArCH$_3$), 1.70-2.20 (m, 4H, Sultone) | 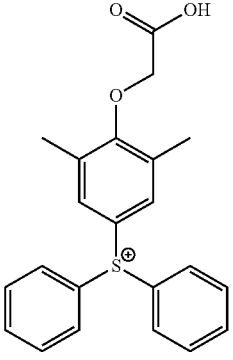 [SMILES: Cc1cc([S+](c2ccccc2)c2ccccc2)cc(C)c1OCC(=O)O] | 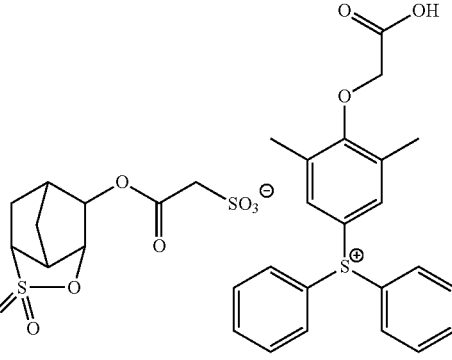 |

TABLE 4

| COMPOUND | NMR | CATION | PRODUCT |
|---|---|---|---|
| (D)-11 | ¹H-NMR (400 MHz, dmso-d6): δ (ppm) = 7.73-7.85 (m, 10H, ArH), 7.59 (S, 2H, ArH), 4.80 (d, 1H, Sultone), 4.50 (s, 1H, Sultone), 3.90 (m, 1H, Sultone), 3.40-3.83 (m, 5H, Sultone + CH$_2$ + OCH$_2$), 2.40 (m, 7H, Sultone + CH$_3$), 1.70-2.20 (m, 4H, Sultone), 1.45 (m, 4H, CH$_2$), 1.29 (m, 4H, CH$_2$), 0.87 (t, 3H, CH$_3$) | 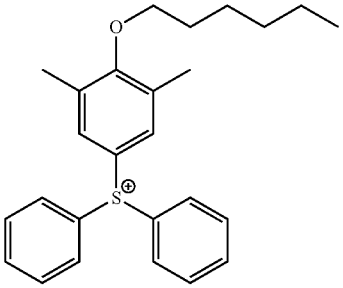 [SMILES: CCCCCCOc1c(C)cc([S+](c2ccccc2)c2ccccc2)cc1C] | 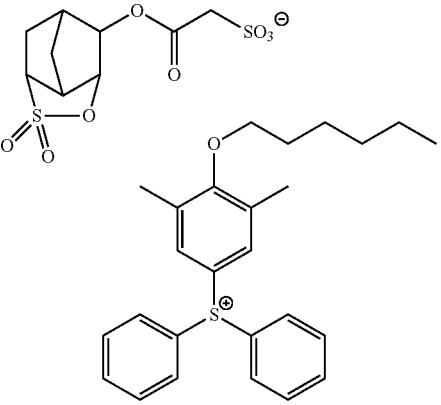 |

TABLE 4-continued

| COMPOUND | NMR | CATION | PRODUCT |
|---|---|---|---|
| (D)-12 | ¹H-NMR (400 MHz, dmso-d6): δ (ppm) = 8.53 (d, 2H, ArH), 8.27 (d, 2H, ArH), 7.95 (t, 2H, ArH), 7.74 (t, 2H, ArH), 7.20 (s, 1H, ArH), 6.38 (s, 1H, ArH), 4.80 (d, 1H, Sultone), 4.50 (s, 1H, Sultone), 4.02 (m, 3H, cation-OCH$_2$ + Sultone), 3.40-3.80 (m, 3H, Sultone + CH$_2$), 2.86 (s, 3H, ArCH$_3$), 2.40 (s, 1H, Sultone), 1.70-2.20 (m, 9H, Sultone + ArCH$_3$ + CH$_2$), 1.37 (quin, 2H, CH$_2$), 1.24-1.26 (m, 4H, CH$_2$), 0.82 (t, 3H, CH$_3$) | | |
| (D)-13 | ¹H-NMR (400 MHz, dmso-d6): δ (ppm) = 7.99-8.01 (d, 2H, Ar), 7.73-7.76 (t, 1H, Ar), 7.58-7.61 (t, 2H, Ar), 5.31 (s, 2H, SCH$_2$C=O), 4.80 (d, 1H, Sultone), 4.50 (s, 1H, Sultone), 3.90 (m, 1H, Sultone), 3.40-3.80 (m, 7H, Sultone + CH$_2$ + CH$_2$), 1.70-2.49 (m, 9H, CH$_2$S + Sultone) | | |

TABLE 5

| COMPOUND | NMR | CATION | PRODUCT |
|---|---|---|---|
| (D)-14 | ¹H-NMR (400 MHz, dmso-d6): δ (ppm) = 8.02-8.05 (m, 2H, Phenyl), 7.61-7.73 (m, 3H, Phenyl), 4.80 (d, 1H, Sultone), 4.50 (s, 1H, Sultone), 3.90 (m, 1H, Sultone), 3.76-3.86 (m, 7H, SCH$_2$ + Sultone + CH$_2$), 2.40 (s, 1H, Sultone), 1.61-2.19 (m, 10H, CH$_2$ + Sultone) | | |
| (D)-15 | ¹H-NMR (400 MHz, dmso-d6): δ (ppm) = 8.04-8.09 (m, 2H, Phenyl), 7.69-7.79 (m, 3H, Phenyl), 4.80 (d, 1H, Sultone), 4.50 (s, 1H,Sultone), 3.90 (m, 1H, Sultone), 3.40-3.80 (m, 3H, Sultone + CH$_2$), 3.29 (s, 6H, CH$_3$), 2.40 (s, 1H, Sultone), 1.70-2.20 (m, 4H, Sultone) | | |

TABLE 5-continued

| COMPOUND | N M R | CATION | PRODUCT |
|---|---|---|---|
| (D)-16 | ¹H-NMR (400 MHz, dmso-d6): δ (ppm) = 8.07 (d, 2H, Phenyl), 7.81 (d, 2H, Phenyl), 4.80 (d, 1H, Sultone), 4.50 (s, 1H, Sultone), 4.10 (t, 2H, CH$_2$), 3.90 (m, 1H, Sultone), 3.40-3.80 (m, 5H, Sultone + CH$_2$), 2.40 (s, 1H, Sultone), 1.69-2.20 (m, 6H, CH$_2$ + Sultone), 1.23 (s, 9H, t-Bu) | | |

TABLE 6

| COMPOUND | CATION | PRODUCT | NMR |
|---|---|---|---|
| (D)-17 | | | ¹H-NMR (400 MHz, dmso-d6): δ (ppm) = 7.84 (d, 6H, ArH), 7.78 (d, 6H, ArH), 4.80 (d, 1H, Sultone), 4.50 (s, 1H, Sultone), 3.90 (m, 1H, Sultone), 3.40-3.80 (m, 3H, Sultone + CH₂), 2.40 (s, 1H, Sultone), 1.70-2.20 (m, 4H, Sultone), 1.33 (s, 27H, tBu-CH₃) |
| (D)-18 | | | ¹H-NMR (400 MHz, dmso-d6): δ (ppm) = 7.76-7.87 (m, 10H, ArH), 7.69 (s, 2H, ArH), 4.80 (d, 1H, Sultone), 4.50 (s, 1H, Sultone), 3.90 (m, 1H, Sultone), 3.40-3.80 (m, 3H, Sultone + CH₂), 2.40 (s, 1H, Sultone), 1.66-2.21 (m, 25H, ArCH3 + adamantyl + Sultone) |
| (D)-19 | | | ¹H-NMR (400 MHz, dmso-d6): δ (ppm) = 7.79-7.93 (m, 12H, ArH), 4.80 (d, 1H, Sultone), 4.50 (s, 1H, Sultone), 3.90 (m, 1H, Sultone), 3.40-3.80 (m, 3H, Sultone + CH₂), 2.73 (t, 2H, CO—CH₂), 2.40 (s, 1H, Sultone), 1.65-2.22 (m, 12H, ArCH₃ + CH₂ + Sultone), 1.25-1.38 (m, 14H, CH₂), 0.85 (t, 3H, CH₃) |

TABLE 7

| COMPOUND | N M R | CATION | PRODUCT |
|---|---|---|---|
| (D)-20 | ¹H-NMR (400 MHz, dmso-d6): δ (ppm) = 4.80 (d, 1H, Sultone), 4.50 (s, 1H, Sultone), 3.90 (m, 1H, Sultone), 3.40-3.80 (m, 3H, Sultone + CH₂), 3.36 (t, 6H, CH₂), 2.40 (s, 1H, Sultone), 1.68-2.20 (m, 10H, CH₂ + Sultone), 1.35-1.44 (m, 6H, CH₂), 0.81-0.93 (m, 9H, CH₃) | 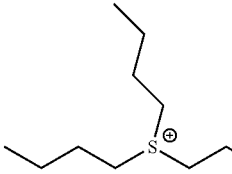 | 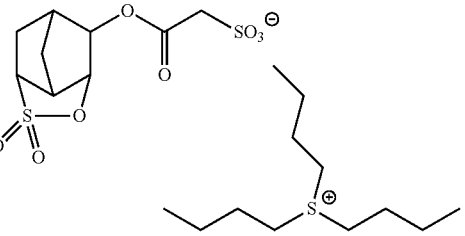 |
| (D)-21 | ¹H-NMR (400 MHz, dmso-d6): δ (ppm) = 9.73 (br s, 1H, OH), 8.47 (d, 2H, ArH), 8.24 (d, 2H, ArH), 7.91 (t, 2H, ArH), 7.71 (t, 2H, ArH), 7.18 (s, 2H, ArH), 4.80 (d, 1H, Sultone), 4.50 (s, 1H, Sultone), 3.90 (m, 1H, Sultone), 3.40-3.80 (m, 3H, Sultone + CH₂), 2.40 (s, 1H, Sultone), 1.70-2.20 (m, 10H, Sultone + ArCH₃) | 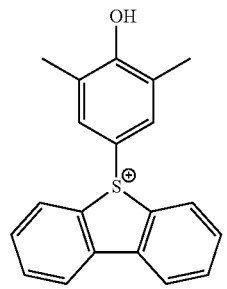 [SMILES: Cc1cc(-[s+]2c3ccccc3c3ccccc32)cc(C)c1O] | 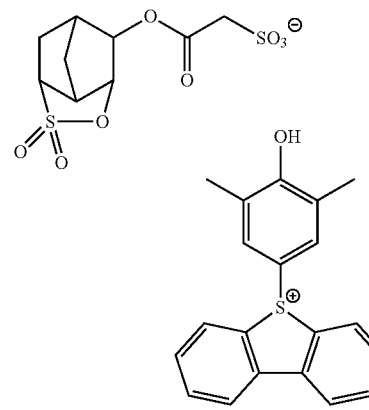 |
| (D)-22 | ¹H-NMR (400 MHz, dmso-d6): δ (ppm) = 8.44 (d, 1H, ArH), 8.22 (m, 2H, ArH), 7.73-7.89 (m, 13H, ArH), 7.50 (d, 1H, ArH), 4.80 (d, 1H, Sultone), 4.50 (s, 1H, Sultone), 3.90 (m, 1H, Sultone), 3.40-3.80 (m, 3H, Sultone + CH₂), 2.40 (s, 1H, Sultone), 1.70-2.20 (m, 4H Sultone) | 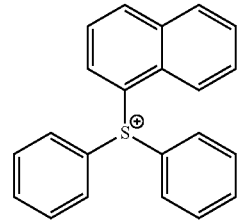 [SMILES: c1ccc([S+](c2ccccc2)c2cccc3ccccc23)cc1] | 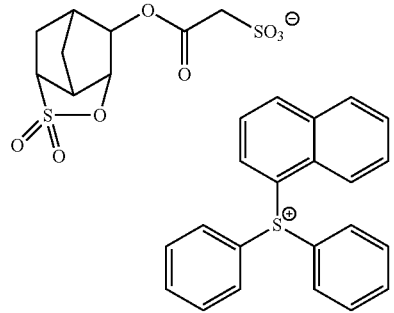 |

TABLE 8

| COMPOUND | N M R | CATION | PRODUCT |
|---|---|---|---|
| (D)-23 | ¹H-NMR (400 MHz, dmso-d6): δ (ppm) = 8.24 (d, 4H, ArH), 7.59 (t, 2H, ArH), 7.47 (t, 4H, ArH), 4.80 (d, 1H, Sultone), 4.50 (s, 1H, Sultone), 3.90 (m, 1H, Sultone), 3.40-3.80 (m, 3H, Sultone + CH₂), 2.40 (s, 1H, Sultone), 1.70-2.20 (m, 4H, Sultone) | 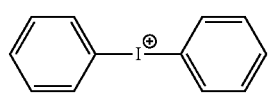 [SMILES: c1ccc([I+]c2ccccc2)cc1] | 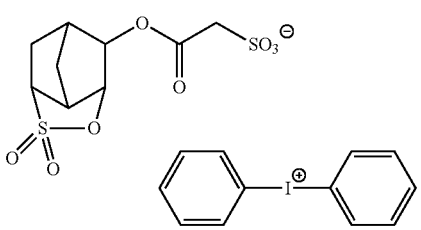 |

TABLE 8-continued

| COMPOUND | NMR | CATION | PRODUCT |
|---|---|---|---|
| (D)-24 | ¹H-NMR (400 MHz, dmso-d6): δ (ppm) = 8.55 (d, 2H, ArH), 8.38 (d, 2H, ArH), 8.32 (d, 2H, ArH), 8.03 (d, 2H, ArH), 7.93-7.97 (m, 1H, ArH), 7.82-7.88 (m, 8H, ArH), 7.55 (d, 2H, ArH), 4.80 (d, 1H, Sultone), 4.50 (s, 1H, Sultone), 3.90 (m, 1H, Sultone), 3.40-3.80 (m, 3H, Sultone + CH₂), 2.40 (s, 1H, Sultone), 1.70-2.20 (m, 4H, Sultone) | | |
| (D)-25 | ¹H-NMR (400 MHz, dmso-d6): δ (ppm) = 4.80 (d, 1H, Sultone), 4.50 (s, 1H, Sultone), 4.46 (s, 2H, CH₂ (C=O)), 3.90 (m, 1H, Sultone), 3.40-3.80 (m, 7H, Sultone + CH₂ + CH₂SCH₂), 2.40 (s, 1H, Sultone), 1.56-2.33 (m, 25H, Ad + CH₂CH₂ + Sultone) | | |

TABLE 9

| COMPOUND | NMR | CATION | PRODUCT |
|---|---|---|---|
| (D)-26 | ¹H-NMR (400 MHz, dmso-d6): δ (ppm) = 7.75 (s, 2H, Ar), 4.80 (d, 1H, Sultone), 4.50 (s, 1H, Sultone), 3.91-3.96 (m, 3H, CH₂ + Sultone), 3.40-3.80 (m, 5H, Sultone + CH₂), 2.29-2.41 (m, 5H, CH₂ + Sultone), 1.75-2.19 (m, 25H, Ar—CH₃ + adamantyl + Sultone) | | |

TABLE 9-continued

| COMPOUND | N M R | CATION | PRODUCT |
|---|---|---|---|
| (D)-27 | ¹H-NMR (400 MHz, dmso-d6): δ (ppm) = 7.82 (m, 2H, ArH), 4.80 (d, 1H, Sultone), 4.50 (s, 1H, Sultone), 3.73-3.91 (m, 5H, SCH$_2$ + Sultone), 3.40-3.80 (m, 3H, Sultone + CH$_2$), 1.56-2.43 (m, 32H, Ar—CH$_3$ + CH$_2$ + adamantyl + Sultone) | | |

TABLE 10

| COMPOUND | N M R | CATION | PRODUCT |
|---|---|---|---|
| (D)-28 | ¹H-NMR (400 MHz, dmso-d6): δ (ppm) = 8.28 (d, 2H, ArH), 8.11 (d, 1H, ArH), 7.86 (t, 1H, ArH), 7.63-7.81 (m, 7H, ArH), 4.80 (d, 1H, Sultone), 4.50 (s, 1H, Sultone), 3.90 (m, 1H, Sultone), 3.40-3.80 (m, 3H, Sultone + CH$_2$), 2.40 (s, 1H, Sultone), 1.70-2.20 (m, 4H, Sultone) | | |
| (D)-29 | ¹H-NMR (400 MHz, dmso-d6): δ (ppm) = 8.05 (d, 2H, ArH), 7.74 (d, 2H, ArH), 4.80 (d, 1H, Sultone), 4.50 (s, 1H, Sultone), 3.90 (m, 1H, Sultone), 3.40-3.80 (m, 6H, Sultone + CH$_2$ + S—CH$_3$), 2.40 (s, 1H, Sultone), 1.70-2.20 (m, 4H, Sultone), 1.30 (s, 18H, t-Bu) | | |

TABLE 10-continued

| COMPOUND | NMR | CATION | PRODUCT |
|---|---|---|---|
| (D)-30 | $^1$H-NMR (400 MHz, dmso-d6): δ (ppm) = 8.28 (d, 2H, ArH), 8.12 (d, 1H, ArH), 7.88 (t, 1H, ArH), 7.80 (d, 1H, ArH), 7.62-7.74 (m, 5H, ArH), 4.80 (d, 1H, Sultone), 4.50 (s, 1H, Sultone), 3.90 (m, 1H, Sultone), 3.40-3.80 (m, 3H, Sultone + CH$_2$), 2.40 (s, 1H, Sultone), 1.70-2.20 (m, 4H, Sultone), 1.27 (s, 9H, CH$_3$) | 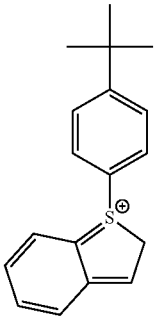 | 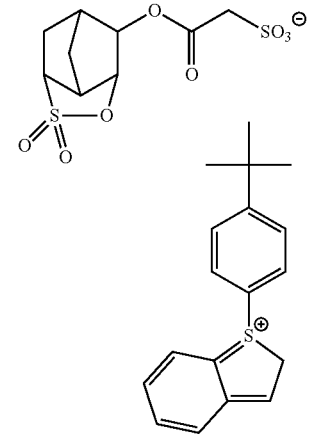 |

The components were mixed with the obtained compound (D)-1 to (D)-7, (D)-31 and (D)-32 in the mixing ratio indicated in following Tables 11 and 12 to obtain resist compositions (Examples 1 to 19, Comparative Examples 1 to 5).

TABLE 11

| | COMPONENT (A) | COMPONENT (B) | COMPONENT (D) | COMPONENT (E) | COMPONENT (F) | COMPONENT (S) |
|---|---|---|---|---|---|---|
| EXAMPLE 1 | (A)-1 [100] | (B)-1 [14.5] | (D)-1 [6.9] | (E)-1 [2.9] | (F)-1 [3] | (S)-1 [4485] |
| EXAMPLE 2 | (A)-1 [100] | (B)-1 [14.5] | (D)-2 [7.1] | (E)-1 [2.9] | (F)-1 [3] | (S)-1 [4485] |
| EXAMPLE 3 | (A)-1 [100] | (B)-1 [14.5] | (D)-3 [6.5] | (E)-1 [2.9] | (F)-1 [3] | (S)-1 [4485] |
| EXAMPLE 4 | (A)-1 [100] | (B)-1 [14.5] | (D)-4 [6.5] | (E)-1 [2.9] | (F)-1 [3] | (S)-1 [4485] |
| EXAMPLE 5 | (A)-1 [100] | (B)-1 [14.5] | (D)-5 [5.8] | (E)-1 [2.9] | (F)-1 [3] | (S)-1 [4485] |
| EXAMPLE 6 | (A)-1 [100] | (B)-1 [14.5] | (D)-6 [5.6] | (E)-1 [2.9] | (F)-1 [3] | (S)-1 [4485] |
| EXAMPLE 7 | (A)-1 [100] | (B)-1 [14.5] | (D)-7 [6.5] | (E)-1 [2.9] | (F)-1 [3] | (S)-1 [4485] |
| EXAMPLE 8 | (A)-2 [100] | (B)-1 [14.5] | (D)-1 [6.9] | (E)-1 [2.9] | (F)-1 [3] | (S)-1 [4485] |
| EXAMPLE 9 | (A)-2 [100] | (B)-1 [14.5] | (D)-6 [5.6] | (E)-1 [2.9] | (F)-1 [3] | (S)-1 [4485] |
| EXAMPLE 10 | (A)-3 [100] | (B)-1 [14.5] | (D)-1 [6.9] | (E)-1 [2.9] | (F)-1 [3] | (S)-1 [4485] |
| EXAMPLE 11 | (A)-3 [100] | (B)-1 [14.5] | (D)-6 [5.6] | (E)-1 [2.9] | (F)-1 [3] | (S)-1 [4485] |
| EXAMPLE 12 | (A)-4 [100] | (B)-1 [14.5] | (D)-6 [5.6] | (E)-1 [2.9] | (F)-1 [3] | (S)-1 [4485] |
| COMPARATIVE EXAMPLE 1 | (A)-1 [100] | (B)-1 [14.5] | (D)-31 [6.6] | (E)-1 [2.9] | (F)-1 [3] | (S)-1 [4485] |
| COMPARATIVE EXAMPLE 2 | (A)-1 [100] | (B)-1 [14.5] | (D)-32 [5.9] | (E)-1 [2.9] | (F)-1 [3] | (S)-1 [4485] |
| COMPARATIVE EXAMPLE 3 | (A)-3 [100] | (B)-1 [14.5] | (D)-32 [5.9] | (E)-1 [2.9] | (F)-1 [3] | (S)-1 [4485] |

TABLE 12

| | COMPONENT (A) | COMPONENT (B) | COMPONENT (D) | COMPONENT (E) | COMPONENT (F) | COMPONENT (S) |
|---|---|---|---|---|---|---|
| EXAMPLE 13 | (A)-5 [100] | (B)-1 [6.0] | (D)-1 [5.98] | (E)-1 [0.2] (E)-2 [100] | (F)-1 [4.0] | (S)-1 [4485] |
| EXAMPLE 14 | (A)-5 [100] | (B)-1 [6.0] | (D)-2 [6.00] | (E)-1 [0.2] (E)-2 [100] | (F)-1 [4.0] | (S)-1 [4485] |
| EXAMPLE 15 | (A)-5 [100] | (B)-1 [6.0] | (D)-3 [5.61] | (E)-1 [0.2] (E)-2 [100] | (F)-1 [4.0] | (S)-1 [4485] |
| EXAMPLE 16 | (A)-5 [100] | (B)-1 [6.0] | (D)-4 [5.63] | (E)-1 [0.2] (E)-2 [100] | (F)-1 [4.0] | (S)-1 [4485] |

TABLE 12-continued

| | COMPONENT (A) | COMPONENT (B) | COMPONENT (D) | COMPONENT (E) | | COMPONENT (F) | COMPONENT (S) |
|---|---|---|---|---|---|---|---|
| EXAMPLE 17 | (A)-5 [100] | (B)-1 [6.0] | (D)-5 [5.07] | (E)-1 [0.2] | (E)-2 [100] | (F)-1 [4.0] | (S)-1 [4485] |
| EXAMPLE 18 | (A)-5 [100] | (B)-1 [6.0] | (D)-6 [5.59] | (E)-1 [0.2] | (E)-2 [100] | (F)-1 [4.0] | (S)-1 [4485] |
| EXAMPLE 19 | (A)-5 [100] | (B)-1 [6.0] | (D)-1 [5.65] | (E)-1 [0.2] | (E)-2 [100] | (F)-1 [4.0] | (S)-1 [4485] |
| COMPARATIVE EXAMPLE 4 | (A)-5 [100] | (B)-1 [6.0] | (D)-31 [5.73] | (E)-1 [0.2] | (E)-2 [100] | (F)-1 [4.0] | (S)-1 [4485] |
| COMPARATIVE EXAMPLE 5 | (A)-5 [100] | (B)-1 [6.0] | (D)-32 [5.15] | (E)-1 [0.2] | (E)-2 [100] | (F)-1 [4.0] | (S)-1 [4485] |

In Tables 11 and 12, the reference characters indicate the following. Further, the values in brackets [ ] indicate the amount (in terms of parts by weight) of the component added.

(A)-1: polymeric compound (A)-1 shown below l/m/n=45/35.1/19.9, Mw=6200, Mw/Mn=1.71

(A)-2: polymeric compound (A)-2 shown below l/m/n/o/p=35/24/16/13/12, Mw=7900, Mw/Mn=1.56

(A)-3: polymeric compound (A)-3 shown below l/m/n=45/35/20, Mw=6800, Mw/Mn=1.60

(A)-4: polymeric compound (A)-4 shown below l/m/n=45/35/20, Mw=6800, Mw/Mn=1.60

(A)-5: polymeric compound (A)-5 shown below l/m/n=30/60/10, Mw=7000, Mw/Mn=1.71

(B)-1: compound (B)-1 shown below (D)-1 to (D)-7 and (D)-31 to (D)-32: compounds (D)-1 to (D)-7 and (D)-31 to (D)-32 shown below (F)-1: polymeric compound (F)-1 shown below Mw=24000, Mw/Mn=1.38

(E)-1: salicylic acid (E)-2: γ-butyrolactone (S)-1: a mixed solvent of PGMEA/PGME/cyclohexanone=45/30/25 (weight ratio)

[Chemical Formula 65]

(A)-1

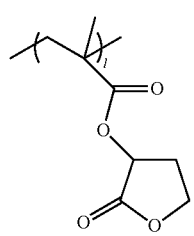
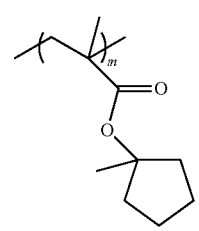
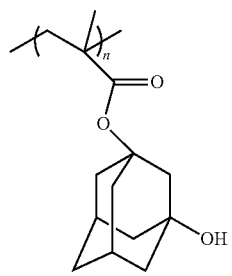

(A)-2

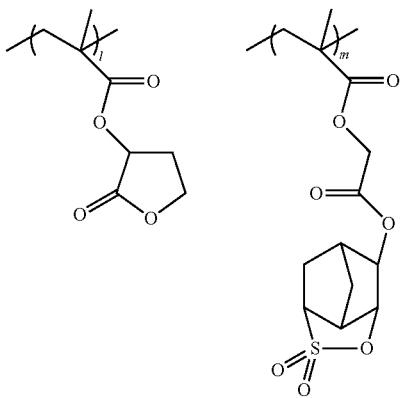

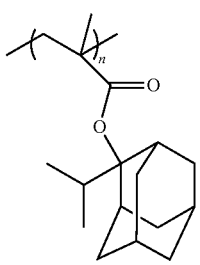
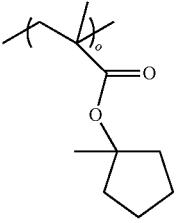

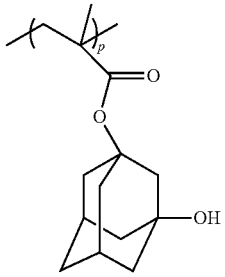

(A)-3

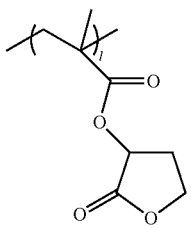

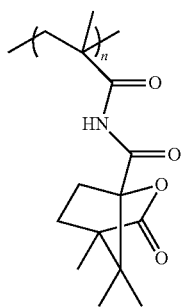
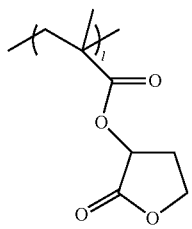
(A)-4
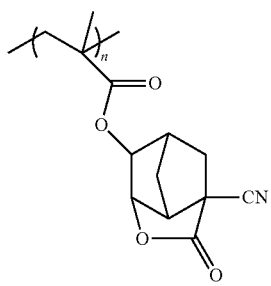
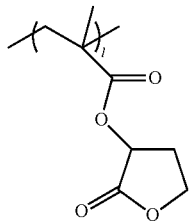
(A)-5
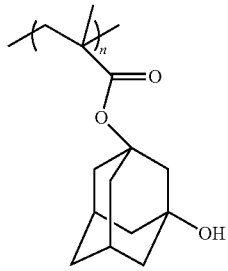
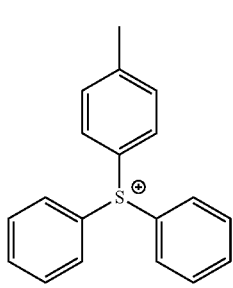
(B)-1
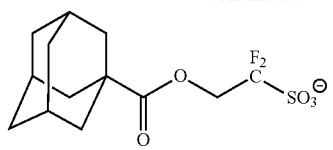
(F)-1
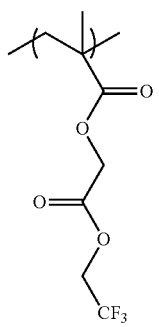
(D)-1
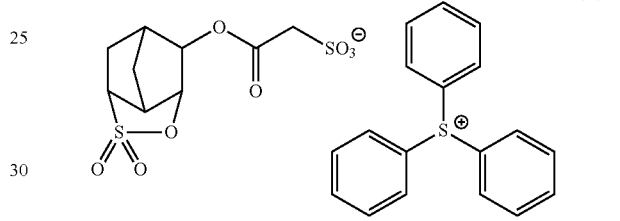
(D)-2
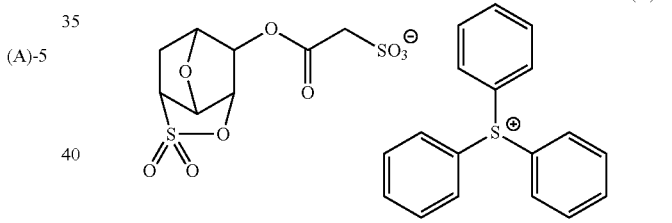
(D)-3
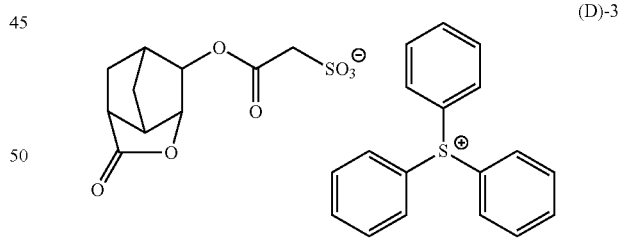
(D)-4
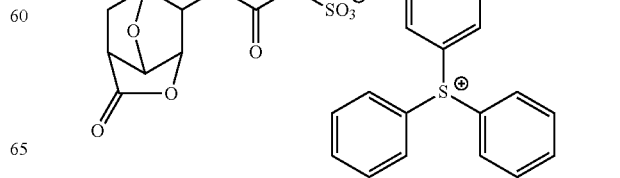

-continued

[Chemical Formula 66]

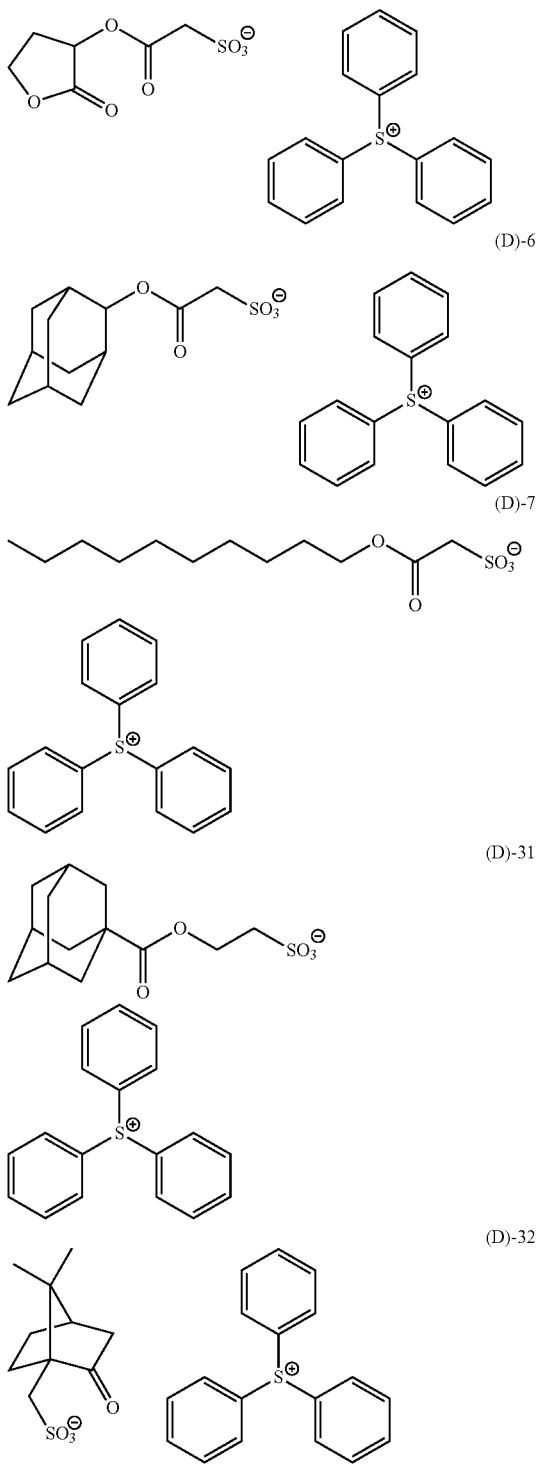

Formation of Resist Pattern

Examples 1 to 12, Comparative Examples 1 to 3

An organic anti-reflection film composition (product name: ARC95, manufactured by Brewer Science Ltd.) was applied to an 12-inch silicon wafer using a spinner, and the composition was then baked at 205° C. for 60 seconds and dried, thereby forming an organic anti-reflection film having a film thickness of 90 nm.

Then, each of the above resist composition indicated in Table 11 (Examples 1 to 9, Comparative Examples 1 and 2) was applied to the organic antireflection film using a spinner, and was then prebaked (PAB) on a hotplate at 100° C. for 60 seconds and dried, thereby forming a resist film having a film thickness of 80 nm.

Subsequently, the resist film was selectively irradiated with an ArF excimer laser (193 nm) through a photomask (6% halftone), using an immersion lithography ArF exposure apparatus NSR-S609B (manufactured by Nikon Corporation; NA (numerical aperture)=1.07; Dipole (in/out=0.78/0.97) with Polano; immersion medium: water).

Further, PEB treatment was conducted at 95° C. for 60 seconds.

Next, an alkali development was conducted for 10 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist was washed for 30 seconds with pure water, followed by drying by shaking.

As a result, in each of the examples, a 1:1 line and space pattern (LS pattern) having a line width of 50 nm and a pitch of 100 nm was formed.

Formation of Resist Pattern

Examples 13 to 19, Comparative Examples 4 and 5

An organic anti-reflection film composition (product name: ARC95, manufactured by Brewer Science Ltd.) was applied to a 12-inch silicon wafer using a spinner, thereby forming an organic anti-reflection film having a film thickness of 72 nm. Then, an inorganic anti-reflection film composition (product name: ARC212, manufactured by Brewer Science Ltd.) was applied to the organic anti-reflection film using a spinner, thereby laminating an inorganic anti-reflection film having a film thickness of 14 nm.

Each of the resist compositions was then applied to the inorganic anti-reflection film using a spinner, and was then prebaked (PAB) on a hotplate at 110° C. for 50 seconds and dried, thus forming a resist film having a film thickness of 85 nm.

Subsequently, the resist film was selectively irradiated with an ArF excimer laser (193 nm) through a photomask (OCD-LS3, Middle Bright), using an immersion lithography ArF exposure apparatus NSR-5609B (manufactured by Nikon Corporation; NA (numerical aperture)=1.07; Annular (0.97/0.78) with Y-Polarization; immersion medium: water).

Further, a post exposure bake (PEB) treatment was conducted at 95° C. for 50 seconds.

Next, a solvent development was conducted for 31 seconds at 23° C. using butyl acetate, followed by drying by shaking.

As a result, in each of the examples, a space and line pattern (hereafter, referred to as "SL pattern") having a space width of 47 nm and a pitch of 110 nm was formed.

Evaluation of Resist Pattern

Examples 1 to 12, Comparative Examples 1 to 3

Evaluation of Mask Error Factor (MEEF)

In the same manner as in the formation of LS pattern, with the same exposure dose, LS patterns with a pitch of 100 nm were formed using a mask pattern targeting a line pattern size of 45 to 54 nm (10 target sizes at intervals of 1 nm). The value of the mask error factor (MEEF) was determined as the gradient of a graph obtained by plotting the target size (nm) on the horizontal axis, and the size (nm) of the formed line patterns on the vertical axis. A MEEF value (gradient of the plotted line) closer to 1 indicates that a resist pattern faithful to the mask pattern was formed. The results are shown in Table 13.

[Evaluation of Line Width Roughness (LWR)]

With respect to each of the LS patterns, the space width at 400 points in the lengthwise direction of the space was measured using a measuring scanning electron microscope (SEM) (product name: S-9380, manufactured by Hitachi High-Technologies Corporation; acceleration voltage: 300V). From the results, the value of 3 times the standard deviation s (i.e., 3 s) was determined, and the average of the 3 s values at 400 points was calculated as a yardstick of LWR. The results are shown in Table 13.

The smaller this 3 s value is, the lower the level of roughness of the line width, indicating that a LS pattern with a uniform width was obtained.

[Evaluation of Exposure Latitude (EL Margin)]

In the aforementioned formation of an LS pattern, the exposure dose with which an LS pattern having a dimension of the target dimension ±5% was formed, was determined, and the EL margin (unit: %) was determined by the following formula. The results are shown in Table 13.

EL margin (%)=(|E1−E2|/Eop)×100

E1: Exposure dose (mJ/cm$^2$) with which an LS pattern having a line width of 47.5 nm was formed E2: Exposure dose (mJ/cm$^2$) with which an LS pattern having a line width of 52.5 nm was formed.

The larger the value of the "EL margin", the smaller the change in the pattern size by the variation of the exposure dose.

In the aforementioned formula for calculating EL margin, the "Eop" means the optimum exposure dose (mJ/cm$^2$). Eop was determined by a conventional method.

Evaluation of Resist Pattern

Examples 13 to 19, Comparative Examples 4 to 6

Evaluation of Mask Error Factor (MEEF)

In the same manner as in the formation of SL pattern, with the same exposure dose, SL patterns with a pitch of 110 nm were formed using a mask pattern targeting a line pattern size of 43 to 52 nm (10 target sizes at intervals of 1 nm). The value of the mask error factor (MEEF) was determined as the gradient of a graph obtained by plotting the target size (nm) on the horizontal axis, and the size (nm) of the formed space patterns on the vertical axis. A MEEF value (gradient of the plotted line) closer to 1 indicates that a resist pattern faithful to the mask pattern was formed.

The results are shown in Table 14.

[Evaluation of Line Width Roughness (LWR)]

With respect to each of the SL patterns, the space width at 400 points in the lengthwise direction of the space was measured using a measuring scanning electron microscope (SEM) (product name: S-9380, manufactured by Hitachi High-Technologies Corporation; acceleration voltage: 300V). From the results, the value of 3 times the standard deviation s (i.e., 3 s) was determined, and the average of the 3 s values at 400 points was calculated as a yardstick of LWR. The results are shown in Table 14.

The smaller this 3 s value is, the lower the level of roughness of the line width, indicating that an SL pattern with a uniform width was obtained.

[Evaluation of Exposure Latitude (EL Margin)]

In the aforementioned formation of SL pattern, the exposure dose with which an SL pattern having a dimension of the target dimension ±5% was formed, was determined, and the EL margin (unit: %) was determined by the following formula. The results are indicated "5% EL" in Table 14.

EL margin (%)=(|E1−E2|/Eop)×100

In the formula, E1 represents the exposure dose (mJ/cm$^2$) for forming an SL pattern having a line width of 44.5 nm, and E2 represents the exposure dose (mJ/cm$^2$) for forming an SL pattern having a line width of 49.5 nm.

The larger the value of the "EL margin", the smaller the change in the pattern size by the variation of the exposure dose.

In the aforementioned formula for calculating EL margin, the "Eop" means the optimum exposure dose (mJ/cm$^2$). Eop was determined by a conventional method.

TABLE 13

| | Eop (mJ/cm$^2$) | EL MARGIN (%) | LWR (nm) | MEEF |
|---|---|---|---|---|
| EXAMPLE 1 | 20.4 | 8.56 | 2.87 | 1.56 |
| EXAMPLE 2 | 20.5 | 8.71 | 2.88 | 1.56 |
| EXAMPLE 3 | 21.0 | 8.76 | 2.70 | 1.54 |
| EXAMPLE 4 | 21.1 | 8.77 | 2.68 | 1.52 |
| EXAMPLE 5 | 19.0 | 8.54 | 2.85 | 1.51 |
| EXAMPLE 6 | 19.1 | 8.45 | 2.86 | 1.55 |
| EXAMPLE 7 | 19.0 | 8.60 | 2.90 | 1.56 |
| EXAMPLE 8 | 29.1 | 9.88 | 4.19 | 1.49 |
| EXAMPLE 9 | 27.3 | 9.9 | 4.1 | 1.48 |
| EXAMPLE 10 | 15.0 | 9.12 | 3.01 | 1.52 |
| EXAMPLE 11 | 14.0 | 9.21 | 2.92 | 1.49 |
| EXAMPLE 12 | 19.0 | 7.70 | 2.95 | 1.55 |
| COMPARATIVE EXAMPLE 1 | 23.2 | 8.10 | 3.15 | 1.60 |
| COMPARATIVE EXAMPLE 2 | 22.3 | 8.40 | 2.91 | 1.58 |
| COMPARATIVE EXAMPLE 3 | 18.9 | 8.7 | 3.11 | 1.56 |

TABLE 14

| | Eop (mJ/cm$^2$) | EL MARGIN (%) | LWR (nm) | MEEF |
|---|---|---|---|---|
| EXAMPLE 13 | 24.1 | 3.23 | 2.81 | 2.19 |
| EXAMPLE 14 | 24.2 | 3.25 | 2.85 | 2.11 |
| EXAMPLE 15 | 23.9 | 3.24 | 2.79 | 2.21 |
| EXAMPLE 16 | 24.5 | 3.31 | 2.81 | 2.18 |
| EXAMPLE 17 | 24.1 | 3.30 | 2.82 | 2.24 |
| EXAMPLE 18 | 21.7 | 3.19 | 2.75 | 2.28 |
| EXAMPLE 19 | 19.8 | 3.16 | 2.83 | 2.30 |
| COMPARATIVE EXAMPLE 4 | 25.7 | 3.15 | 2.85 | 2.33 |
| COMPARATIVE EXAMPLE 5 | 27.1 | 3.10 | 2.91 | 2.31 |

By using the resist composition of the present invention, lithography properties such as Eop, LWR and MEEF were improved. It was confirmed that, when the polymeric compounds (A)-1 to (A)-3 and (A)-5 were used, EL margin was also improved.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates acid upon exposure and exhibits changed solubility in a developing solution under action of acid, comprising:
   a base component (A) which exhibits changed solubility in a developing solution under action of acid;
   an acid generator component (B) comprising a compound represented by general formula (b-1) shown below:

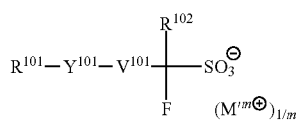
(b-1)

wherein the $R^{101}\text{—}Y^{101}\text{—}V^{101}\text{—}CR^{102}F\text{—}SO_3^-$ in the general formula (b-1) is at least one anion moiety represented by any one of formulae (an-1) to (an-3) shown below:

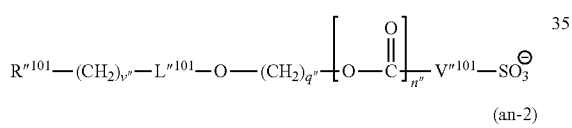
(an-1)

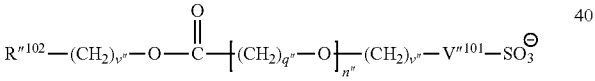
(an-2)

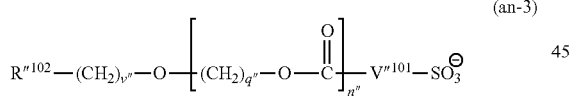
(an-3)

wherein $M'^{m+}$ resents an organic cation having a valency of m; $R''^{101}$ represents an aliphatic cyclic group which may have a substituent, a group represented by any one of formulae (r-hr-1) to (r-hr-6) shown below or a chain-like alkyl group which may have a substituent; $R''^{102}$ represents an aliphatic cyclic group which may have a substituent, a lactone-containing cyclic got represented by any one of formulae (a2-r-1) to (a2-r-7) shown below or an —SO₂— containing cyclic group represented by an one of formulae (a5-r-1) to (a5-r-4) shown below; $R''^{103}$ represents an aromatic cyclic group which may have a substituent, an aliphatic cyclic group which may have a substituent or a chain-like alkenyl group which ma have a substituent $V'''^{101}$ represents a fluorinated alkylene group; $L''^{101}$ represents —C(=O)— or —SO₂—; v" each independently represents an integer of 0 to 3; q" each independently represents an integer of 1 to 20; and n" represents 0 or 1:

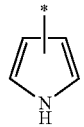
(r-hr-1)

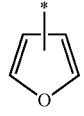
(r-hr-2)

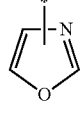
(r-hr-3)

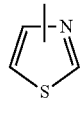
(r-hr-4)

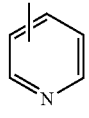
(r-hr-5)

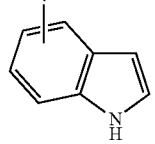
(r-hr-6)

wherein * represents a valence bond:

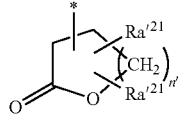
(a2-r-1)

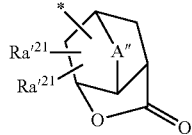
(a2-r-2)

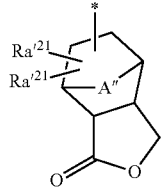
(a2-r-3)

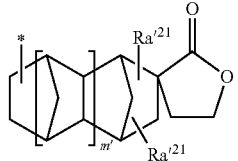
(a2-r-4)

-continued

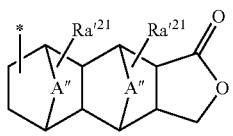 (a2-r-5)

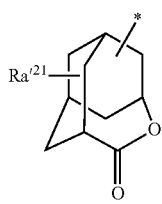 (a2-r-6)

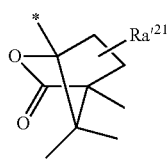 (a2-r-7)

wherein each $Ra'^{21}$ independently represents a hydrogen atom, an alkyl group, an alkoxy group, a halogen atom, a halogenated alkyl group, a hydroxy group, —COOR″—OC(=O)R″, a hydroxyalkyl group or a cyano group; R″ represents a hydrogen atom or an alkyl group; A″ represents an oxygen atom, a sulfur atom or an alkylene group of 1 to 5 carbon atoms which may contain an oxygen atom or a sulfur atom; n' represents an integer of 0 to 2; m' represents 0 or 1; and * represents a valence bond:

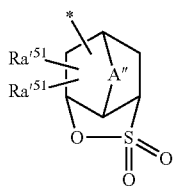 (a5-r-1)

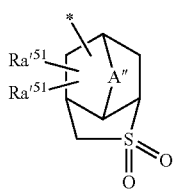 (a5-r-2)

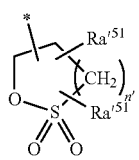 (a5-r-3)

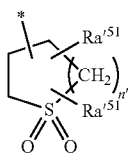 (a5-r-4)

wherein each $Ra'^{51}$ independently represents a hydrogen atom, an alkyl group, an alkoxy group, a halogen atom, a halogenated alkyl group, a hydroxy group, —COOR″, —OC(=O)R″, a hydroxyalkyl group or a cyano group; R″ represents a hydrogen atom or an alkyl group; A″ represents an oxygen atom, a sulfur atom or an alkylene group of 1 to 5 carbon atoms which may contain an oxygen atom or a sulfur atom; n' represents an integer of 0 to 2; and * represents a valence bond; and a photo-decomposable quencher (D0) containing a compound represented by general formula (d0) shown below:

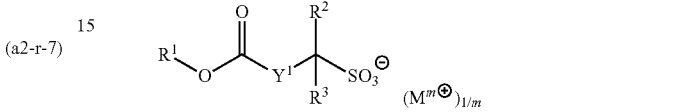 (d0)

wherein $R^1$ represents a cyclic aliphatic hydrocarbon group represented by any one of formulae (r-lc-1-1) to (r-lc-1-2), (r-lc-2-1), (r-lc-2-7), (r-lc-6-1), (r-lc-7-1), (r-sl-1-1) and (r-sl-1-18) shown below:

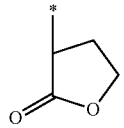 (r-lc-1-1)

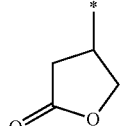 (r-lc-1-2)

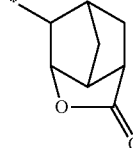 (r-lc-2-1)

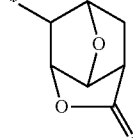 (r-lc-2-7)

 (r-lc-6-1)

 (r-lc-7-1)

-continued

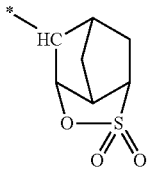
(r-sl-1-1)

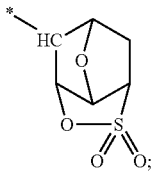
(r-sl-1-18)

$Y^1$ represents a single bond or a divalent linking group; $R^2$ and $R^3$ each independently represents a substituent of 0 to 20 carbon atoms other than a fluorine atom; one of $R^2$ and $R^3$ may form a ring with Y'; $M^{m+}$ represents an organic cation having a valency of m; and m represents an integer of 1 or more.

2. The resist composition according to claim 1, wherein the base component (A) comprises a resin compound (A1) which comprises a structural unit (a1) containing an acid decomposable group that exhibits increased polarity by the action of acid.

3. The resist composition according to claim 1, wherein $Y^1$ represents a single bond or an alkylene group of 1 to 5 carbon atoms which may have a substituent.

4. The resist composition according to claim 1, wherein $R^2$ and $R^3$ each independently represents a hydrogen atom, an alkyl group, an alkenyl group, an alkynyl group, an aryl group, a substituted or unsubstituted amino group, an alkoxy group, an aryloxy group, an acyl group, an alkoxycarbonyl group, an aryloxycarbonyl group, an acyloxy group, an acylamino group, an alkoxycarbonylamino group, and aryloxycarbonylamino group, a sulfonylamino group, a hydroxy group, a mercapto group, a chlorine atom, a bromine atom, an iodine atom, a cyano group, a sulfo group, a carboxyl group, a nitro group, a hydroxamic acid group, a sulfino group, a hydrazino group, an imino group, a heterocyclic group, or a silyl group.

5. The resist composition according to claim 1, wherein $R^2$ and $R^3$ each represents a hydrogen atom.

6. The resist composition according to claim 1, wherein $V''^{101}$ represents —$CF_2$—, —$CF_2CF_2$—, —$CHFCF_2$—, —$CF(CF_3)CF_2$— or —$CH(CF_3)CF_2$—.

7. A method of forming a resist pattern, comprising: forming a resist film on a substrate using a resist composition of claim 1; conducting exposure of the resist film; and developing the resist film to form a resist pattern.

* * * * *

UNITED STATES PATENT AND TRADEMARK OFFICE
CERTIFICATE OF CORRECTION

PATENT NO. : 9,040,224 B2
APPLICATION NO. : 14/133000
DATED : May 26, 2015
INVENTOR(S) : Akiya Kawaue, Takaaki Kaiho and Tsuyoshi Nakamura Page 1 of 1

It is certified that error appears in the above-identified patent and that said Letters Patent is hereby corrected as shown below:

In the Specification:
Col. 9, line 28, "Ra'$^1$" should be --Ra'$^5$--.
Col. 30, line 43, "—Y$^{22}$" should be -- —Y$^{22}$— --.
Col. 50, line 63, "norbonyl" should be --norbornyl--.
Col. 50, line 64, "norbonyl" should be --norbornyl--.
Col. 62, line 64, "R$^{101}$" should be --Y$^{101}$--.
Col. 63, line 56, after "—CH(CH$_2$CH$_3$)—," insert -- —C(CH$_3$)$_2$—,--.
Col. 66, line 66, "pheylthio" should be --phenylthio--.
Col. 87, line 14, "benzoly" should be --benzoyl--.
Col. 87, line 29, "benzolyamino" should be --benzoylamino--.
Col. 87, line 52, "benzthiazolyl" should be --benzothiazolyl--.
Col. 88, line 58, "R$^{04}$" should be --Ra$^{04}$--.
Col. 88, line 64, "R$^{04}$" should be --Ra$^{04}$--.
Col. 89, line 1, "R$^{04}$" should be --Ra$^{04}$--.
Col. 89, line 3, "R$^{04}$" should be --Ra$^{04}$--.
Col. 109, line 1, "H," should be --3.11 (s, 1H,--.
Col. 117-118, line 4, "1H,Sultone)," should be --1H, Sultone),--.
Col. 123-124, line 10, "4H" should be --4H,--.
Col. 137, line 33, "formed" should be --formed.--.
In the Claims:
Col. 139, line 49 (claim 1), "re resents" should be --represents--.
Col. 139, line 50 (claim 1), "m:" should be --m;--.
Col. 139, line 55 (claim 1), "got" should be --group--.
Col. 139, line 63 (claim 1), "ma" should be --may--.
Col. 139, line 63 (claim 1), "substituent" should be --substituent;--.
Col. 143, line 21 (claim 1), "Y';" should be --Y$^1$;--.

Signed and Sealed this
Twenty-third Day of August, 2016

Michelle K. Lee
*Director of the United States Patent and Trademark Office*